United States Patent
Klar et al.

(10) Patent No.: US 6,930,102 B2
(45) Date of Patent: Aug. 16, 2005

(54) 16-HALOGEN-EPOTHILONE DERIVATIVES, PROCESS FOR THEIR PRODUCTION, AND THEIR PHARMACEUTICAL USE

(75) Inventors: Ulrich Klar, Berlin (DE); Werner Skuballa, Berlin (DE); Bernd Buchmann, Hohen Neuendorf (DE); Wolfgang Schwede, Berlin (DE); Michael Schirner, Berlin (DE)

(73) Assignee: Schering AG, Berlin (DE)

( * ) Notice: Subject to any disclaimer, the term of this patent is extended or adjusted under 35 U.S.C. 154(b) by 94 days.

(21) Appl. No.: 10/364,337

(22) Filed: Feb. 12, 2003

(65) Prior Publication Data

US 2004/0014978 A1 Jan. 22, 2004

Related U.S. Application Data

(62) Division of application No. 09/913,495, filed on Dec. 7, 2001, now Pat. No. 6,610,736.

(30) Foreign Application Priority Data

Feb. 18, 1999 (DE) .......................................... 199 08 765
Nov. 4, 1999 (DE) .......................................... 199 54 230
Feb. 18, 2000 (WO) ................................ PCT/EP00/01333

(51) Int. Cl.[7] ..................... A61K 31/395; C07D 269/00
(52) U.S. Cl. ....................... 514/183; 514/183; 540/454; 540/462
(58) Field of Search ................................. 514/183, 450; 540/454, 462

(56) References Cited

U.S. PATENT DOCUMENTS

2004/0058969 A1 * 3/2004 Buchmann et al. .......... 514/365

FOREIGN PATENT DOCUMENTS

| EP | 0 353 732 A | 2/1990 |
| EP | 0 353 832 A | 7/1990 |
| EP | 0 435 843 A | 7/1991 |
| WO | WO 9825929 A | 6/1998 |
| WO | WO-98/25929 | * 6/1998 ......... C07D/493/04 |
| WO | WO 9907692 A | 2/1999 |
| WO | WO 0000485 A | 1/2000 |

OTHER PUBLICATIONS

CAPLUS Accession No: 2001:661399, abstract of "Synthesis of epothilones, intermediates, and analogs for use in treatment of cancers w/multidrug resistant phenotype," PCT Int. Appl. No. WO 2001064650, Danishefshky et al (2001).*
Crich, David et al: "Asymmetric synthesis of a taxol C–ring by aldol condensation and radical cyclization" TETAHE-DRON (1977), 53 (21), 7127–7138, XP004105693; p. 7130.
Nagasawa, Kazuo et al: "An efficient asymmetric synthesis of 1.alpha., 25–(OH)2 vitamin D3 A–ring synthon" J. Org. Chem. (1993), 58(9), 2523–9, XP002150715; Seite 2524; Abbildung IV: Seite 2525; Abbildungen.
Allendinger, Thomas et al: "Fluoroolefin dipeptide isosteres. II. Enantioselective synthesis of both antipodes of the Phe–Gly Dipeptide mimic" Tetrahedron Lett. (1990), 31(50), 7301–4, Seite 7302.

* cited by examiner

*Primary Examiner*—Janet L. Coppins
(74) *Attorney, Agent, or Firm*—Millen, White, Zelano & Branigan, P.C.

(57) ABSTRACT

A compund of formula I, an epothilone derivative, its method of preparation, and use as a pharmaceutical agent in treating malignant tumors

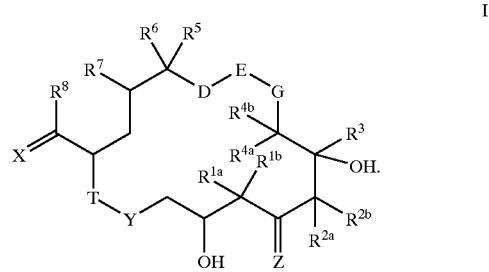

53 Claims, No Drawings

16-HALOGEN-EPOTHILONE DERIVATIVES, PROCESS FOR THEIR PRODUCTION, AND THEIR PHARMACEUTICAL USE

Höfle et al. describe the cytotoxic action of the natural substances epothilone A (R=hydrogen) and epothilone B (R=methyl)

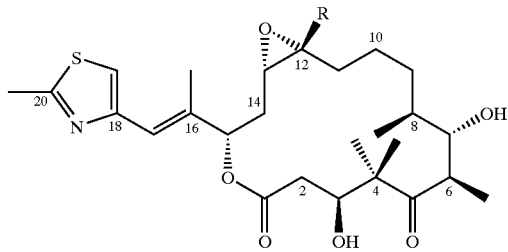

Epothilone A (R=H), Epothilone B (R=CH$_3$) in, e.g., Angew. Chem. [Applied Chem.], 1996, 108, 1671–1673. Because of their in-vitro selectivity for breast cell lines and intestinal cell lines and their significantly higher activity against P-glycoprotein-forming, multiresistant tumor lines in comparison to taxol as well as their physical properties that are superior to those of taxol, e.g., a water solubility that is higher by a factor of 30, this novel structural class is especially advantageous for the development of a pharmaceutical agent for treating malignant tumors.

The natural substances are not sufficiently stable either chemically or metabolically for the development of pharmaceutical agents. To eliminate these drawbacks, modifications to the natural substance are necessary. Such modifications are possible only with a total-synthesis approach and require synthesis strategies that make possible a broad modification of the natural substance. The purpose of the structural changes is also to increase the therapeutic range. This can be done by improving the selectivity of the action and/or increasing the active strength and/or reducing undesirable toxic side-effects, as they are described in Proc. Natl. Acad. Sci. USA 1998, 95, 9642–9647.

The total synthesis of epothilone A is described by Schinzer et al. in Chem. Eur. J. 1996, 2, No. 11, 1477–1482 and in Angew. Chem. 1997, 109, No. 5, pp. 543–544). Epothilone derivatives were already described by Höfle et al. in WO 97/19086. These derivatives were produced starting from natural epothilone A or B. Also, epothilone C and D (double bond between carbon atoms 12, and 13: epothilone C=deoxyepothilone A; epothilone D=deoxyepothilone B) are described as possible starting products for this purpose.

Another synthesis of epothilone and epothilone derivatives was described by Nicolaou et al. in Angew. Chem. 1997, 109, No. 1/2, pp. 170–172. The synthesis of epothilone A and B and Several epothilone analogs was described in Nature, Vol. 387, 1997, pp. 268–272; and the synthesis of epothilone A and its derivatives was described in J. Am. Chem. Soc., Vol. 119, No. 34, 1997, pp. 7960–7973 as well as the synthesis of epothilone A and B and several epothilone analogs in J. Am. Chem. Soc., Vol. 119, No. 34, 1997, pp. 7974–7991 also by Nicolaou et al.

Nicolaou et al. also describe in Angew. Chem. 1997, 109, No. 19, pp. 2181–2187 the production of epothilone A analogs using combinatory solid-phase synthesis. Several epothilone B analogs are also described there.

Epothilone derivatives, in some cases also epothilone C and D, are further described in patent applications WO 99/07692, WO 99/02514, WO 99/01124, WO 99/67252, WO 98/25929, WO 97/19086, WO 98/38192, WO 99/22461 and WO 99/58534.

In the epothilone derivatives that became known previously, no halogen atom can stand at carbon atom 16 of the epothilone skeleton.

The content of the priority documents DE 199 08 765.2 and DE 199 54 230.9 in this patent applicant as well as in WO 99/07692 of the applicant is incorporated by reference in these documents as part of the disclosure in this patent application.

The object of this invention consists in making available new epothilone derivatives, which are both chemically and metabolically stable enough for the development of pharmaceutical agents and which are superior to natural derivatives in terms of their therapeutic range, their selectivity of action and/or undesirable toxic side-effects and/or their active strength.

This invention describes the new epothilone derivatives of general formula I,

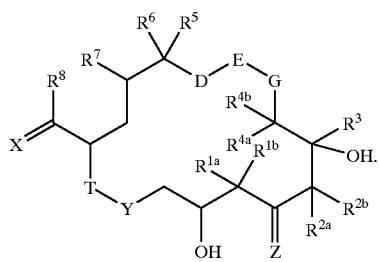

in which
$R^{1a}$, $R^{1b}$ are the same or different and mean hydrogen, $C_1$–$C_{10}$ alkyl, aryl, $C_7$–$C_{20}$ aralkyl, or together a —(CH$_2$)$_m$ group with m=2, 3, 4 or 5,
$R^{2a}$, $R^{2b}$ are the same or different and mean hydrogen, $C_1$–$C_{10}$ alkyl, aryl, $C_7$–$C_{20}$ aralkyl or together a —(CH$_2$)$_n$ group with n=2, 3, 4 or 5,
$R^3$ means hydrogen, $C_1$–$C_{10}$ alkyl, aryl, $C_7$–$C_{20}$ aralkyl,
G means an oxygen atom or a group CH$_2$,
$R^{4a}$, $R^{4b}$ are the same or different and mean hydrogen, $C_1$–$C_{10}$ alkyl, aryl, $C_7$–$C_{20}$ aralkyl or together a —(CH$_2$)$_p$ group with p=2, 3, 4 or 5,
D—E means a group

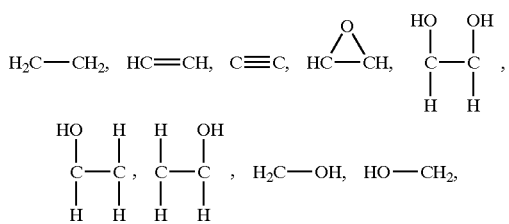

$R^5$ means hydrogen, $C_1$–$C_{10}$ alkyl, aryl, $C_7$–$C_{20}$ aralkyl, CO$_2$H, CO$_2$-alkyl, CH$_2$OH, CH$_2$O-alkyl, CH$_2$O-acyl, CN, CH$_2$NH$_2$, CH$_2$N(alkyl, acyl)$_{1,2}$, CH$_2$Hal
$R^6$, $R^7$ each mean a hydrogen atom, together an additional bond or an oxygen atom,
$R^8$ means a halogen atom, or a cyano group,
X means an oxygen atom, two alkoxy groups OR$^{23}$, a $C_2$–$C_{10}$ alkylene-α,ω-dioxy group, which can be straight-chain or branched, H/OR$^9$ or a grouping CR$^{10}$R$^{11}$, whereby $R^{23}$ stands for a $C_1$–$C_{20}$ alkyl radical, $R^9$ stands for hydrogen or a protective group $PG^x$, $R^{10}$, $R^{11}$ are the same or different and stand for hydrogen, a $C_1$–$C_{20}$ alkyl, aryl, $C_7$–$C_{20}$ aralkyl radical or $R^{10}$ and $R^{11}$ together with the methylene carbon atom together stand for a 5- to 7-membered carbocyclic ring, T—Y means a group O—C(=O), O—CH$_2$, CH$_2$C(=O), $NR^{24}$—C(=O), $NR^{24}$—SO$_2$, $R^{24}$ means hydrogen, $C_1$–$C_{10}$ alkyl, Z means an oxygen atom or H/OR$^{12}$, whereby $R^{12}$ is hydrogen or a protective group $PG^z$.

Halogen atom $R^8$ can be a fluorine, chlorine, bromine or iodine atom. Fluorine, chlorine and bromine are preferred, and of the latter especially fluorine and chlorine.

$R^{2a}$ is preferably to mean a methyl, ethyl, propyl or butyl group.

A trimethylene group preferably commonly stands for substituents $R^{1a}$ and $R^{1b}$, or $R^{1a}$ and $R^{1b}$ each mean a methyl group.

$R^{10}/R^{11}$ in group X preferably stand for a 2-pyridyl radical/hydrogen or a 2-methyl-4-thiazolyl radical/hydrogen or a 2-hydroxymethyl-4-thiazolyl radical/hydrogen or a 2-methyl-4-oxazolyl radical/hydrogen or a 2-hydroxymethyl-4-oxazolyl radical/hydrogen.

T—Y is preferably a group O—C(=O) or a group $NR^{24}$—C(=O).

Z primarily means an oxygen atom.

Between carbon atoms 10 and 11, there is a simple bond in the preferred compounds of general formula I, i.e., —D—E— stands for an ethylene group.

In addition, $R^3$ usually stands for a hydrogen atom in the compounds according to the invention.

The combination H/CH$_3$, preferably stands for the two substituents $R^{4a}/R^{4b}$.

An embodiment of the invention calls for those compounds of general formula I in which $R^8$ stands for a fluorine atom or chlorine atom and $R^{1a}+R^{1b}$ together mean a trimethylene group.

According to another embodiment, the invention relates to those compounds of general formula I in which $R^8$ stands for a fluorine atom or chlorine atom and $R^{10}/R^{11}$ stand for a 2-pyridyl radical/hydrogen.

Still another variant are those compounds of general formula I in which $R^8$ stands for a fluorine atom or chlorine atom, and $R^{2a}/R^{2b}$ stand for ethyl/hydrogen.

Still another embodiment of the invention are those compounds of general formula I, in which $R^8$ stands for a fluorine atom or chlorine atom, $R^{1a}+R^{1b}$ together mean a trimethylene group and $R^{2a}/R^{2b}$ stand for ethyl/hydrogen.

In addition, this variant for the compounds according to the invention can be mentioned in which $R^8$ stands for a fluorine atom or chlorine atom, $R^{2a}/R^{2b}$ stand for ethyl/hydrogen and $R^{10}/R^{11}$ stand for a 2-pyridyl radical/hydrogen.

Further embodiments of this invention will emerge from the features of the subclaims.

The production of the new epothilone derivatives is based on the linkage of three partial fragments A, B and C. This process is described in DE 197 51 200.3, date of application Nov. 13, 1997 as well as in the corresponding WO 99/07692 for the production of epothilone derivatives, which as $R^8$ contain, for example, a methyl or longer alkyl group instead of the halogen atom according to the invention. The interfaces are as indicated in general formula I'.

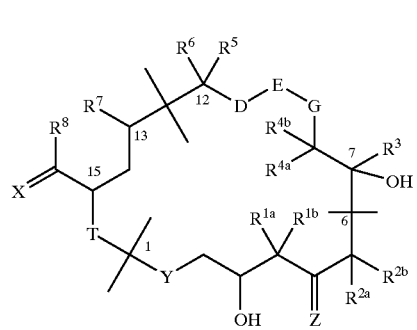

I'

A means a C1–C6 fragment (epothilone numbering system) of general formula

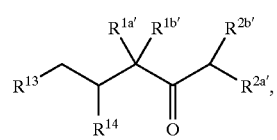

A in which $R^{1a'}$, $R^{1b'}$, $R^{2a'}$ and $R^{2b'}$ have the meanings already mentioned for $R^{1a}$, $R^{1b}$, $R^{2a}$ and $R^{2b}$, and $R^{13}$ means CH$_2$OR$^{13a}$, CH$_2$—Hal, CHO, CO$_2$R$^{13b}$, COHal, $R^{14}$ means hydrogen, OR$^{14a}$, Hal, OSO$_2$R$^{14b}$, $R^{13a}$, $R^{14a}$ mean hydrogen, SO$_2$-alkyl, SO$_2$-aryl, SO$_2$-aralkyl or together a —(CH$_2$)$_o$ group or together a CR$^{15a}$R$^{15b}$ group, $R^{13b}$, $R^{14b}$ mean hydrogen, $C_1$–$C_{20}$ alkyl, aryl, $C_7$–$C_{20}$ aralkyl, $R^{15a}$, $R^{15b}$ are the same or different and mean hydrogen, $C_1$–$C_{10}$ alkyl, aryl, $C_7$–$C_{20}$ aralkyl or together a —(CH$_2$)$_q$ group, Hal means halogen (F, Cl, Br, I), o means 2 to 4, q means 3 to 6, including all stereoisomers as well as their mixtures, and free hydroxyl groups in $R^{13}$ and $R^{14}$ can be etherified or esterified, free carbonyl groups can be ketalized in A and $R^{13}$, converted into an enol ether or reduced, and free acid groups in A can be converted into their salts with bases.

B stands for a C7–C12 fragment (epothilone numbering system) of general formula

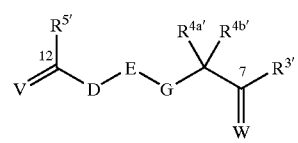

B in which $R^{3'}$, $R^{4a'}$, $R^{4b'}$ and $R^{5'}$ have the meanings already mentioned for $R^3$, $R^{4a}$, $R^{4b}$ and $R^5$, and D, E and G have the meanings that are indicated in general formula I, and V means an oxygen atom, two alkoxy groups OR$^{17}$, a $C_2$–$C_{10}$ alkylene-α,ω-dioxy group, which can be straight-chain or branched or H/OR$^{16}$, W means an oxygen atom, two alkoxy groups $OR^{19}$, a $C_2$–$C_{10}$ alkylene-α,ω-dioxy group, which can be straight-chain or branched or $H/OR^{18}$, $R^{16}$, $R^{18}$, independently of one another, mean hydrogen or a protective group $PG^1$ $R^{17}$, $R^{19}$, independently of one another, mean $C_1$–$C_{20}$ alkyl.

C stands for a C13–C16 fragment (epothilone numbering system) of general formula

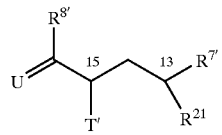

C in which $R^{8'}$ has the meaning already mentioned in general formula I for $R^8$ (halogen), and $R^{7'}$ means a hydrogen atom, T' means a group $OR^{20}$, whereby $R^{20}$ is a hydrogen atom or a protective group $PG^2$, a halogen atom, preferably a bromine or iodine atom, an azido group or a protected amino group, $R^{21}$ means a hydroxy group, halogen, a protected hydroxy group $OPG^3$, a phosphonium halide radical $PPh_3{}^+Hal^-$ (Ph=phenyl; Hal=F, Cl, Br, I), a phosphonate radical $P(O)(OQ)_2$ (Q=$C_1$–$C_{10}$ alkyl or phenyl) or a phosphine oxide radical $P(O)Ph_2$ (Ph=phenyl), U means an oxygen atom, two alkoxy groups $OR^{23}$, a $C_2$–$C_{10}$ alkylene-α,ω-dioxy group, which can be straight-chain or branched, $H/OR^9$ or a grouping $CR^{10}R^{11}$, whereby $R^{23}$ stands for a $C_1$–$C_{20}$ alkyl radical, $R^9$ stands for hydrogen or a protective group $PG^3$, $R^{10}$, $R^{11}$ are the same or different and stand for hydrogen, a $C_1$–$C_{20}$ alkyl, aryl, $C_7$–$C_{20}$ aralkyl radical or $R^{10}$ and $R^{11}$ together with the methylene carbon atom commonly stand for a 5- to 7-membered carbocyclic ring.

As alkyl groups $R^{1a}$, $R^{1b}$, $R^{2a}$, $R^{2b}$, $R^3$, $R^4$, $R^5$, $R^9$, $R^{10}$, $R^{11}$, $R^{12}$, $R^{13b}$, $R^{14b}$, $R^{15a}$, $R^{15b}$, $R^{17}$ and $R^{23}$, straight-chain or branched-chain alkyl groups with 1–20 carbon atoms can be considered, such as, for example, methyl; ethyl, propyl, isopropyl, butyl, isobutyl, tert-butyl, pentyl, isopentyl, neopentyl, heptyl, hexyl, decyl.

Alkyl groups $R^{1a}$, $R^{1b}$, $R^{2a}$, $R^{2b}$, $R^3$, $R^4$, $R^5$, $R^9$, $R^{10}$, $R^{11}$, $R^{12}$, $R^{13b}$, $R^{14b}$, $R^{15a}$, $R^{15b}$, $R^{17}$ and $R^{23}$ can be perfluorinated or substituted by 1–5 halogen atoms, hydroxy groups, $C_1$–$C_4$ alkoxy groups, $C_6$–$C_2$ aryl groups (which can be substituted by 1–3 halogen atoms).

As aryl radicals $R^{1a}$, $R^{1b}$, $R^{2a}$, $R^{2b}$, $R^3$, $R^4$, $R^5$, $R^9$, $R^{10}$, $R^{11}$, $R^{12}$, $R^{13b}$, $R^{14b}$, $R^{15a}$ and $R^{15b}$, substituted and unsubstituted carbocyclic or heterocyclic radicals with one or more heteroatoms, such as, e.g., phenyl, naphthyl, furyl, thienyl, pyridyl, pyrazolyl, pyrimidinyl, oxazolyl, pyridazinyl, pyrazinyl, quinolyl, thiazolyl, which can be substituted in one or more places by halogen, OH, O-alkyl, $CO_2H$, $CO_2$-alkyl, —$NH_2$, —$NO_2$, —$N_3$, —CN, $C_1$–$C_{20}$ alkyl, $C_1$–$C_{20}$ acyl, $C_1$–$C_{20}$ acyloxy groups, are suitable. Heteroatoms in the heteroaryl radicals can be oxidized; thus, for example, the thiazole ring can be present in the form of N-oxide.

Unless otherwise indicated, the definition of "aryl" always also includes "heteroaryl."

The aralkyl groups in $R^{1a}$, $R^{1b}$, $R^{2a}$, $R^{2b}$, $R^3$, $R^4$, $R^5$, $R^9$, $R^{10}$, $R^{11}$, $R^{12}$, $R^{13b}$, $R^{14b}$, $R^{15a}$ and $R^{15b}$ can contain in the ring up to 14 C atoms, preferably 6 to 10, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridylpropyl are suitable. The rings can be substituted in one or more places by halogen, OH, O-alkyl, $CO_2H$, $CO_2$-alkyl, —$NO_2$, —$N_3$, —CN, $C_1$–$C_{20}$ alkyl, $C_1$–$C_{20}$ acyl, $C_1$–$C_{20}$ acyloxy groups.

The alkoxy groups that are contained in X in general formula I are in each case to contain 1 to 20 carbon atoms, whereby methoxy, ethoxy, proppxy, isopropoxy and t-butyloxy groups are preferred.

As representatives of protective groups PG, alkyl- and/or aryl-substituted silyl, $C_1$–$C_{20}$ alkyl, $C_4$–$C_7$ cycloalkyl, which in addition in the ring can contain an oxygen atom, aryl, $C_7$–$C_{20}$ aralkyl, $C_1$–$C_{20}$ acyl and aroyl can be mentioned.

As alkyl, silyl and acyl radicals for protective groups PG, the radicals that are known to one skilled in the art are suitable. Preferred are alkyl or silyl radicals that can be easily cleaved from the corresponding alkyl and silyl ethers, such as, for example, the methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl radical as well as alkylsulfonyl and arylsulfonyl radicals. As acyl radicals, e.g., formyl, acetyl, propionyl, isopropionyl, pivalyl, butyryl or benzoyl, which can be substituted with amino groups and/or hydroxy groups, are suitable.

Acyl groups $PG^x$ or $PG^z$ in $R^9$ and $R^{12}$ can contain 1 to 20 carbon atoms, whereby formyl, acetyl, propionyl, isopropionyl and pivalyl groups are preferred.

As amino protective groups, the radicals that are known to one skilled in the art are suitable. For example, the Boc-, Z-, benzyl, f-Moc, Troc-, Stabase or Benzostabase groups can be mentioned.

Index m in the alkylene group that is formed from $R^{1a}$ and $R^{1b}$ preferably stands for 2, 3 or 4.

The $C_2$–$C_{10}$ alkylene-α,ω-dioxy group that is possible for X is preferably an ethyleneketal or neopentylketal group.

This invention relates in particular to the following compounds:

(4S,7R,8S,9S,13(Z or E),16S(Z))-4,8-Dihydroxy-16-(1-fluoro-2-(2-methyl-4-thiazolyl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-methyl-4-thiazolyl)ethenyl)-8,8,10,12,16,-pentamethyl-4,17-dioxabicyclo[14.1.0]heptadecane-5,9-dione (4S,7R,8S,9S,13(Z or E),16S(Z))-4,8-dihydroxy-7-ethyl-16-(1-fluoro-2-(2-methyl-4-thiazolyl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-methyl-4-thiazolyl)ethenyl)-8,8,12,16-tetramethyl-4,17-dioxabicyclo[14.1.0] heptadecane-5,9-dione (4S,7R,8S,9S,13(Z or E),16S(Z))-4,8-dihydroxy-16-(1-fluoro-2-(2-methyloxazol-4-yl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-methyloxazol-4-yl)ethenyl)-8,8,10,12,16-pentamethyl-4,17-dioxabicyclo[14.1.0]heptadecane-5,9-dione (4S,7R,8S,9S,13(Z or E),16S(Z))-4,8-dihydroxy7-ethyl-16-(1-fluoro-2-(2-methyloxazol-4-yl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-methyloxazol-4-yl)ethenyl)-8,8,12,16-tetramethyl-4,17-dioxabicyclo[14.1.0]heptadecane-5,9-dione (4S,7R,8S,9S,13(Z or E),16S(Z))-4,8-dihydroxy-16-(1-fluoro-2-(2-pyridyl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-pyridyl)ethenyl)-8,8,10,12,16-pentamethyl-4,17-dioxabicyclo[14.1.0]heptadecane-5,9-dione (4S,7R,8S,9S,13(Z or E),16S(Z))-4,8-dihydroxy-7-ethyl-16-(1-fluoro-2-(2-pyridyl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-pyridyl)ethenyl)-8,8,12,16-tetramethyl-4,17-dioxabicyclo[14.1.0]heptadecane-5,9-dione (4S,7R,8S,9S,13(Z or E),16S(Z))-4,8-dihydroxy-16-(1-fluoro-2-(2-methyl-4-thiazolyl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-methyl-4-thiazolyl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-fluoro-2-(2-methyl-4-thiazolyl)ethenyl)-1-aza-5,5,9,13-tetramethyl-cyclohexadec-13-ene-2,6-dione (1RS,3S(Z),7S,10R,11S,12S,16RS),-7,11-dihydroxy-10-ethyl-3-(1-fluoro-2-(2-methyl-4-thiazol)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-fluoro-2-(2-methyloxazol-4-yl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-methyloxazol-4-yl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-fluoro-2-(2-methyloxazol-4-yl)ethenyl)-1-aza-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-fluoro-2-(2pyridyl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-pyridyl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-fluoro-2-(2-pyridyl)ethenyl)-1-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-pyridylethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-chloro-2-(2-methyl-4-thiazolyl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-methyl-4-thiazolyl)ethenyl)-8,8,10,12,16-pentamethyl-4,17-dioxabicyclo[14.1.0]heptadecane-5,9-dione (4S,7R,8S,9S,13(Z or E),16S(Z))-4,8-dihydroxy-7-ethyl-16-(1-chloro-2-(2-methyl-4-thiazolyl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-methyl-4-thiazolyl)ethenyl)-8,8,12,16-tetramethyl-4,17-dioxabicyclo[14.1.0]heptadecane-5,9-dione (4S,7R,8S,9S,13(Z or E),16S(Z))-4,8-dihydroxy-16-(1-chloro-2-(2-methyloxazol-4-yl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-methyloxazol-4-yl)ethenyl)-8,8,10,12,16-pentamethyl-4,17-dioxabicyclo[14.1.0]heptadecane-5,9-dione (4S,7R,8S,9S,13(Z or E),16S(Z))-4,8-dihydroxy-7-ethyl-16-(1-chloro-2-(2-methyloxazol-4-yl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-methyloxazol-4-yl)ethenyl)-8,8,12,16-tetramethyl-4,17-dioxabicyclo[14.1.0]heptadecane-5,9-dione (4S,7R,8S,9S,13(Z or E),16S(Z))-4,8-dihydroxy-16-(1-chloro-2-(2-pyridyl)ethenyl)-1-oxa-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-pyridyl)ethenyl)-8,8,10,12,16-pentamethyl-4,17-dioxabicyclo[14.1.0]-heptadecane-5,9-dione (4S,7R,8S,9S,13(Z or E),16S(Z))-4,8-dihydroxy-7-ethyl-16-(1-chloro-2-(2-pyridyl)ethenyl)-1-oxa-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-pyridyl)ethenyl)-8,8,12,16-tetramethyl-4,17-dioxabicyclo[14.1.0]heptadecane-5,9-dione (4S,7R,8S,9S,13(Z or E),16S(Z))-4,8-dihydroxy-16-(1-chloro-2-(2-methyl-4-thiazolyl)ethenyl)-1-aza-5,5,7,9,13-pentamethyl-cyclohexadec-13-ene-2,6-dione (1RS,3S(z),7S,10R,11S,12S,16RS)-7,11-dihydroxy-3-(1-chloro-2-(2-methyl-4-thiazolyl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-chloro-2-(2-methyl-4-thiazolyl)ethenyl)-1-aza-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-methyl-4-thiazolyl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-chloro-2-(2-methyloxazol-4-yl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-methyloxazol-4-yl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-chloro-2-(2-methyloxazol-4-yl)ethenyl)-1aza-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-methoxazol-4-yl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-chloro-2-(2-pyridyl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-pyridyl)ethenyl)-8,8,10,12,16-pentamethyl-4-aza-17-oxabicyclo[14.1.0]-heptadecane-5,9-dione (4S,7R,8S,9S,13(Z or E),16S(Z))-4,8-dihydroxy-7-ethyl-16-(1-chloro-2-(2-pyridyl)ethenyl)-1-aza-5,5,9,13-tetramethyl-cyclohexadec-13-ene-2,6-dione (1RS,3S(Z),7S,10R, 11S,12S,16RS)-7,11-dihydroxy-10-ethyl-3-(1-chloro-2-(2-pyridyl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-fluoro-2-(2-methyl-4-thiazolyl)ethenyl)-1-oxa-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-fluoro-2-(2-methyl-4-thiazolyl)ethenyl)-10,12,16-trimethyl-8,8-(1,3-trimethylene)-4,17-dioxabicyclo[14.1.0]hepta-deca-5,9-dione (4S,7R,8S,9S,13(Z or E),16S(Z))-4,8-dihydroxy-9,13-dimethyl-7-ethyl-16-(1-fluoro-2-(2-methyl-4-thiazolyl)ethenyl)-1-oxz-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-fluoro-2-(2-methyl-4-thiazolyl)ethenyl)-8,8-(1,3-trimethylene)-4,17-dioxabicyclo[14.1.0]hepta-decane-5,9-dione (4S,7R,8S,9S,13(Z or E),16S(Z))-4,8-dihydroxy-16-(1-fluoro-2-(2-methyl-4-thiazolyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-fluoro-2-(2-methyl-4-thiazolyl)ethenyl)-10,12,16-trimethyl-8,8-(1,3-trimethylene)-4-aza-17-oxabicyclo[14.1.0]hepta-deca-5,9-dione (4S,7R,8S, 9S,13 (Z or E),16S(Z))-4,8-dihydroxy-9,13-dimethyl-7-ethyl-16-(1-flyoro-2-(2-methyl-4-thiazolyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-fluoro-2-(2-methyl-4-thiazolyl)ethenyl)-8,8-(1,3-trimethylene)-4-aza-17-oxabicyclo[14.1.0]hepta-decane-5,9-dione (4S,7R,8S,9S,13(Z or E),16S(Z))-4,8-dihydroxy-16-(1-chloro-2-(2-methyl-4-thiazolyl)ethenyl)-1-oxa-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-chloro-2-(2-methyl-4-thiazolyl)ethenyl)-10,12,16-trimethyl-8,8-(1,3-trimethylene)-4,17-dioxabicyclo[14.1.0]hepta-deca-5,9-dione (4S,7R,8S,9S,13(Z or E),16S(Z))-4,8-dihydroxy-9,13-dimethyl-7-ethyl-16-(1-chloro-2-(2-methyl-4thiazolyl)ethenyl)-1-oxa-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-methyl-4-thiazolyl)ethenyl)-8,8-(1,3-trimethylene)-4,17-dioxabicyclo[14.1.0]heptadecane-5,9-dione 4S,7R,8S,9S,13(Z or E),16S(Z))-4,8-dihydroxy-16-(1-chloro-2-(2-methyl-4-thiazolyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-chloro-2-(2-methyl-4-thiazolyl)ethenyl)-10,12,16-trimethyl-8,8-(1,3-trimethylene)-4-aza-17-oxabicyclo[14.1.0]hepta-deca-5,9-dione (4S,7R,8S,9S,13(Z or E),16S(Z))-4,8-dihydroxy-9,13-dimethyl-7-ethyl-16-(1-chloro-2-(2-methyl-4-thiazolyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-methyl-4-thiazolyl)ethenyl)-8,8-(1,3-trimethylene)-4-aza-17-oxabicyclo[14.1.0]heptadecane-5,9-dione (4S,7R,8S,9S,13(Z or E),16S(Z))-4,8-dihydroxy-16-(1-fluoro-2-(2-pyridyl)ethenyl)-1-oxa-7,9,13-trimethyl-5,5-(1,3-trimethylene)cyclohexadec-13-ene-2,6-dione (1RS,3S(Z), 7S,10R,11S,12S,16RS)-7,11-dihydroxy-3-(1-fluoro-2-(2-pyridyl)ethenyl)-10,12,16-trimethyl-8,8-(1,3-trimethylene)-4,17-dioxabicyclo[14.1.0]hepta-deca-5,9-dione (4S,7R,8S,9S,13(Z or E),16S(Z))-4,8-dihydroxy-9,13-dimethyl-7-ethyl-16-(1-fluoro-2-(2-pyridyl)ethenyl)-1-oxa-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-fluoro-2-(2-pyridyl)ethenyl)-8,8-(1,3-trimethylene)-4,17-dioxabicyclo[14.1.0.]hepta-decane-5,9-dione 4S,7R,8S,9S,13(Z or E),16S(Z))-4,8-dihydroxy-16-(1-fluoro-2-(2-pyridyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-fluoro-2-(2-pyridyl)ethenyl)-10,12,16-trimethyl-8,8-(1,3-trimethylene)-4-aza-17-oxabicyclo[14.1.0]hepta-deca-5,9-dione (4S,7R,8S,9S,13(Z or E),16S(Z))-4,8-dihydroxy-9,13-dimethyl-7-ethyl-16-(1-fluoro-2-(2-pyridyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1fluoro-2-(2-pyridyl)ethenyl)-8,8-(1,3-trimethylene)-4-aza-17-oxabicyclo[14.1.0]hepta-decane-5,9-dione (4S,7R,8S,9S,13(Z or E),16S(Z))-4,8-dihydroxy-16-(1-chloro-2-(2-pyridyl)ethenyl)-1-oxa-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-chloro-2-(2-pyridyl)ethenyl)-10,12,16-trimethyl-8,8-(1,3-trimethylene)-4,17-dioxabicyclo[14.1.0]hepta-deca-5,9-dione (4S,7R,8S,9S,13(Z or E),16S(Z))-4,8-dihydroxy-9,13-dimethyl-7-ethyl-16-(1-chloro-2-(2-pyridyl)ethenyl)-1-oxa-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-pyridyl)ethenyl)-8,8-(1,3-trimethylene)-4,17-dioxabicyclo[14.1.0]hepta-decane-5,9-dione (4S,7R,8S,9S,13(Z or E),16S(Z))-4,8-dihydroxy-16-(1-chloro-2-(2-pyridyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-chloro-2-(2-pyridyl)ethenyl)-10,12,16-trimethyl-8,8-(1,3-trimethylene)-4-aza-17-oxabicyclo[14.1.0]hepta-deca-5,9-dione (4S,7R,8S,9S,13(Z or E),16S(Z))-4,8-dihydroxy-9,13-dimethyl-7-ethyl-16-(1-chloro-2-(2-pyridyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-pyridyl)ethenyl)-8,8-(1,3-trimethylene)-4-aza-17-oxabicyclo[14.1.0]hepta-decane-5,9-dione Representation of Partial Fragments A and B The partial fragments (synthesis components) of general formulas A and B can be produced as described in DE 19751200.3 or the corresponding WO 99/07692.

Representation of Partial Fragments C

The representation of the partial fragments of formula C according to the invention, in which $R^{8'}$ means a fluorine atom, can be performed as is indicated in the following formula schemes within the production of the compounds of Examples 1 to 4 according to the invention.

By variation of the (hetero)aryl radical in the starting product in reaction step a) (in this case, this is the 2-methyl-4-thiazolyl radical), the correspondingly substituted components of formula C and ultimately compounds of formula I result.

The production of fragments of formula C, in which $R^{8\prime}$ means a chlorine atom, is described within Example 5.

If $R^{8\prime}$ represents a bromine atom, this is introduced analogously to a chlorine atom in fragments C.

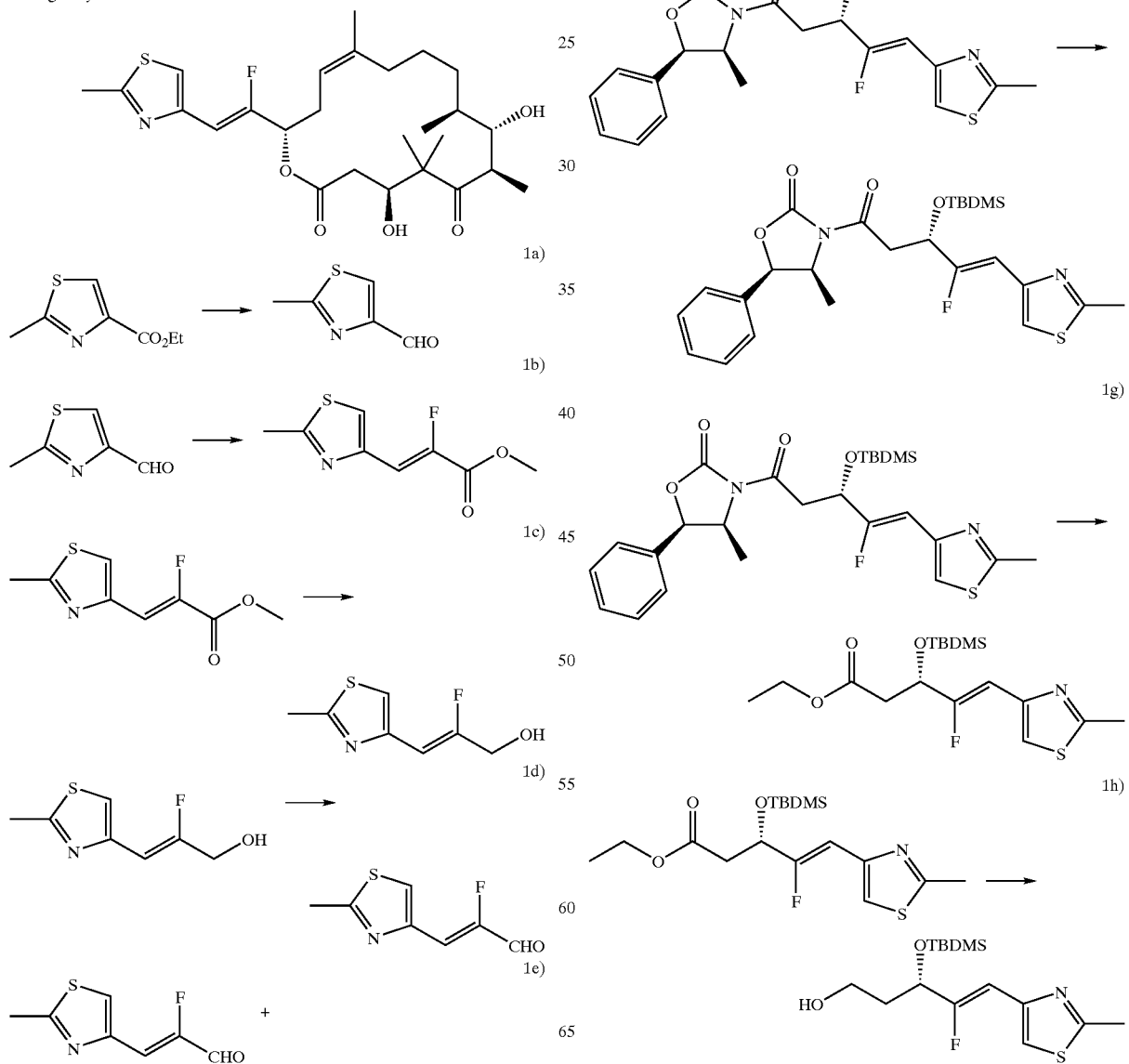

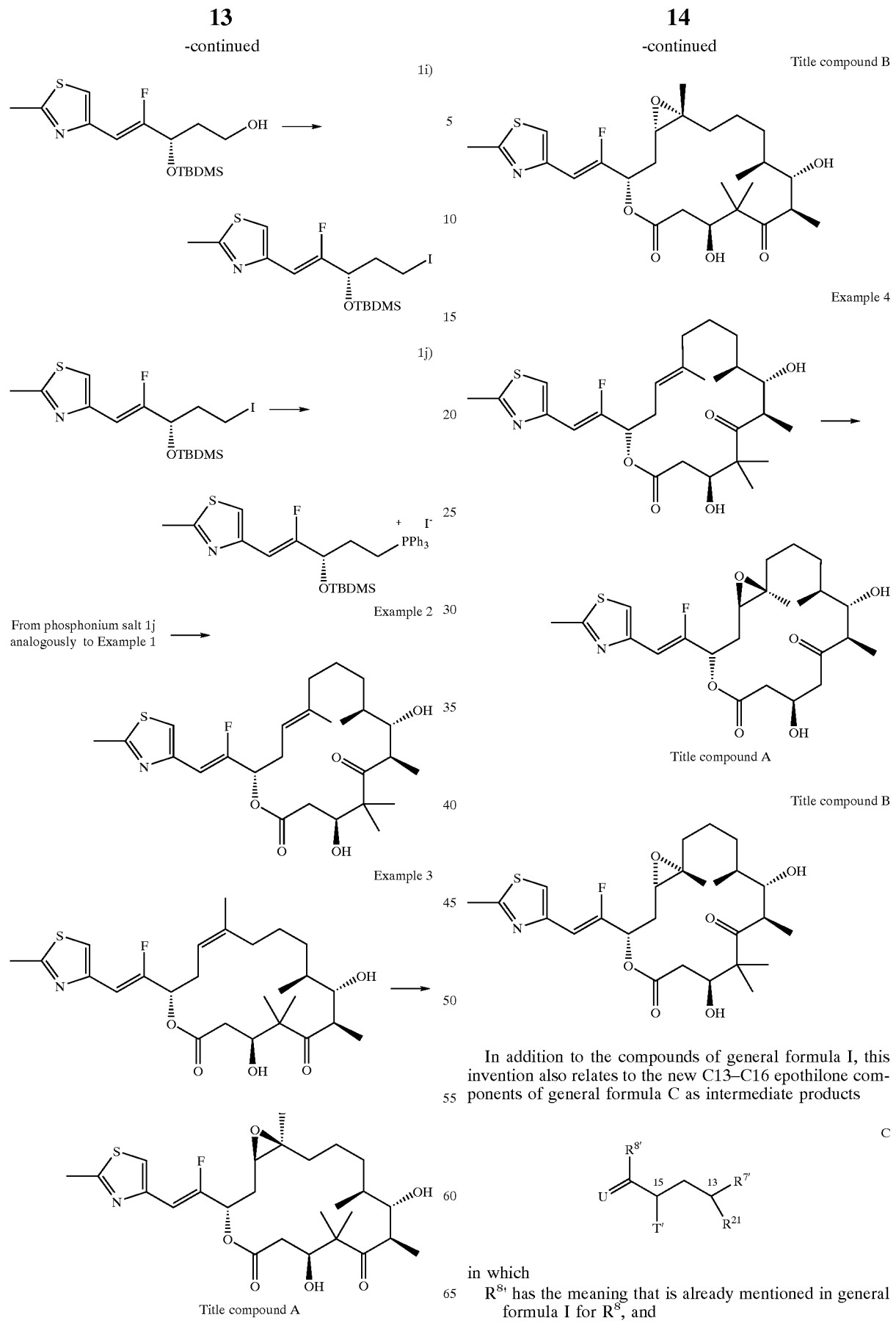
In addition to the compounds of general formula I, this invention also relates to the new C13–C16 epothilone components of general formula C as intermediate products
in which
$R^{8\prime}$ has the meaning that is already mentioned in general formula I for $R^8$, and $R^{7'}$ means a hydrogen atom, T' means a group $OR^{20}$, whereby $R^{20}$ is a hydrogen atom or a protective group $PG^2$, halogen or an azido group or a protected amino group, $R^{21}$ means a hydroxy group, halogen, a protected hydroxy group $OPG^3$, a phosphonium halide radical $PPh_3^+Hal^-$ (Ph=phenyl; Hal=F, Cl, Br, I), a phosphonate radical $P(O)(OQ)_2$ (Q=$C_1$–$C_{10}$ alkyl or phenyl) or a phosphine oxide radical $P(O)Ph_2$ (Ph=phenyl), U means an oxygen atom, two alkoxy groups $OR^{23}$, a $C_2$–$C_{10}$ alkylene-α,ω-dioxy group, which can be straight-chain or branched, $H/OR^9$ or a grouping $CR^{10}R^{11}$, whereby $R^{23}$ stands for a $C_1$–$C_{20}$ alkyl radical, $R^9$ stands for hydrogen or a protective group $PG^3$, $R^{10}$, $R^{11}$ are the same or different and stand for hydrogen, a $C_1$–$C_{20}$ alkyl, aryl, $C_7$–$C_{20}$ aralkyl radical or $R^{10}$ and $R^{11}$ together with the methylene carbon atom commonly stand for a 5- to 7-membered carbocyclic ring.

According to the invention, those compounds of general formula C are preferred, in which $R^{8'}$ stands for a fluorine, chlorine or bromine atom, and/or U stands for an oxygen atom, and/or the aryl radical that stands for $R^{10}$ and/or $R^{11}$ stands for a phenyl radical that is optionally substituted with 1 to 3 radicals, selected from the group of substituents halogen, free hydroxy group or protected hydroxy group $OPG^5$, $CO_2H$, $CO_2$-alkyl, $C_1$–$C_4$ alkyl, azido, nitro, nitrile, amino ($NH_2$), or for a 5- or 6-membered heteroaryl radical that is optionally substituted with 1 to 2 $C_1$–$C_4$ alkyl radicals, especially for a substituent that is selected from the group of 2-, 3-furanyl, 2-, 3-, 4-pyridinyl, 2-, 4-, 5-thiazolyl- and 2-, 4- and 5-imidazolyl radicals, which optionally is substituted by 1 or 2 $C_1$–$C_4$ alkyl radicals, and/or $PG^2$ and $PG^3$ are selected from the group of substituents methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl, acetyl, propionyl, butyryl and benzoyl radicals, in particular $PG^2$ is a tert-butyldimethylsilyl, acetyl, benzoyl, benzyl or tetrahydropyranyl radical.

As protective groups $PG^4$ and $PG^5$, all protective groups that are indicated above for $PG^2$ and $PG^3$ are suitable.

In addition, this invention relates to partial fragments of general formula BC

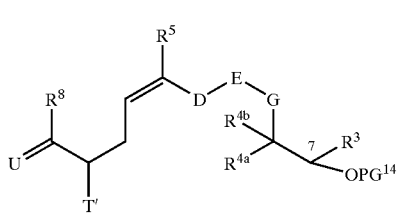

BC in which $R^3$, $R^{4a}$, $R^{4b}$, $R^5$, $R^8$, D, E, G, T' and U have the already mentioned meanings, and $PG^{14}$ represents a hydrogen atom or a protective group PG.

In addition, this invention relates to partial fragments of general formula ABC

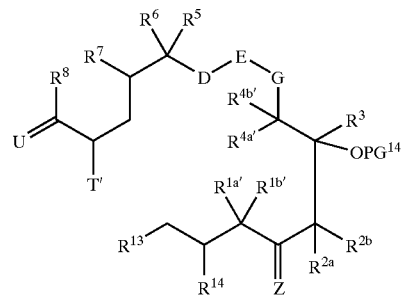

in which $R^{1a'}$, $R^{1b'}$, $R^{2a'}$, $R^{2b'}$, $R^3$, $R^{4a'}$, $R^{4b'}$, $R^5$, $R^6$, $R^7$, $R^8$, $R^{13}$, $R^{14}$, D, E, G, T', U and Z have the already mentioned meanings.

Representation of Partial Fragments ABC and Their Cyclization to I

The representation and cyclization is also carried out analogously to what is described in DE 19751200.3 or the corresponding WO 99/07692, whereby now fragment C as substituent $R^{8'}$ exhibits in particular a fluorine, chlorine or bromine atom:

Partial fragments of general formula AB

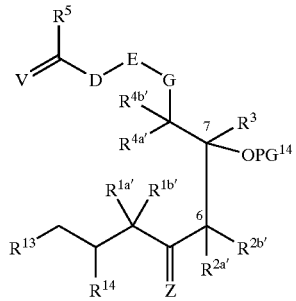

in which $R^{1a'}$, $R^{1b'}$, $R^{2a'}$, $R^{2b'}$, $R^3$, $R^{4a'}$, $R^{4b'}$, $R^5$, $R^{13}$, $R^{14}$, D, E, G, V and Z have the meanings already mentioned, and $PG^{14}$ represents a hydrogen atom or a protective group PG, are obtained from the previously described fragments A and B according to the process that is shown in Diagram 1.

Diagram 1

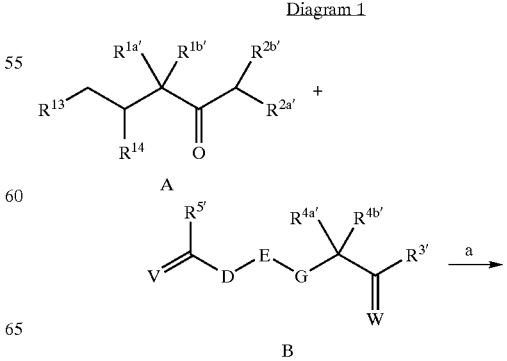

-continued

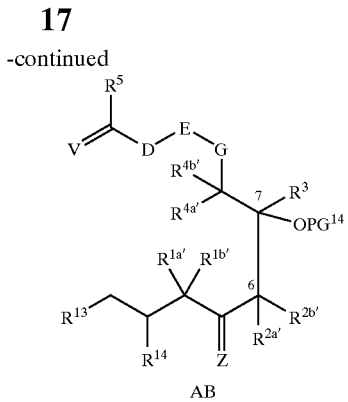

AB

Step a (A+B→AB)

Compound B, in which W has the meaning of an oxygen atom and optionally present additional carbonyl groups are protected, is alkylated with the enolate of a carbonyl compound of general formula A. The enolate is produced by action of strong bases, such as, e.g., lithium diisopropylamide, lithium hexamethyldisilazane at low temperatures.

Partial fragments of general formula ABC

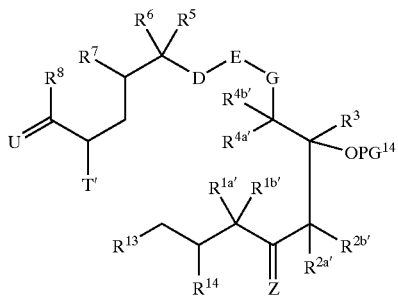

in which $R^{1a'}$, $R^{1b'}$, $R^{2a'}$, $R^{2b'}$, $R^3$, $R^{4a'}$, $R^{4b'}$, $R^5$, $R^6$, $R^7$, $R^8$, $R^{13}$, $R^{14}$, D, E, G, T', U and Z have the already mentioned meanings, are obtained from previously described fragments AB and C according to the process that is shown in Diagram 2.

Diagram 2

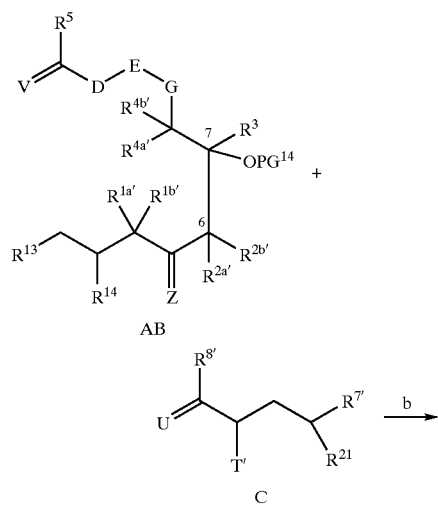

-continued

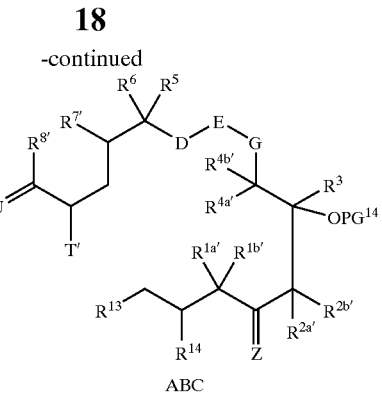

ABC

Step b (AB+C→ABC)

Compound C, in which $R^{21}$ has the meaning of a Wittig salt, and optionally present additional carbonyl groups are protected, is deprotonated by a suitable base, such as, e.g., n-butyllithium, lithium diisopropylamide, potassium tert-butanolate, sodium or lithium-hexamethyldisilazide and reacted with a compound AB, in which V has the meaning of an oxygen atom.

Step c (ABC→1)

Compounds ABC, in which $R^{13}$ represents a carboxylic acid $CO_2H$, T' stands for $OR^{20}$, and $R^{20}$ represents a hydrogen atom, are reacted according to the methods that are known to one skilled in the art for the formation of large macrolides to compounds of formula I, in which T—Y has the meaning of O—C(=O). Preferred is the method that is described in "Reagents for Organic Synthesis, Vol. 16, p. 353" with use of 2,4,6-trichlorobenzoic acid chloride and suitable bases, such as, e.g., triethylamine, 4-dimethylaminopyridine, sodium hydride.

Step d (ABC→1)

Compounds ABC, in which $R^{13}$ represents a group $CH_2OH$ and $R^{20}$ represents a hydrogen atom, can be reacted preferably with use of triphenylphosphine and azodiesters, such as, for example, azodicarboxylic acid diethyl ester, to form compounds of formula I, in which T—Y has the meaning of O—$CH_2$.

Compounds ABC, in which $R^{13}$ represents a group $CH_2OSO_2$ alkyl or $CH_2OSO_2$ aryl or $CH_2OSO_2$ aralkyl and $R^{20}$ represents a hydrogen atom, can be cyclized to compounds of formula I, in which T—Y has the meaning of O—$CH_2$, after deprotonation with suitable bases, such as, for example, sodium hydride, n-butyllithium, 4-dimethylaminopyridine, Hünig base, alkylhexamethyldisilazanes.

As an alternative to the route above, partial fragments of general formula BC

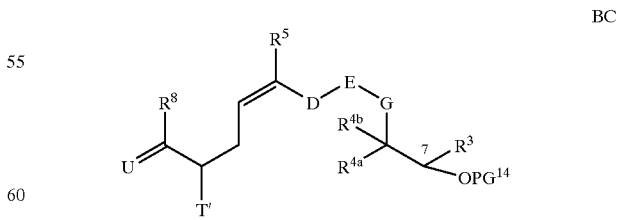

BC in which $R^3$, $R^{4a}$, $R^{4b}$, $R^5$, $R^8$, D, E, T' and U have the already mentioned meanings, and $PG^{14}$ represents a hydrogen atom or a protective group PG, can be obtained from the above-described fragments B and C according to the process that is shown in diagram 3.

Diagram 3
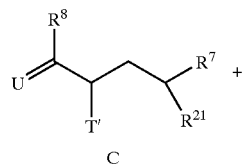
C
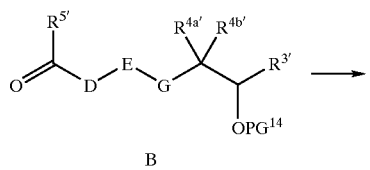
B
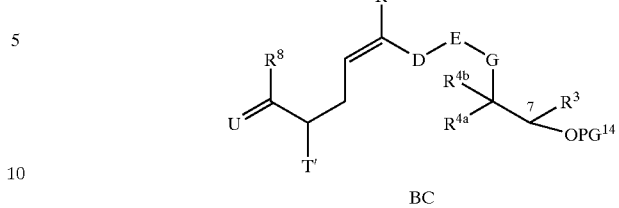
BC
To introduce a nitrogen group at C-15, the oxygen group can be converted directly (C''' or BC''' with T'=Nf=azide or a protected amine) or via the intermediate step of a halogen atom into a nitrogen group as desired in step C' (fragment C with T'=OR$^{20}$) or BC' (fragment BC with T'=OR$^{20}$) at position 15:
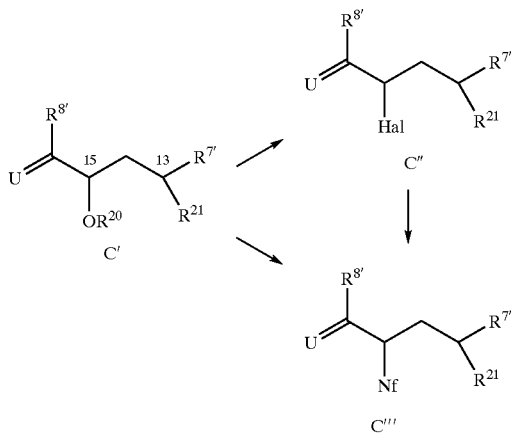
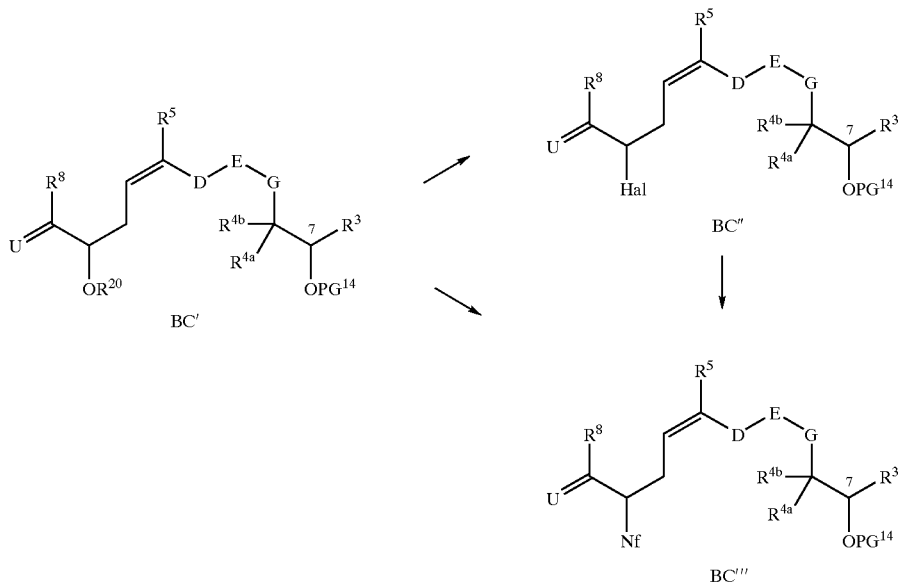

If $R^{20}$ represents a hydrogen, the hydroxyl group can be converted according to the processes that are known to one skilled in the art into a halogen atom, preferably a chlorine, bromine or iodine atom, which then is converted into a nitrogen group Nf, whereby Nf preferably represents an azide or a protected amine. As an alternative, the hydroxyl group at C-15 ($R^{20}$ in the meaning of hydrogen) can be converted into a leaving group, preferably into an alkyl- or aralkyl-sulfonate and the latter can be substituted by a nitrogen nucleophile Nf.

Partial fragments of general formula ABC

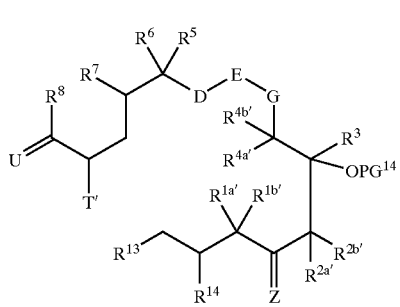

ABC in which $R^{1a'}$, $R^{1b'}$, $R^{2a'}$, $R^{2b'}$, $R^3$, $R^{4a'}$, $R^{4b'}$, $R^5$, $R^6$, $R^7$, $R^8$, $R^{13}$, $R^{14}$, D, E, G, T', U and Z have the already mentioned meanings, are obtained from the above-described fragments BC and A according to the process that is shown in Diagram 4.

Diagram 4

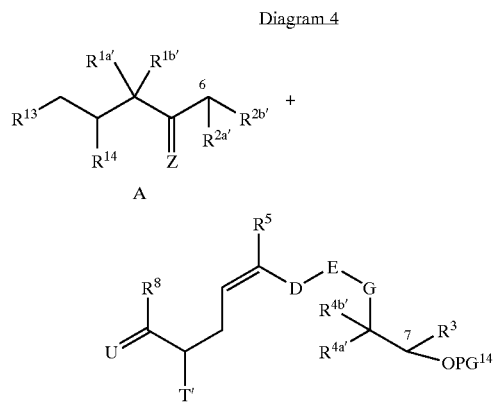

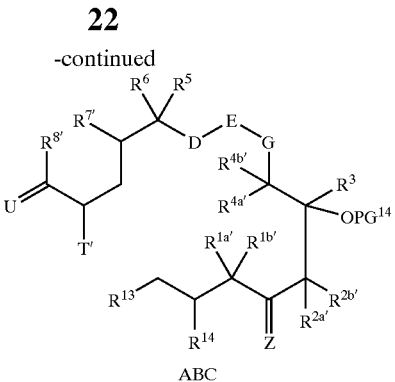

ABC

The introduction of the nitrogen group at C-15 can also take place in step ABC as already described for C''' or BC'''. The flexible functionalization of described components A, B, and C also ensures a linkage sequence that deviates from the above-described process and that leads to components ABC. These processes are listed in the following table:

| Possible Linkages | Linkage Methods a to e | Prerequisites |
|---|---|---|
| A + B → A - B | a: Aldol (see Diagram 1) | Z = W = oxygen |
| B + C → B - C | b: Wittig (analogously to Diagram 2) e: McMurry | U = oxygen and $R^{21}$ = Wittig salt or phosphine oxide or phosphonate U = V = oxygen |
| A + C → A - C | c: Esterification (e.g., 2,4,6-trichlorobenzoyl chloride/4-dimethylamino-pyridine) d: etherification (e.g., Mitsunobu) f: amide formation (e.g., with $(PhO)_2P(O)N_3$) in the presence of a base (e.g., $NaHCO_3$) in an inert solvent (e.g., DMF) | $R^{13} = CO_2R^{13b}$ or COHal and $R^{20}$ = hydrogen $R^{13} = CH_2OH$ and $R^{20}$ = hydrogen or $SO_2$—alkyl or $SO_2$—aryl or $SO_2$—aralkyl $R^{13} = CO_2R^{13b}$ or COHal and $R^{20}$ = hydrogen T = $NH_2$, $NHR^{24}$ |

According to these processes, components A, B and C, as indicated in Diagram 5, can be linked:

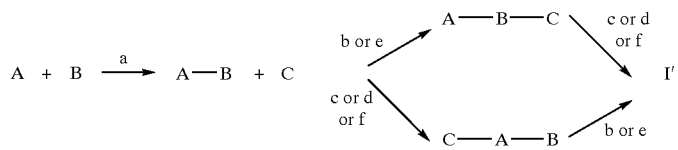

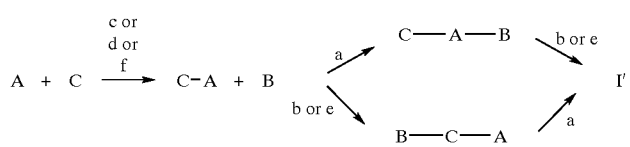

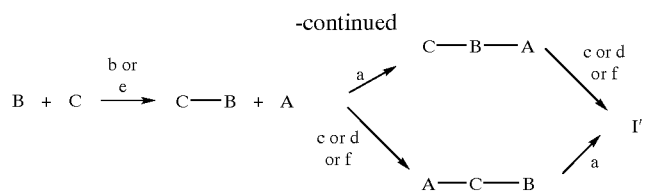

Free hydroxyl groups in I, I', A, B, C, AB, ABC can be further functionally modified by etherification or esterification, free carbonyl groups by ketalization, enol ether formation or reduction.

This invention relates to all stereoisomers of the described and claimed compounds and also their mixtures.

Biological Actions and Applications of the New Derivatives:

The new compounds of formula I are valuable pharmaceutical agents. They interact with tubulin by stabilizing microtubuli that are formed and are thus able to influence the cell-splitting in a phase-specific manner. This relates mainly to quick-growing, neoplastic cells, whose growth is largely unaffected by intercellular regulating mechanisms. Active ingredients of this type are in principle suitable for treating malignant tumors. As applications, there can be mentioned, for example, the therapy of ovarian, stomach, colon, adeno-, breast, lung, head and neck carcinomas, malignant melanoma, acute lymphocytic and myelocytic leukemia. The compounds according to the invention are suitable owing to their properties basically for anti-angiogenesis therapy as well as for treatment of chronic inflammatory diseases, such as, for example, psoriasis or arthritis. To avoid uncontrolled proliferation of cells and for better compatibility of medical implants, they can basically be applied or introduced into the polymer materials that are used for this purpose. The compounds according to the invention can be used alone or to achieve additive or synergistic actions in combination with other principles and classes of substances that can be used in tumor therapy.

As examples, there can be mentioned the combination with

Platinum complexes, such as, e.g., cis-platinum, carboplatinum, intercalating substances, e.g., from the class of anthracyclines, such as, e.g., doxorubicin or from the class of anthrapyrazoles, such as, e.g., Cl-941, substances that interact with tubulin, e.g., from the class of vinca-alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, DNA topoisomerase inhibitors, such as, e.g., camptothecin, etoposide, topotecan, teniposide, folate- or pyrimidine-antimetabolites, such as, e.g, lometrexol, gemcitubin, DNA-alkylating compounds, such as, e.g., adozelesin, dystamycin A, inhibitors of growth factors (e.g., of PDGF, EGF, TGFb, EGF), such as, e.g., somatostatin, suramin, bombesin antagonists, inhibitors of protein tyrosine kinases or protein kinases A or C, such as, e.g., erbstatin, genistein, staurosporine, ilmofosine, 8-Cl-cAMP, antihormones from the class of antigestagens, such as, e.g., mifepristone, onapristone or from the class of antiestrogens, such as, e.g., tamoxifen or from the class of antiandrogens, such as, e.g., cyproterone acetate, metastases-inhibiting compounds, e.g., from the class of eicosanoids, such as, e a., $PGI_2$, $PGE_1$, 6-oxo-$PGE_1$ as well as their more stable derivatives (e.g., iloprost, cicaprost, misoprostol), inhibitors of oncogenic RAS proteins, which influence the mitotic signal transduction, such as, for example, inhibitors of the farnesyl-protein-transferase, natural or synthetically produced antibodies, which are directed against factors or their receptors, which promote tumor growth, such as, for example, the erbB2 antibody.

In Vitro Activity of Epothilone Derivatives on Human Tumor Cell Lines a) $IC_{50}$ values [nM] for the growth inhibition of human MCF-7 breast- and multi-drug-resistant NCl/ADR carcinoma cell lines of the epothilone derivatives with 13Z-olefins in a crystal-violet assay in comparison to epothilone D.

TABLE 1

| Compound | MCF-7 | NCl/ADR | Selectivity* |
| --- | --- | --- | --- |
| Epothilone D | 23 | 50 | 2.2 |
| Taxol | 4.0 | >>100 | >>25 |
| Example 1 | 4.3 | 12 | 2.8 |
| Example 5 | 5.1 | 37 | 73 |
| Example 9 | 5.0 | 10 | 2.0 |
| Example 13 | 5.8 | 28 | 4.8 |
| Example 17 | 6.2. | 33 | 5.4 |

*Selectivity = $IC_{50}$ − (NCl/ADR): $IC_{50}$ (MCF-7)

The compounds of Examples 1, 9, 13 and 17 have a significantly higher active strength in comparison to structurally similar reference compound epothilone D. Unlike in taxol, all compounds show an action on the multi-drug-resistant cell line NCl/ADR.

b) $IC_{50}$ values [nM] for the growth inhibition of human MCF-7 breast- and multi-drug-resistant NCl/ADR carcinoma cell lines of the epothilone derivatives with 13,14-α-epoxide in a crystal-violet assay in comparison to epothilone B.

TABLE 2

| Compound | MCF-7 | NCl/ADR | Selectivity* |
| --- | --- | --- | --- |
| Epothilone B | 0.6 | 3.5 | 5.8 |
| Taxol | 4.0 | >>100 | >>25 |
| Example 3B | 0.3 | 1.4 | 4.7 |
| Example 7A | 0.8 | 6.0 | 7.5 |
| Example 10A | 2.1 | 3.9 | 1.9 |
| Example 14A | 0.5 | 3.5 | 7.0 |
| Example 20A | 0.6 | 4.6 | 7.6 |

*Selectivity = $IC_{50}$ − (NCl/ADR): $IC_{50}$ (MCF-7)

The compounds of Examples 3B, 14A, and 20A have a comparable or significantly higher active strength in comparison to structurally similar reference compound epothilone B. Unlike in taxol, all compounds show an action on the multi-drug-resistant cell line NCl/ADR. Compounds of Examples 3B and 10A show an improved selectivity in multi-drug-resistant cell line NCl/ADR in comparison to reference compound epothilone B.

The invention also relates to pharmaceutical agents that are based on pharmaceutically compatible compounds, i.e., compounds of general formula I that are nontoxic in the doses used, optionally together with commonly used adjuvants and vehicles.

According to methods of galenicals that are known in the art, the compounds according to the invention can be processed into pharmaceutical preparations for enteral, percutaneous, parenteral or local administration. They can be administered in the form of tablets, coated tablets, gel capsules, granulates, suppositories, implants, injectable, sterile, aqueous or oily solutions, suspensions or emulsions, ointments, creams and gels.

In this case, the active ingredient or ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, cleaning agents, dispersing agents, emulsifiers, preservatives and flavoring substances for taste correction (e.g., ethereal oils).

The compounds according to the invention can be present in the form of α-, β- or γ-cyclodextrin clathrates or can be encapsulated in liposomes.

The invention thus also relates to pharmaceutical compositions that as active ingredients contain at least one compound according to the invention. A dosage unit contains about 0.1–100 mg of active ingredient(s). In humans, the dosage of the compounds according to the invention is approximately 0.1–1000 mg per day.

The examples below are used for a more detailed explanation of the invention, without intending that it be limited to these examples.

EXAMPLES FOR THE PRODUCTION OF THE COMPOUNDS OF GENERAL FORMULA I ACCORDING TO THE INVENTION

Example 1

(4S,7R,8S,9S,13 (Z),16 S(Z))-4,8-Dihydroxy-16-(1-fluoro-2-(2-methyl-4-thiazolyl)ethenyl)-1-oxa-5,5,7,9,13-pentamethyl-cyclohexadec-13-ene-2,6-dione Analogously to the processes that are described in DE 19751200.3, 36.5 mg of the title compound is obtained from the phosphonium salt of Example 1j as a pale-yellow-colored oil.

$^1$H-NMR (DMSO-d6): δ=0.93 (3H), 0.94 (3H), 1.10 (3H), 0.8–1.4 (6H), 1.21 (3H), 1.62 (1H), 1.66 (3H), 1.87 (1H), 2.24 (1H), 2.3–2.6 (3H), 2.64 (3H), 2.73 (1H), 3.13 (1H), 3.53 (1H), 4.22 (1H), 5.16 (1H), 5.36 (1H), 6.22 (1H), 7.46 (1H) ppm.

Example 1a

2-Methylthiazole-4-carbaldehyde 476 ml of a 1.2 molar solution of DIBAH in toluene is slowly added in drops at −75° C. under nitrogen to a solution of 60 g of 2-methylthiazole-4-carboxylic acid ethyl ester in 1070 ml of methylene chloride. It is stirred for 2 more hours. Then, 150 ml of isopropanol and then 230 ml of water are slowly added in drops to it, the cold bath is removed, and it is stirred vigorously at 25° C. for 2 more hours. The precipitate that is produced is suctioned off and rewashed with ethyl acetate. The filtrate is concentrated by evaporation in a vacuum, and the residue that is thus obtained is purified by chromatography on silica gel. With hexane/ether 1:1, 35.6 g of the title compound is obtained as a colorless oil.

$^1$H-NMR (CDCl$_3$): δ=2.8 (3H), 8.05 (1H), 10.0 (1H) ppm.

Example 1b (2Z)-3-(2-Methylthiazol-4-yl)-2-fluoro-2-propenoic Acid Ethyl Ester

A solution of 58.7 g of phosphonofluoroacetic acid triethyl ester in 120 ml of dimethoxyethane is added at 0° C. to a suspension of 9.64 g of sodium hydride (60% suspension in mineral oil) in 120 ml of dimethoxyethane. It is stirred for 40 minutes, and then a solution of 15.4 g of the aldehyde, produced under Example 1a, in 120 ml of dimethoxyethane is added in drops and then stirred for 2 hours at 24° C. under argon. After the mixing with aqueous ammonium chloride solution, it is extracted three times with ethyl acetate, the organic phase is washed with dilute sodium chloride solution, dried on sodium sulfate and concentrated by evaporation in a vacuum. The mixture of the Z- and E-configured olefins is separated by column chromatography on silica gel. With hexane/ethyl acetate 4:6 to 3:7 and in addition to 3.9 g of a mixed fraction, 7.5 g of (2E)-3-(2-methylthiazol-4-yl)-2-fluoro-2-propenoic acid ethyl ester and 7.3 g of the title compound are obtained as colorless oils.

$^1$H-NMR (CDCl$_3$): δ=1.36 (3H), 2.73 (3H), 4.33 (2H), 7.20 (1H), 7.67 (1H) ppm.

Example 1c (2Z)-3-(2-Methylthiazol-4-yl)-2-fluoro-2-propen-1-ol 136 ml of a 1.2 molar solution of DIBAH in toluene is added in drops at −70° C. under nitrogen to a solution of 18.8 g of the above-produced ester in 260 ml of toluene. After one hour, 55 ml of isopropanol and then 68 ml of water are slowly added in drops to it, and it is stirred vigorously for 2 more hours. The precipitate that is produced is suctioned off and rewashed well with ethyl acetate. The filtrate is concentrated by evaporation in a vacuum, and the residue that is thus obtained is purified by chromatography on silica gel. With hexane/0–70% ethyl acetate, 13.4 g of the title compound is obtained as a colorless oil.

$^1$H-NMR (CDCl$_3$): δ=2.69 (3H), 3.71 (1H), 4.27 (2H), 6.18 (1H), 7.35 (1H) ppm.

Example 1d (2Z)-3-(2-Methylthiazol-4-yl)-2-fluoro-2-propenal

A total of 53.3 g of manganese dioxide is added in portions to a solution of 13.28 g of the above-produced alcohol in 200 ml of toluene, and it is stirred vigorously under nitrogen for 4 more hours. Manganese dioxide is suctioned off on Celite, washed well with ethyl acetate, and the filtrate is concentrated by evaporation in a vacuum. The residue that is thus obtained by chromatography on silica gel is purified. With hexane/0–30% ethyl acetate, 9.93 g of the title compound is obtained as a colorless oil.

$^1$H-NMR (CDCl$_3$): δ=2.77 (3H), 6.95 (1H), 7.88 (1H), 9.36 (1H) ppm.

Example 1e (3S,4Z)-5-(2-Methylthiazol-4-yl)-1-[(4S, 5R)-4-methyl-5-phenyl-1,3-1,3-oxazolidin-2-on-3-yl]-3-hydroxy-4-fluoro-4-penten-1-one 17.6 g of anhydrous chromium(II) chloride in 210 ml of THF under argon is introduced and mixed with 766 mg of lithium iodide. A solution of 9.8 g of the above-produced aldehyde and 18.8 g of (4S,5R)-3-(bromoacetyl)-4-methyl-5-phenyloxazolidin-2-one in 38 ml of THF is then added in drops to it. It is stirred for 3 more hours. 150 ml of saturated sodium chloride solution is added to it, it is stirred for 30 minutes, and the phases are separated. The aqueous phase is extracted twice with ethyl acetate, the combined organic phases are extracted once with water and once with saturated sodium chloride solution. The organic phase is dried on sodium sulfate, filtered off, and the filtrate is concentrated by evaporation in a vacuum. The residue that is thus obtained is purified by chromatography on silica gel. With hexane/0–60% ethyl acetate, 11.22 g of the title compound in addition to 9.53 g of a mixed fraction and 1.8 g of the corresponding diastereomeric title compound are obtained as light oils.

$^1$H-NMR (CDCl$_3$): δ=0.93 (3H), 2.71 (3H), 3.36 (1H), 3.52 (1H), 4.82 (1H), 5.72 (1H), 6.29 (1H), 7.2–7.5 (6H) ppm.

Example 1f (3S,4Z)-5-(2-Methylthiazol-4-yl)-1-[(4S,5R)-4-methyl-5-phenyl-1,3-1,3-oxazolidin-2-on-3-yl]-3-(tert-butyl-dimethylsilyloxy)-4-fluoro-4-penten-1-one 4.68 ml of lutidine is added in drops at −70° C. under nitrogen to a solution of 11.2 g of the above-produced title compound in 86 ml of methylene chloride, and it is stirred for 5 more minutes. Then, 8.56 ml of tert-butyldimethylsilyl-trifluoromethane sulfonate is slowly added in drops. After one hour, it is mixed with saturated ammonium chloride solution, and the reaction mixture is allowed to heat to 25° C. It is diluted with ether, washed once with water and once with saturated sodium chloride solution. The organic phase is dried on sodium sulfate and concentrated by evaporation in a vacuum. The residue that is thus obtained is purified by chromatography on silica gel. With hexane/ether 1:1, 9.3 g of the title compound is obtained as a colorless oil.

$^1$H-NMR (CDCl$_3$): δ=0.15 (6H), 0.90 (9H), 0.93 (3H), 2.70 (3H), 3.27 (1H), 3.57 (1H), 4.77 (1H), 4.90 (1H), 5.66 (1H), 6.15 (1H), 7.26–7.50 (6H) ppm.

Example 1g (3S,4Z)-5-(2-Methylthiazol-4-yl)-3-(tert-butyl-dimethylsiyloxy)-4-fluoro-4-pentenoic Acid Ethyl Ester 2.8 ml of titanium(IV) ethylate is added to a solution of 15.5 g of the above-produced title compound in 70 ml of ethanol, and it is refluxed for 4 hours under nitrogen. The reaction solution is concentrated by evaporation in a vacuum, the residue is taken up in 70 ml of ethyl acetate, mixed with water and stirred for 20 minutes. Titanium oxide is suctioned off, washed well with ethyl acetate, and the filtrate is concentrated by evaporation in a vacuum. The residue is mixed with hexane, the crystals are suctioned off and washed twice with hexane. The filtrate is concentrated by evaporation in a vacuum. The residue that is thus obtained is purified by chromatography on silica gel. With hexane/0–50% ethyl acetate, 11.9 g of the title compound is obtained as a colorless oil.

$^1$H-NMR (CDCl$_3$): δ=0.11 (6H), 0.91 (9H), 1.26 (3H), 2.70 (2H), 2.71 (3H), 4.15 (2H), 4.74 (1H), 6.12 (1H), 7.37 (1H) ppm.

Example 1h (3S,4Z)-5-(2-Methylthiazol-4-yl)-3-(tert-butyl-dimethylsilyloxy)-4-fluoro-4-penten-1-ol 58.6 ml of a 1.2 molar solution of DIBAH in toluene is slowly added in drops under nitrogen at −70° C. to a solution of 10.5 g of the above-produced title compound in 250 ml of toluene, and it is stirred for one hour at −30° C. 10 ml of isopropanol is slowly added in drops to it at −70° C., then 22 ml of water, and it is vigorously stirred at 25° C. for 2 more hours. The precipitate is suctioned off, washed well with ethyl acetate, and the filtrate is concentrated by evaporation in a vacuum. The residue that is thus obtained is purified by chromatography on silica gel. With hexane/0–70% ethyl acetate, 7.73 g of the title compound is obtained as a yellow oil.

$^1$H-NMR (CDCl$_3$): δ=0.12 (3H), 0.16 (3H), 0.93 (9H), 2.00 (2H), 2.72 (3H), 3.77 (1H), 3.86 (1H), 4.53 (1H), 6.13 (1H), 7.36 (1H) ppm.

Example 1i (3S,4Z)-5-(2-Methylthiazol-4-yl)-3-(tert-butyl-dimethylsilyloxy)-1-iodo-4-fluoro-4-petene 1.90 g of imidazole is added to a solution of 7.31 g of triphenylphosphine in 106 ml of methylene chloride. 7.07 g of iodine is added to this solution, allowed to stir for 10 minutes and then a solution of 7.7 g of the above-produced title compound in 28 ml of methylene chloride is added in drops and stirred for 30 minutes. It is filtered off, washed-well with ether, and the filtrate is concentrated by evaporation in a vacuum. The residue that is thus obtained is purified by chromatography on silica gel. With hexane/0–10% ethyl acetate, 8.2 g of the title compound is obtained as a colorless oil.

$^1$H-NMR (CDCl$_3$): δ=0.11 (3H), 0.16 (3H), 0.93 (9H), 2.23 (2H), 2.71 (3H), 3.24 (2H), 4.36 (1H), 6.12 (1H), 7.36 (1H) ppm.

Example 1j (3S,4Z)-5-(2-Methylthiazol-4-yl)-3-(tert-butyl-dimethylsilyloxy)-4-fluoro-4-pentene-triphenylphosphonium Iodide 8.16 g of the above-produced title compound is mixed with 5.33 g of triphenylphosphine and stirred under nitrogen at 100° C. for 2 hours. After cooling, the solid residue is pulverized twice with ether and a little ethyl acetate, whereby the supernatant solution is pipetted off. Then, the residue is dissolved in methanol and concentrated by evaporation in a vacuum. The solid foam is dissolved again in a little methanol, mixed with toluene and again concentrated by evaporation in a vacuum. This process is repeated twice, then the residue is dried under high vacuum. 12.4 g of the title compound is obtained as a solid substance.

Flash point: 70–72° C.

Example 2

(4S,7R,8S,9S,13(E),16S(Z))-4,8-Dihydroxy-16-(1-fluoro-2-(2-methyl-4-thiazolyl)ethenyl)-1-oxa-5,5,7,9,13-pentamethyl-cyclohexadec-13-ene-2,6-dione Analogously to Example 1, 41.5 mg of the title compound is obtained as a light yellow-colored oil from the phosphonium salt of Example 1j.

$^1$H-NMR (CDCl$_3$): δ=0.99 (3H), 1.05 (3H), 0.8–1.4 (6H), 1.16 (3H), 1.30 (3H), 1.5–1.7 (1H), 1.76 (1H), 2.00 (1H), 2.18 (1H), 2.43 (1H), 2.56 (1H), 2.63 (2H), 2.70 (3H), 3.25 (1H), 3.40 (2H), 3.66 (1H), 4.30 (1H), 5.13 (1H), 5.61 (1H), 6.18 (1H), 7.48 (1H) ppm.

Example 3

(1R,3S(Z),7S,10R,11S,12S,16S)-7,11-Dihydroxy-3-(1-fluoro-2-(2-methyl-4-thiazolyl)ethenyl)-8,8,10,12,16-pentamethyl-4,17-dioxabicyclo[14.1.0]heptadecane-5,9-dione (A) and (1S,3S(Z),7S,10R,11S,12S,16R)-7,11-dihydroxy-3-(1-fluoro-2-(2-methyl-4-thiazolyl)ethenyl)-8,8,10,12,16-pentamethyl-4,17-dioxabicyclo[14.1.0]heptadecane-5,9-dione (B)

0.172 ml of EDTA and 0.288 ml of 1,1,1-trifluoroacetone, then a mixture of 35.0 mg of oxone and 20.2 mg of sodium bicarbonate are added at 0° C. under argon to 15 mg of the title compound, produced in Example 1, in 0.3 ml of acetonitrile. It is stirred for 3.5 hours at 0° C. It is mixed with 2 ml of sodium thiosulfate solution, stirred for 5 minutes and diluted with 80 ml of ethyl acetate. The organic phase is washed once with semisaturated sodium chloride solution, dried on sodium sulfate and concentrated by evaporation in a vacuum. The residue that is thus obtained is purified by 2× preparative thick-layer chromatography. With methylene chloride/ethyl acetate 2:8 (1.PDC) or methylene chloride/methanol 98:2 (2.PDC), 2.5 mg of title compound A as a nonpolar component and 6 mg of title compound B as a polar component are obtained as colorless oils.

$^1$H-NMR (MeOH-d4) of A: δ=0.99 (3H), 1.04 (3H), 0.8–1.9 (11H), 1.30 (3H), 1.41 (3H), 2.17 (2H), 2.47 (1H), 2.58 (1H), 2.71 (3H), 3.01 (1H), 3.2–3.4 (1H), 3.78 (1H), 4.33 (1H), 4.8–5.0 (1H), 5.71 (1H), 6.26 (1H), 7.53 (1H) ppm.

$^1$H-NMR (MeOH-d4) of B: δ=0.99 (3H), 1.01 (3H), 0.9–1.9 (6H), 1.12 (3H), 1.30 (3H), 1.33 (3H), 1.95–2.10 (4H), 2.18 (2H), 2.41 (1H), 2.48 (1H), 2.70 (3H), 3.2–3.4 (1H), 3.63 (1H), 3.85 (1H), 4.34 (1H), 5.34 (1H), 5.63 (1H), 6.19 (1H), 7.51 (1H) ppm.

Example 4

(1R,3S(Z),7S,10R,11S,12S,16R)-7,11-Dihydroxy-3-(1-fluoro-2-(2-methyl-4-thiazolyl)ethenyl)-8,8,10,12,16-pentamethyl-4,17-dioxabicyclo[14.1.0]heptadecane-5,9-dione (A) and (1S,3S(Z),7S,10R,11S,12S,16S)-7,11-dihydroxy-3-(1-fluoro-2-(2-methyl-4-thiazolyl)ethenyl)-8,8,10,12,16-pentamethyl-4,17-dioxabicyclo[14.1.0]heptadecane-5,9-dione (B)

Analogously to Example 3, 8.8 mg of title compound A as a nonpolar component and 9.0 mg of title compound B as a polar component are obtained as colorless oils from 38 mg of the title compound that is produced in Example 2.

$^1$H-NMR (MeOH-d4) of A: δ=0.95 (3H), 1.00 (3H), 0.8–1.65 (8H), 1.14 (3H), 1.28 (3H), 1.33 (3H), 1.91 (1H), 2.18 (2H), 2.54 (2H), 2.68 (3H), 3.05 (1H), 3.43 (1H), 3.63 (1H), 4.26 (1H), 5.66 (1H), 6.24 (1H), 7.52 (1H) ppm.

$^1$H-NMR (MeOH-d4) of B: δ=0.95 (3H), 1.02 (3H), 0.8–1.7 (8H), 1.14 (3H), 1.29 (3H), 1.32 (3H), 1.77 (1H), 2.09 (1H), 2.23 (1H), 2.5–2.65 (2H), 2.69 (3H), 3.14 (1H), 3.33 (1H), 3.70 (1H), 4.38 (1H), 5.66 (1H), 6.21 (1H), 7.51 (1H) ppm.

Example 5

(4S,7R,8S,9S,13(Z),16S(Z))-4,8-Dihydroxy-16-(1-chloro-2-(2-methyl-4-thiazolyl)ethenyl)-1-oxa-5,5,7,9,13-pentamethyl-cyclohexadec-13-ene-2,6-dione Example 5a 2-Methylthiazol-4-carbaldehyde 50 g of ethyl-2-methylthiazole-4-carboxylate is dissolved in 700 ml of methylene chloride, cooled to −70° C. and carefully mixed with 390 ml of diisobutylaluminium hydride (1.2 molar in toluene). After 1 hour, the reaction was still not complete, and 40 ml of diisobutylaluminium hydride was added in drops once more. After another 40 minutes, the reaction mixture was carefully mixed with 100 ml of isopropanol and stirred for 15 minutes. Then, 215 ml of water is added in drops, and the cooling bath is removed. After 2 hours, the crystalline precipitate was suctioned off via a frit, washed with ethyl acetate, and the filtrate was concentrated by evaporation in a vacuum. 36.1 g of the title compound is obtained.

$^1$H-NMR (CDCl$_3$): δ=2.8 (3H), 8.05 (1H), 10.00 (1H) ppm.

Example 5b (2Z)-3-(2-Methylthiazol-4-yl)-2-chloro-2-propenoic Acid Ethyl Ester

A solution of 97 g of triethyl-2-chloro-2-phosphonoacetate in 165 ml of dimethoxyethane is added within 15 minutes at 0 ° C. under nitrogen to a suspension of 9 g of sodium hydride (60% suspension in mineral oil) in 165 ml of dimethoxyethane. It is stirred for 45 minutes at 24° C., and then a solution of 31.8 g of the title compound, produced under Example 5a, in 165 ml of dimethoxyethane is added in drops, and it is then stirred for 1 more hour. After mixing with aqueous ammonium chloride solution, it is extracted three times with ethyl acetate, the organic phase is washed with dilute sodium chloride solution, dried on sodium sulfate and concentrated by evaporation in a vacuum. The mixture of Z- and E-configured olefins is separated by column chromatography on silica gel. After column chromatography with hexane/ethyl acetate 10–30% and subsequent crystallization from hexane, 32 g of the title compound is obtained. (FP. 61° C.–62° C.)

$^1$H-NMR (CDCl$_3$): δ=1.37 (3H), 2.76 (3H), 4.33 (2H), 8.13 (1H), 8.18 (1H) ppm.

Example 5c (2Z)-3-(2-Methylthiazol-4-yl)-2-chloro-2-propen-1-ol

Analogously to Example 1c, 22.8 g of the title compound is obtained from 32 g of the ester, produced in Example 5b, in toluene as a solvent.

Example 5d (2Z)-3-(2-Methylthiazol-4-yl)-2-chloro-2-propenal 9.8 g of the alcohol that is produced in Example 5c is dissolved in 500 ml of methylene chloride and mixed with 26.14 ml of triethylamine. Then, 16.14 g of SO$_3$-pyridine complex is added, and it is stirred for 1 hour at 24° C. Now, it is mixed with ammonium chloride solution, extracted with ethyl acetate, the organic phase is washed with saturated sodium chloride solution and dried on sodium sulfate. After concentration by evaporation in a vacuum, 10.03 g of the title compound is obtained.

Example 5e (3S,4Z)-5-(2-Methylthiazol-4-yl)-1-[(4S,5R)-4-methyl-5-phenyl-1,3-oxazolidin-2-on-3-yl]-3-hydroxy-4chloro-4-penten-1-one Analogously to Example 1e, 1.4 g of the title compound is obtained from 3.3 g of the aldehyde that is produced in Example 5d.

$^1$H-NMR (CDCl$_3$): δ=0.95 (3H), 2.7 (3H), 3.38 (1H), 3.45–3.55 (1H), 3.56 (1H), 4.8 (1H), 4.89 (1H), 5.7 (1H), 7.18 (1H), 7.28–7.48 (5H), 7.83 (1H) ppm.

Example 5f (3S,4Z)-5-(2-Methylthiazol-4-yl)-1-[(4S,5R)-4-methyl-5-phenyl-oxazolidin-2-on-3-yl]-3-(tert-butyl-dimethylsilyloxy)-4-chloro-4-penten-1-one Analogously to Example 1f, 580 mg of the title compound is obtained from 1.4 g of the alcohol that is produced in Example 5e.

$^1$H-NMR (CDCl$_3$): δ=0.11 (3H), 0.15 (3H), 0.9 (9H), 0.85–0.95 (3H), 2.7 (3H), 3.26 (1H), 3.58 (1H), 4.77 (1H), 4.99 (1H), 5.64 (1H), 7.05 (1H), 7.25–7.46 (5H), 7.83 (1H) ppm.

Example 5g (3S,4Z)-5-(2-Methylthiazol-4-yl)-3-(tert-butyl-dimethylsilyloxy)-4-chloro-4-pentenoic Acid Ethyl Ester Analogously to Example 1g, 9.1 g of the title compound is obtained from 12.5 g of the silyl ether that is produced in Example 5f.

$^1$H-NMR (CDCl$_3$): δ=0.09 (3H), 0.1 (3H), 0.9 (9H), 1.26 (3H), 2.68–2.78 (2H), 2.72 (3H), 4.15 (2H), 4.82 (1H), 7.04 (1H), 7.8 (1H) ppm.

Example 5h (3S,4Z)-5-(2-Methylthiazol-4-y )-3-(tert-butyl-dimethylsilyloxy)-4-chloro-4-penten-1-ol Analogously to Example 1h, 7.5 g of the title compound is obtained from 9.1 g of the ethyl ester that is produced in Example 5g.

$^1$H-NMR (CDCl$_3$): δ=0.09 (3H), 0.14 (3H), 0.94 (9H), 1.92–2.12 (3H), 2.72 (3H), 3.68–3.88 (2H), 4.58 (1H), 7.04 (1H), 7.81 (1H) ppm.

Example 5i (3S,4Z)-5-(2-Methylthiazol-4-yl)-3-(tert-butyl-dimethylsilyloxy)-1-iodo-4-chloro-4-pentene Analogously to Example 1i, 2.02 g of the title compound is obtained from 1.7 g of the alcohol that is produced in Example 5h.

$^1$H-NMR (CDCl$_3$): δ=0.08 (3H), 0.14 (3H), 0.92 (9H), 2.1–2.33 (2H), 2.72 (3H), 3.2 (2H), 4.45 (1H), 7.03 (1H), 7.82 (1H) ppm.

Example 5j (3S,4Z)-5 (2-Methylthiazol-4-yl)-3-(tert-butyl-dimethylsilyloxy)-4-chloro-4-pentene-triphenylphosphonium Iodide Analogously to Example 1j, 14.8 g of the title compound is obtained from 9.6 g of the iodide that is produced in Example 5i.

$^1$H-NMR (CDCl$_3$): δ=0.1 (3H), 0.18 (3H), 0.9 (9H), 2.07 (2H), 2.69 (3H), 3.47–3.63 (1H), 3.68–3.85 (1H), 4.99 (1H), 7.21 (1H), 7.67–7.87 (16H) ppm.

Example 5k (2S,6E/Z,9S,10Z)-10-Chloro-9-[[dimethyl(1,1-dimethylethyl)silyl]oxy]-11-(2-methyl-4-thiazolyl)-2,6-dimethyl-undeca-6,10-dienol-tetrahydropyran-2-yl-ether 6.94 ml of butyllithium (1.6 molar in hexane) is carefully added in drops at 0° C. under nitrogen to a solution of 8 g of phosphonium salt, produced in Example 5j, in 22 ml of tetrahydrofuran, and it is stirred for 20 minutes (dark red solution). 1.69 g of (6S)-6-methyl-7-(tetrahydro-2H-pyran-2-yl(oxy)-heptan-2-one, disolved in 11 ml of tetrahydrofuran, was now added in drops to the reaction mixture. The reaction mixture was stirred for 30 more minutes and was then mixed with 11 ml of saturated ammonium chloride solution. After another 5 minutes, the reaction mixture was diluted with ethyl acetate, washed once with saturated sodium chloride solution, dried on sodium sulfate and concentrated by evaporation in a vacuum. After column chromatography with hexane/ether 0–50%, 4.8 g of the title compound is obtained.

$^1$H-NMR (CDCl$_3$): δ=0.05–0.1 (6H), 0.85–0.95 (12H), 1.0–2.52 (14H), 1.6 (3H), 2.7 (3H), 3.07–3.27 (1H), 3.42–3.54 (3H), 3.86 (1H), 4.26 (1H), 4.56 (1H), 5.12 (1H), 6.97 (1H), 7.81 (1H) ppm.

Example 5l (2S,6E/Z,9S,10Z)-10-Chloro-9-[[dimethyl(1,1-dimethylethyl)silyl]oxy]-11-(2-methyl-4-thiazolyl)-2,6-dimethyl-undeca-6,10-dienol 134.38 mg of pyridinium-p-toluenesulfonate is added to a solution of 2.9 g of the olefin, produced in Example 5k, in 40 ml of ethanol, and it is stirred for 6 hours at 55° C. under nitrogen. Then, it is concentrated by evaporation in a vacuum. After column chromatography with hexane/ethyl acetate 0–30%, 1.73 g of the title compound is obtained.

$^1$H-NMR (CDCl$_3$): δ=0.05–0.1 (6H), 0.92 (9H), 1.02/1.09 (3H), 1.59/1.61 (3H), 1.15–1.8 (4H), 1.93–2.08 (2H), 2.23–2.52 (3H), 2.72 (3H), 4.27 (1), 5.15 (1H), 6.95/6.98 (1H), 7.81 (1H), 9.54/9.6 (1H) ppm.

Example 5m (2S,6E/Z,9S,10Z)-10-Chloro-9-[[dimethyl(1,1-dimethylethyl)silyl]oxyl]-11-(2-methyl-4-thiazolyl)-2,6-dimethyl-undeca-6,10-dienal 2.28 ml of triethylamine is added at room temperature under nitrogen to a solution of 1.5 g of the alcohol, produced in Example 5l, in 32.7 ml of methylene chloride and 11 ml of dimethyl sulfoxide. Then, the reaction mixture is mixed with 1.042 g of SO$_3$-pyridine complex and stirred for 35 minutes. After saturated ammonium chloride solution is added, it is stirred for 5 more minutes, diluted with ether, washed with semisaturated sodium chloride solution, the organic phase is dried on sodium sulfate and concentrated by evaporation in a vacuum. 216 mg of the title compound is obtained.

Example 5n (3S,6R,7S,8S,12E/Z,15S,16Z)-16-Chloro-17-(2-methyl-4-thiazolyl)-5-oxo-1,3,15-tris[[dimethyl(1,1-dimethylethyl)silyl]oxy]-4,4,6,8,12-pentamethyl-heptadeca-12,16-dien-7-ol 3.3 ml of butyllithium (1.6 molar in hexane) is cooled to 0° C. and mixed carefully with a solution of 535 mg of diisopropylamine in 12 ml of tetrahydrofuran. Then, the reaction mixture is cooled to −70° C. and added in drops with a solution that consists of 1.78 g of (3S)-1,3-bis [[dimethyl(1,1-dimethylethyl)silyl]oxy]-4,4-dimethyl-heptan-5-one in 12 ml of tetrahydrofuran. It is stirred for 1 hour at a constant temperature. A solution of 1.34 g of the aldehyde, produced in Example 5m, in 9.7 ml of tetrahydrofuran, is now added in drops to the reaction mixture and stirred again for 1.5 hours. Then, it is mixed with saturated ammonium chloride solution, diluted with ether, washed twice with semisaturated sodium chloride solution, the organic phase is dried with sodium sulfate and concentrated by evaporation in a vacuum. After column chromatography with hexane/ethyl acetate 25%, 2.52 g of the title compound is obtained.

$^1$H-NMR (CDCl$_3$): δ=0.0–0.1 (18H), 0.77/0.81 (3H), 0.7–1.8 (8H), 0.85–0.9 (27H), 1.0 (3H), 1.07 (3H), 1.21 (3H), 1.58 (3H), 1.9–2.04 (2H), 2.34–2.47 (2H), 2.71 (3H), 3.28 (2H), 3.53–3.7 (2H), 3.88 (1H), 4.18–4.28 (1H), 5.11 (1H), 6.92 (1H), 7.79 (1H) ppm.

Example 5o (3S,6R,7S,8S,12E/Z,15S,16Z)-16-Chloro-17-(2-methyl-4-thiazolyl)-5-oxo-1,3,7,15-tetrakis [[dimethyl(1,1-dimethylethyl)silyl]oxy]-4,4,6,8,12-pentamethyl-heptadeca-12,16-diene 722 μl of lutidine is added in drops at 0° C. under nitrogen to a solution of 1.52 g of the alcohol, produced in Example 5n, dissolved in 21.3 ml of methylene chloride. After 5 minutes, 813 μl of tert-butyldimethylsilyltriflate is added to the reaction mixture, and it is stirred for 1.5 more hours. Then, it is diluted with ether, washed once with 1N hydrochloric acid, twice with saturated sodium chloride solution, the organic phase is dried with sodium sulfate and concentrated by evaporation in a vacuum. After column chromatography with hexane/ether 0–20%, 221 mg of the title compound is obtained.

Example 5p (3S,6R,7S,8S,12E/Z,15S,16Z)-16-Chloro-17-(2-methyl-4-thiazolyl)-5-oxo-3,7,15-tris[[dimethyl(1,1-dimethylethyl)silyl]oxy]-4,4,6,8,12-pentamethyl-heptadeca-12,16-dien-1-ol 453.45 mg of camphor-10-sulfonic acid is added at 0° C. under nitrogen to a solution that consists of 1.9 g of the silyl ether, produced in Example 5o, in 15 ml of methylene chloride and 15 ml of methanol, and it is stirred for 2 more hours. Then, it is mixed with 13 ml of triethylamine, and after 5 minutes, the reaction mixture is added to saturated sodium bicarbonate solution, diluted with methylene chloride, the organic phase is washed once with saturated sodium chloride solution, dried on sodium sulfate and concentrated by evaporation in a vacuum. 1.41 g of the title compound is obtained.

$^1$H-NMR (CDCl$_3$): δ=0.02–0.13 (18H), 0.85–0.96 (30H), 1.08 (3H), 1.23 (3H), 1.6 (3H), 1.0–2.1 (10H), 2.32–2.52 (2H), 2.72 (3H), 3.13 (1H), 3.65 (2H), 3.8 (1H), 4.08 (1H), 4.21–4.3 (1H), 5.13 (1H), 6.98 (1H), 7.8 (1H) ppm.

Example 5q (3S,6R,7S,8S,12E/Z,15S,16Z)-16-Chloro-17-(2-methyl-4-thiazolyl)-5-oxo-3,7,15-tris[[dimethyl(1,1-dimethylethyl)silyl]oxy]-4,4,6,8,12-pentamethyl-heptadeca-12,16-dienal 1.14 ml of triethylamine is added at room temperature under nitrogen to a solution that consists of 1.4 g of the alcohol, produced in Example 5p, in 19 ml of methylene chloride and 4.5 ml of dimethyl sulfoxide. Then, the reaction mixture is mixed with 520 mg of SO$_3$-pyridine complex and stirred for 2 hours. After saturated ammonium chloride solution is added, it is stirred for 5 minutes, diluted with ether, washed twice with semisaturated sodium chloride solution, the organic phase is dried on sodium sulfate and concentrated by evaporation in a vacuum. 1.44 g of the title compound is obtained.

Example 5r (3S,6R,7S,8S,12E/Z,15S,16Z)-16-Chloro-17-(2-methyl-4-thiazolyl)-5-oxo-3,7,15-tris[[dimethyl(1,1-dimethylethyl)silyl]oxy]-4,4,6,8,12-pentamethyl-heptadeca-12,16-dienoic Acid 1.89 ml of Jones reagent is added at −30° C. under nitrogen to a solution of 1.44 g of the aldehyde, produced in Example 5q, in 35 ml of acetone. After 45 minutes, the reaction mixture is mixed with 1.3 ml of isopropanol, stirred for 10 minutes, diluted with ether, washed three times with semisaturated sodium chloride solution, the organic phase is dried on sodium sulfate and concentrated by evaporation in a vacuum. After the crude product is purified by preparative thin-layer chromatography with hexane/ether 50% (run three times), 202 mg of the title compound is obtained.

$^1$H-NMR (CDCl$_3$): δ=0.03–0.16 (18H), 0.88–0.94 (30H), 1.09 (3H), 1.15 (3H), 1.18 (3H), 1.7 (3H), 1.0–2.44 (12H), 2.7 (3H), 3.15 (1H), 3.72 (1H), 4.32 (1H), 4.42 (1H), 5.19 (1H), 7.25 (1H), 7.87 (1H) ppm.

Example 5s (3S,6R,7S,8S,12E/Z,15S,16Z)-16-Chloro-17-(2-methyl-4-thiazolyl)-5-oxo-3,7-bis[[dimethyl(1,1-dimethlethyl)silyl]oxy]-15-hydroxy-4,4,6,8,12-pentamethyl-heptadeca-12,16-dienoic Acid 433.7 mg of tetrabutylammonium fluoride is added at room temperature under nitrogen to a solution of 22 mg of the carboxylic acid, produced in Example 5r, in 4.3 ml of tetrahydrofuran, and it is stirred for 1.5 more hours. Then, it is diluted with ethyl acetate, washed once with 0.5 N hydrochloric acid, twice with semisaturated sodium chloride solution, dried on sodium sulfate and concentrated by evaporation in a vacuum. After column chromatography with hexane/ethyl acetate 50%, 43 mg of the title compound is obtained.

$^1$H-NMR (CDCl$_3$): δ=0.03–0.17 (12H), 0.83–0.98 (21H), 1.08 (3H), 1.18 (6H), 1.1–2.6 (12H), 1.73 (3H), 1.95 (2H), 2.22 (2H), 2.71 (3H), 3.16 (1H), 3.77 (1H), 4.33 (1H), 4.42 (1H), 5.2 (1H), 7.29 (1H), 7.85 (1H) ppm.

Example 5t (A) (4S,7R,8S,9S,13(E),16S(Z))-4,8-Bis[[dimethyl (1,1-dimethylethyl)silyl]oxy]-16-(1-chloro-2-(2methyl-4-thiazolyl)ethenyl)-1oxa-5,5,7,9,13-pentamethyl-cyclohexadec-13-ene-2,6-dione (B) (4S,7R,8S,9S,13(Z),16S(Z))-4,8-bis[[dimethyl (1,1-dimethylethyl)silyl]oxy]-16-(1-choloro-2-(2-methyl-4-thiazolyl)ethenyl)-1-oxa-5,5,7,9,13-pentamethyl-cyclohexadec-13-ene-2,6-dione 72.7 μl of triethylamine is added at 0° C. under nitrogen to a solution of 180 mg of the alcohol, produced in Example 5s, in 3.4 ml of tetrahydrofuran. Then, 48.2 μl of 2,4,6- trichlorobenzoyl chloride is added, and it is stirred for one hour. This suspension is now added in drops over 3 hours with a metering pump to a solution that consists of 289.91 mg of 4-N,N-dimethylaminopyridine in 25.4 ml of toluene, and it is stirred for 1 hour. Then, the reaction mixture is concentrated by evaporation in a vacuum. After column chromatography with hexane/ethyl acetate 20% and subsequent purification using preparative thin-layer chromatography with methylene chloride/methanol 0.5%, 32 mg (E-compound) of title compound A and 81 mg (Z-compound) of title compound B are obtained.

$^{(B)1}$H-NMR (CDCl$_3$): δ=0.02–0.15 (12H), 0.85 (9H), 0.97 (9H), 0.9–2.95 (11H), 1.0 (3H), 1.1 (3H), 1.15 (3H), 1.27 (3H), 1.57 (3H), 2.71 (3H), 3.04 (1H), 3.9 (1H), 4.03 (1H), 5.13 (1H), 5.19 (1H), 7.06 (1H), 7.83 (1H) ppm.

Example 5

(4S,7R,8S,9S,13Z),16S(Z))-4,8-Dihydroxy-16-(1-chloro-2-(2-methyl-4-thiazolyl)ethenyl)-1-oxa-5,5,7,9,13-pentamethyl-cyclohexadec-13-ene-2,6-dione 702 µl of a 20% solution of trifluoroacetic acid in methylene chloride is added at −20° C. under nitrogen to a solution of 80 mg of title compound B, produced in Example 5t, in 314 µl of methylene chloride, and it is stirred for 5.5 more hours at 0° C. Then, the reaction mixture is concentrated by evaporation in a vacuum. After column chromatography with hexane/ethyl acetate 50%, 43.8 mg of the title compound is obtained.

$^1$H-NMR (DMSO-d$^6$, 100° C.): δ=0.94 (3H), 0.82–3.3 (14H), 1.11 (3H), 1.23 (6H), 1.67 (3H), 2.64 (3H), 3.58 (1H), 4.27 (1H), 5.16 (1H), 5.39 (1H), 7.06 (1H), 7.77 (1H) ppm.

Example 6

(4S,7R,8S,9S,13(E),16S(Z))-4,8-Dihydroxy-16-(1-chloro-2-(2-methyl-4-thiazolyl)ethenyl)-1-oxa-5,5,7,9,13-pentamethyl-cyclohexadec-13-ene-2,6-dione 395 µl of a 20% solution of trifluoroacetic acid in methylene chloride is added at −20° C. under nitrogen to a solution that consists of 45 mg of title compound A, produced in Example 5t, in 177 µl of methylene chloride, and it is stirred for 5.5 more hours at 0° C. Then the reaction mixture is concentrated by evaporation in a vacuum. After column chromatography with hexane/ethyl acetate 50%, 27 mg of the title compound is obtained.

$^1$H-NMR (DMSO-d$_6$, 100° C.): 0.8–2.7 (13H), 0.91 (3H), 1.11 (3H), 1.12 (6H), 1.6 (3H), 2.65 (3H), 3.25 (1H), 3.54 (1H), 4.46 (1H), 5.18 (1H), 5.44 (1H), 7.05 (1H), 7.83 (1H) ppm.

Example 7

(A) (1S,3S(Z),7S,10R,11S,12S,16R)-7,11-Dihydroxy-3-(1-chloro-2-(2-methyl-4-thiazolyl)ethenyl)-8,8,10,12,16-pentamethyl-4,17-dioxabicyclo[14.1.0]heptadecane-5,9-dione (B) (1R,3S(Z),7S,10R,11S,12S,16S)-7,11-dihydroxy 3-(1-chloro-2-(2-methyl-4-thiaxolyl)ethenyl)-8,8,10,12,16-pentamethyl-4,17-dioxabicyclo[14.1.0]heptadecane-5,9-dione 154.8 µg of ethylenediamine tetraacetic acid-di-sodium salt and 324.73 µg of 1,1,1-trifluoroacetone are added at 0° C. under nitrogen to a solution of 14 mg of the epothilone-D derivative, produced in Example 5, in 0.3 ml of acetonitrile. Then, 34.65 µg of oxone and 17.74 µg of sodium bicarbonate are added to the reaction mixture and stirred for 4 hours. Now, it is mixed with 2 ml of sodium thiosulfate solution, diluted with 100 ml of ethyl acetate, washed with semisaturated sodium chloride solution, dried on sodium sulfate andconcentrated by evaporation in a vacuum. After the crude product is purified using preparative thin-layer chromatography with methylene chloride/methanol 20%, 3.8 mg (polar) of A and 2.5 mg (nonpolar) of B of the title compound are obtained.

(A) $^1$H-NMR (MeOH-d$^4$): δ=0.8–2.6 (9H), 1.03 (3H), 1.2 (3H), 1.29 (6H), 1.33 (3H), 2.7 (3H), 2.93 (1H), 3.67 (1H), 4.23 (1H), 5.63 (1H), 7.12 (1H), 7.44 (1H) ppm.

Example 8

(A) (1S,3S(Z),7S,10R,11S,12S,16S)-7,11-Dihydroxy-3-(1-chloro-2-(2-methyl-4-thizolyl)ethenyl)-8,8,10,12,16-pentamethyl-4,17-dioxabicyclo[14.1.0]heptadecane-5,9-dione (B) (1R,3S(Z),7S,10R,11S,12S,16R)-7,11-dihydroxy-3-(1-chloro-2-(2-methyl-4-thiazolyl)ethenyl)-8,8,10,12,16-pentamethyl-4,17-dioxabicyclo[14.1.0]heptadecane-5,9-dione 154.8 µg of ethylenediaminetetraacetic acid-di-sodium salt and 324.73 µg of 1,1,1-trifluoroacetone are added at 0° C. under nitrogen to a solution that consists of 14 mg of the epothilone-D derivative, produced in Example 6, in 0.3 ml of acetonitrile. Then, 34.65 µg of oxone and 17.74 µg of sodium bicarbonate are added to the reaction mixture and stirred for 4 hours. Now, it is mixed with 2 ml of sodium thiosulfate solution, diluted with 100 ml of ethyl acetate, washed with semisaturated sodium chloride solution, dried on sodium sulfate and concentrated by evaporation in a vacuum. After the crude product is purified using preparative thin-layer chromatography with methylene chloride/methanol 20%, 6.8 mg (polar) of A and 3.4 mg (nonpolar) of B of the title compound are obtained.

Example 9

(4S,7R,8S,9S,13(Z),16S(Z))-4,8-Dihydroxy-16-(1-fluoro-2-(2-methyl-4-thiazolyl)ethenyl)-1-oxa-7,9,13-trimethyl-5,5-(1,3-trimethylene)cyclohexadec-13-ene-2,6-dione Analogously to Example 5, 235 mg of the title compound is obtained from 431 mg (0.585 mmol) of compound A that is described under 9j.

$^1$H-NMR (CDCl$_3$): δ=1.00 (3H), 1.27 (3H), 1.66 (3H), 2.70 (3H), 2.75–3.04 (3H), 3.43 (1H), 3.68 (1H), 4.42 (1H), 5.13 (1H), 5.37–5.46 (1H), 6.15–6.29 (1H), 7.36 (1H) ppm.

Example 9a (2S,6E/Z,9S,10Z)-9-[[Dimethyl(1,1-dimethylethyl)silyl]oxy]-10-fluoro-11-(2-methyl-4-thiazolyl)-2,6-dimethylundeca-6,10-dienol-tetrahydropyran-2-yl-ether Analogously to Example 5k, 3.52 g of the title compound is obtained from 2.47 g (10.8 mmol) of 6(S)-6-methyl-7-(tetrahydro-2H-pyran-2-yl(oxy))heptan-2-one (for production see: DE 19751200.3) and 11.4 g (16.2 mmol) of the compound that is described under Example 1j.

$^1$H-NMR (CDCl$_3$): δ=0.08 (6H), 0.85–0.95 (12H), 0.60+ 0.69 (3H), 2.37–2.50 (2H), 2.70 (3H), 3.10–3.30 (1H), 3.45–3.65 (2H), 3.82–3.92 (1H), 4.13–4.26 (1H), 4.57 (1 H), 5.14 (1H), 5.98–6.12 (1H), 7.33 (1H) ppm.

Example 9b (2S,6E/Z,9S,10Z)-9-[[Dimethyl(1,1-dimethylethyl) silyl]oxy]-10-fluoro-11-(2-methyl-4-thiazolyl)-2,6-dimethylundeca-6,10-dienol Analogously to Example 51, 2.81 g of the title compound is obtained from 3.52 g (6.70 mmol) of the compound that is described under 9a.

$^1$H-NMR (CDCl$_3$): δ=0.09 (6H), 0.87 (3H), 0.91 (9H), 1.58+1.69 (3H), 1.95–2.05 (2H), 2.35–2.52 (2H), 2.70 (3H), 3.38–3.55 (2H), 4.32 (1H), 5.14 (1H), 5.95–6.12 (1H), 7.34 (1H) ppm.

Example 9c (2S,6E/Z,9S,10Z)-9-[[Dimethyl(1,1-dimethylethyl) silyl]oxy]-10-fluoro-11-(2-methyl-4-thiazolyl)-2,6-dimethylundeca-6,10-dienal Analogously to Example 5m, 2.80 g of the title compound is obtained from 2.81 g (6.37 mmol) of the compound that is described under 9b.

$^1$-NMR (CDCl$_3$): δ=0.08 (6H), 0.90 (9H), 1.03–1.10 (3H), 1.58+1.67 (3H), 1.86 (1H), 1.95–2.11 (2H), 2.24–2.51 (3H), 2.70 (3H), 3.75 (1H), 4.15–4.27 (1H), 5.18 (1H), 5.97–6.14 (1H), 7.34 (1H), 9.55+9.59 (1H) ppm.

Example 9d (3S,6R,7S,8S,12E/Z,15S,16Z)-16-Fluoro-17-(2-methyl-4-thiazolyl)-5-oxo-6,8,12-trimethyl-4,4-(1,3-trimethylene)-1,3,15-tris[[dimethyl(1,1-dimethylethyl)silyl]oxy]heptadeca-12,16-dien-7-ol Analogously to Example 5n, 2.18 g of the title compound is obtained from 2.77 g (6.68 mmol) of (S)-1-(1,3-bis[[dimethyl(1,1-dimethylethyl)silyl]oxypropyl]cyclobutyl)-propan-1-one (for production see: DE 19751200.3) and 1.65 g (3.75 mmol) of the compound that is described under 9c.

$^1$H-NMR (CDCl$_3$): δ=0.04 (6H), 0.08 (6H), 0.15 (3H), 0.17 (3H), 0.79 (3H), 0.86–0.97 (27H), 1.03 (3H), 1.25–1.41 (2H), 1.59+1.68 (3H), 1.69–1.87 (4H), 1.90–2.09 (2H), 2.23–2.50 (4H), 2.70 (3H), 3.20–3.36 (2H), 3.58 (2H), 4.08–4.25 (2H), 5.14 (1H), 5.98–6.13 (1H), 7.33 (1H) ppm.

Example 9e (3S,6R,7S,8S,12E/Z,15S,16Z)-16-Fluoro-17-(2-methyl-4-thiazolyl)-5-oxo-1,3,7,15-tetrakis [[dimethyl(1,1-dimethylethyl)silyl]oxy]-6,8,12-trimethyl-4,4-(1,3-trimethylene)heptadeca-12,16-diene Analogously to Example 5o, 2.47 g of the title compound is obtained from 2.18 g (2.55 mmol) of the compound that is described under 9d.

$^1$-NMR (CDCl$_3$): δ=0.00–0.20 (24H), 0.85–1.00 (39H), 1.06 (3H), 1.48+1.67 (3H), 2.20–2.47 (4H), 2.72 (3H), 3.08 (1H), 3.59 (2H), 3.78 (1H), 4.10 (1H), 4.14–4.25 (2H), 5.15 (1H), 6.00–6.13 (1H), 7.35 (1H) ppm.

Example 9f (3S,6R,7S,8S,12E/Z,15S,16Z)-16-Fluoro-17-(2-methyl-4-thiazolyl)-5-oxo-6,8,12-trimethyl-4,4-(1,3-trimethylene)-3,7,15-tris[[dimethyl(1,1-dimethylethyl)silyl]oxy]heptadeca-12,16-dien-1-ol Analogously to Example 5p, 1.626 g of the title compound is obtained from 2.47 g (2.55 mmol) of the compound that is described under 9e.

$^1$H-NMR (CDCl$_3$): δ=0.03–0.13 (12H), 0.04–0.20 (6H), 0.86–1.03 (30H), 1.08 (3H), 1.59+1.68 (3H), 1.70–2.50 (10H), 2.72 (3H), 3.12 (1H), 3.64 (2H), 3.81 (1H), 4.08 (1H), 4.13–4.27 (1H), 5.15 (1H), 6.00–6.17 (1H), 7.35 (1H) ppm.

Example 9g (3S,6R,7S,8S,12E/Z,15S,16Z)-16-Fluoro-17-(2-methyl-4-thiazolyl)-5-oxo-6,8,12-trimethyl-4,4-(1,3-trimethylene)-3,7,15-tris[[dimethyl(1,1-dimethylethyl)silyl]oxy]heptadeca-12,16-dienal Analogously to Example 5q, 1.628 g of the title compound is obtained from 1.626 g (1.91 mmol) of the compound that is described under 9f.

$^1$H-NMR (CDCl$_3$): δ=0.02–0.12 (15H), 0.18 (3H), 0.85–1.00 (30H), 1.05–1.10 (3H), 1.59+1.68 (3H), 1.70–2.55 (10H), 2.71 (3H), 3.75 (1H), 4.12–4.25 (1H), 4.53 (1H), 5.17 (1H), 6.00–6.15 (1H), 7.33 (1H), 9.75 (1H) ppm.

Example 9h (3S,6R,7S,8S,12E/Z,15S,16Z)-16-Fluoro-17-(2-methyl-4-thiazolyl)-5-oxo-6,8,12-trimethyl-4,4-(1,3-trimethylene)-3,7,15-tris[[dimethyl(1,1-dimethylethyl)silyl]oxy]heptadeca-12,16-dienoic Acid Analogously to Example 5r, 1.161 g of the title compound is obtained from 1.628 g (1.91 mmol) of the-compound that is described under 9g.

$^1$H-NMR (CDCl$_3$): δ=0.02–0.15 (15H), 0.19 (3H), 0.84–1.00 (30H), 1.10–1.07 (3H), 1.56+1.69 (3H), 2.10–2.55 (10H), 2.70 (3H), 2.97–3.14 (1H), 3.78 (1H), 3.84 (1H), 4.09–4.27 (2H), 4.41+4.48 (1H), 5.10–5.23 (1H), 6.10+6.31 (1H), 7.37 (1H) ppm.

Example 9i (3S,6R,7S,8S,12E/Z,15S,16Z)-3,7-Bis[[dimethyl(1,1-dimethylethyl)silyl]oxy]-16-fluoro-15-hydroxy-17-(2-methyl-4-thiazolyl)-5-oxo-6,8,12-trimethyl-4,4,-(1,3-trimethylene)heptadeca-12,16-dienoic Acid Analogously to Example 5s, 1.01 g of the title compound is obtained from 1.161 g (1.34 mmol) of the compound that is described under 9h.

$^1$H-NMR (CDCl$_3$): δ=0.01–0.15 (9H), 0.17 (3H), 0.83–1.01 (21H), 1.07–1.15 (3H), 1.61+1.73 (3H), 2.07–2.60 (10H), 2.71 (3H), 2.92–3.11 (2H), 2.85 (1H), 3.80 (1H),.4.18–4.30 (1H), 4.40+4.48 (1H), 5.11–5.22 (1H), 6.19+6.37 (1H), 7.37 (1H) ppm.

Example 9j 4S,7R,8S,9S,13(Z),16S(Z)-4,8-Bis[[dimethyl(1,1-dimethylethyl)silyl]oxy]-16-(1fluoro-2-(2-methyl-4-thiazolyl)ethenyl-1-oxa-7,9,13-trimethyl-5,5-(1,3-trimethylene)cyclohexa-dec-13-ene-2,6-dione (A) and 4S,7R,8S,9S,13(E),16S(Z)-4,8-Bis[[dimethyl(1, 1-dimethylethyl)silyl]oxy]-16-(1fluoro-2-(2-methyl-4-thiazolyl)ethenyl-1-oxa-7,9,13-trimethyl-5,5-(1,3-trimethylene)cyclohexa-dec-13-ene-2,6-dione (B)

Analogously to Example 5t, 434 mg of title compound A and 395 mg of title compound B are obtained from 1.01 g (1.34 mmol) of the compound that is described under 9i.

$^1$H-NMR (CDCl$_3$) of A: δ=−0.07 (3H), 0.07–0.20 (9H), 0.80 (9H), 0.93 (9H), 0.98 (3H), 1.22 (3H), 1.68 (3H), 1.80–1.90 (1H) 2.00–2.10 (1H), 2.20–2.50 (4H), 2.60–2.68 (4H), 2.72 (3H), 2.76–3.00 (2H), 3.92 (1H), 4.41 (1H), 5.08–5.12 (2H), 6.08–6.22 (1H), 7.38 (1H) ppm.

$^1$H-NMR (CDCl$_3$) of B: δ=0.02 (3H), 0.07 (3H), 0.11 (3H), 0.14 (3H), 0.90 (9H), 0.93 (9H), 1.02 (3H), 1.25 (3H), 1.51 (3H), 1.70–2.15 (8H), 2.30–2.60 (4H), 2.72 (3H), 2.77–2.93 (2H), 4.19 (1H), 4.59 (1H), 5.10 (1H), 5.42 (1H), 6.09–6.23 (1H), 7.36 (1H) ppm.

Example 10

(1S,3S,(Z),7S,10R,11S,12S,16R)-7,11-Dihydroxy-3-((1-fluoro)-2-(2-methyl-4-thazolyl)ethenyl)-10,12,16-trimethyl-8,8-(1,3-trimethylene)-4,17-dioxabicyclo[14.1.0]hepta-deca-5,9-dione (A) and (1R,3S(Z),7S,10R,11S,12S,16S)-7,11-dihydroxy-3-((1-fluoro)-2-(2-methyl-4-thazolyl)ethenyl)-10,12,16-trimethyl-8,8-(1,3-trimethylene)-4,17-dioxabicyclo[14.1.0]hepta-deca-5,9-dione (B)

Analogously to Example 7, 31 mg of title compound A and 7 mg of title compound B are obtained from 50 mg (0.098 mmol) of the compound that is described under Example 9.

$^1$H-NMR (CDCl$_3$) of A: δ=0.99 (3H), 1.25 (3H), 1.28 (3H), 2.71 (3H), 2.81 (1H), 3.02–3.12 (1H), 3.62–3.77 (2H), 4.40 (1H), 5.56–5.68 (1H), 6.17–6.81 (1H), 7.37 (1H) ppm.

$^1$H-NMR (CDCl$_3$) of B: δ=0.92 (3H), 1.20 (3H), 1.38 (3H), 2.75(3H), 3.00 (1H), 3.11 (1H), 3.86 (1H), 4.42 (1H), 5.29 (1H), 6.26–6.39 (1H), 7.41 (1H) ppm.

Example 11

(4S,7R,8S,9S,13(Z),16S(Z))-4,8-Dihydroxy-16-((1-fluoro-2-(2-methyl-4-thazolyl)ethenyl)-1-oxa-7,9,13-trimethyl-5,5-(1,3-trimethylene)cyclohexadec-13-ene-2,6-dione Analogously to Example 5t, 200 mg of the title compound is obtained from 395 mg (0.54 mmol) of compound B that is described under 9j.

$^1$H-NMR (CDCl$_3$): δ=1.00 (3H), 1.25 (3H), 1.54 (3H), 2.69 (1H), 2.97–3.08 (1H), 3.63 (1H), 4.44 (1H), 5.09 (1H), 5.54–5.63 (1H), 6.11–6.25 (1H), 7.38 (1H) ppm.

Example 12

(1S,3S(Z),7S,10R,11S,12S,16S)-7,11-Dihydroxy-3-((1-fluoro)-2-(2-methyl-4-thazolyl)ethenyl)-10,12,16-trimethyl-8,8-(1,3-trimethylene)-4,17-dioxabicyclo[14.1.0]heptadeca-5,9-dione (A) and (1R,3S(Z),7S,10R,11S,12S,16R)-7,11-dihydroxy-3-(1-fluoro)-2-(2-methyl-4-thazolyl)ethenyl)-10,12,16-trimethyl-8,8-(1,3-trimethylene)-4,17-dioxabicyclo[14.1.0]heptadeca-5,9-dione (B)

Analogously to Example 7, 41 mg of title compound A and 36 mg of title compound B are obtained from 100 mg (0.197 mmol) of the compound that is described under Example 11.

$^1$H-NMR (CDCl$_3$) of A: δ=0.93 (3H), 1.19 (3H), 1.22 (3H), 2.70 (3H), 2.88 (1H), 3.11 (1H), 3.19 (1H), 3.65 (1H), 3.72 (1H), 4.45 (1H), 5.61–5.72 (1H), 6.12–6.26 (1H), 7.37 (1H) ppm.

$^1$H-NMR (CDCl$_3$) of B: δ=0.98 (3H), 1.22–1.27 (6H), 2.72 (3H), 2.93 (1H), 3.07–3.17 (1H), 3.30 (1H), 3.67 (1H), 3.85 (1H), 4.40 (1H), 5.68–5.77 (1H), 6.22–6.36 (1H), 7.41 (1H) ppm.

Example 13

(4S,7R,8S,9S,13(Z),16S(Z))-4,8-Dihydroxy-9,13-dimethyl-7-ethyl-16-(1-fluoro-2-(2-methyl-4-thiazolyl)ethenyl)-1-oxa-5,5-(1,3-trimethylene)cyclohexadec-13-ene-2,6-dione Analogously to Example 5, 181 mg of the title compound is obtained from 400 mg (0.534 mmol) of the compound that is described under 13g.

$^1$H-NMR (CDCl$_3$): δ=0.94 (3H), 1.01 (3H), 1.69 (3H), 2.68–2.82 (1H), 2.71 (3H), 2.96 (1H), 3.38 (1H), 3.68 (1H), 4.42 (1H), 5.10 (1H), 5.42 (1H), 6.13–6.27 (1H), 7.37 (1H) ppm.

Example 13a (3S,6R,7S,8S,12E/Z,15S,16Z)-8,12-Dimethyl-6-ethyl-16-fluoro-17-(2-methyl-4-thiazolyl)-5-oxo-4,4-(1,3-trimethylene)-1,3,15-tris[[dimethyl(1,1-dimethlethyl)silyl]oxy]heptadeca-12,16-dien-7-ol Analogously to Example 5n, 2.042 g of the title compound is obtained from 2.975 g (6.937 mmol) of (S)-1-(1,3-bis[[dimethyl(1,1-dimethylethyl)silyl]oxypropyl]-cyclobutyl)-butan-1-one (For production see: DE 19751200.3) and 1.695 g (3.854 mmol) of the compound that is described under 9c.

$^1$H-NMR (CDCl$_3$): δ=0.01–0.20 (18H), 0.84–1.00 (33H), 1.60+1.69 (3H), 2.69 (3H), 3.11 (1H), 3.22 (1H), 3.40 (1H), 3.62 (2H), 4.06–4.25 (2H), 5.97–6.12 (1H), 7.34 (1H) ppm.

Example 13b (3S,6R,7S,8S,12E/Z,15S,16Z)-8,12-Dimethyl-6-ethyl-16-fluoro-17-(2-methyl-4-thiazolyl)-5-oxo-1,3,7,15-tetrakis[[dimethyl(1,1-dimethyl)silyl]oxy]-4,4-(1,3-trimethylene)heptadeca-12,16-diene Analogously to Example 5o, 2.311 g of the title compound is obtained from 2.042 g (2.351 mmol) of the compound that is described under 13a.

$^1$H-NMR (CDCl$_3$): δ=0.00–0.20 (24H), 0.80–0.99 (42H), 1.60+1.68 (3H), 2.70 (3H), 3.02 (1H), 3.60 (2H), 3.86 (1H), 4.04–4.25 (2H), 5.97–6.13 (1H), 7.32 (1H) ppm.

Example 13c (3S,6R,7S,8S,12E/Z,15S,16Z)-8,12-Dimethyl-6-ethyl-16-fluoro-17-(2-methyl-4-thiazolyl)-5-oxo-4,4 (1,3-trimethylene)3,7,15-tris[[dimethyl(1,1-dimethylethyl)silyl]oxy]heptadeca-12,16-dien-1-ol Analogously to Example 5p, 1.593 g of the title compound is obtained from 2.311 g (2.351 mmol) of the compound that is described under 13b.

$^1$H-NMR (CDCl$_3$): δ=0.02–0.19 (18H), 0.80–0.99 (33H), 1.57 (3H) +1.67 (3H), 2.70. (3H), 3.04 (1H), 3.60–3.71 (2H), 3.87 (1H), 4.04–4.25 (2H), 5.13 (1H), 5.95–6.11 (1H), 7.33 (1H) ppm.

Example 13d (3S,6R,7S,8S,12E/Z,15S,16Z)-8,12-Dimethyl-6-ethyl-16-fluoro-17-(2-methyl-4-thiazolyl)-5-oxo-4,4 (1,3-trimethylene)3,7,15-tris[[dimethyl(1,1-dimethylethyl)silyl]oxy]heptadeca-12,16-dienal Analogously to Example 5q, 1.589 g of the title compound is obtained from 1.593 g (1.834 mmol) of the compound that is described under 13c.

¹H-NMR (CDCl₃): δ=0.04–0.20 (18H), 0.82–1.00 (33H), 1.58 (3H) +1.68 (3H), 2.71 (3H), 3.04 (1H), 3.86 (1H), 4.19 (1H), 4.55 (1H), 5.17 (1H), 5.98–6.12 (1H), 7.33 (1H), 9.79 (1H) ppm.

Example 13e (3S,6R,7S,8S,12Z,15S,-16Z)-8,12-Dimethyl-6-ethyl-16-fluoro-17-(2-methyl-4-thiazolyl)-5-oxo-4,4(1,3-trimethylene)3,7,15-tris[[dimethyl(1,1-dimethylethyl)silyl]oxy]hepta-deca-12,16-dienoic Acid (A) and (3S,6R,7S,8S,12E,15S,16Z)-8,12-dimethyl-6-ethyl-16-fluoro-17-(2-methyl-4-thiazolyl)-5-oxo-4,4-(1,3-trimethylene)-3,7,15-tris[[dimethyl(1,1-dimethylethyl)silyl]oxy]hepta-deca-12,16-dienoic Acid (B)

Analogously to Example 5r, 664 mg of title compound A and 566 mg of title compound B are obtained from 1.589 g (1.834 mmol) of the compound that is described under 13d.

¹H-NMR (CDCl₃) of A: δ=0.00 (3H),0.07–0.09 (9H), 0.12 (3H), 0.19 (3H), 0.86–1.03 (33H), 1.70 (3H), 2.70 (3H), 2.90 (1H), 3.73 (1H), 4.21 (1H), 4.48 (1H), 5.21 (1H), 6.38–6.52 (1H), 7.38 (1H) ppm.

¹H-NMR (CDCl₃) of B: δ=0.00 (3H), 0.05 (3H), 0.07 (3H), 0.09 (3H), 0.15 (3H), 0.20 (3H), 0.84–0.99 (33H), 1.56 (3H), 2.69 (3H), 2.98 (1H), 3.87, (1H), 4.40 (1H), 5.12 (1H), 6.07–6.22 (1H), 7.38 (1H) ppm.

Example 13f (3S,6R,7S,8S,12Z,15S,16Z)-3,7-Bis[[dimethyl(1,1-dimethylethyl)silyl]oxy]-8,12-dimethyl-6-ethyl-16-fluoro-15-hydroxy-17-(2-methyl-4-thiazolyl)-5-oxo-4,4-(1,3-trimethylene)heptadeca-12,16-dienoic Acid Analogously to Example 5s, 578 mg of the title compound is obtained from 663 mg (0.752 mmol) of compound A that is described under 13e.

¹H-NMR (CDCl₃): δ=0.03 (3H), 0.06 (3H), 0.09 (3H), 0.17 (3H), 0.85–1.00 (24H), 1.75 (3H), 2.17 (3H), 2.89 (1H), 3.78 (1H), 4.25 (1H), 4.49 (1H), 5.21 (1H), 6.43–6.57 (1H), 7.39 (1H) ppm.

Example 13g 4S,7R,8S,9S,13(Z),16S(Z)-4,8-Bis[[dimethyl(1,1-dimethylethyl)silyl]oxy]-9,13-dimethyl-7-ethyl-16-(1-fluoro-2-(2-methyl-4-thiazolyl)ethenyl)-1-oxa-5,5-(1,3-trimethylene)cyclohexadec-13-ene-2,6-dione Analogously to Example 5t, 400 mg of the title compound is obtained from 578 mg (0.752 mmol) of the compound that is described under 13f.

¹H-NMR (CDCl₃): δ=–0.09 (3H), 0.09 (3H), 0.15 (3H), 0.17 (3H), 0.80–0.97 (21H), 1.00 (3H), 1.68 (3H), 2.70 (3H), 2.75–2.88 (1H), 2.98 (1H), 4.04 (1H), 4.42 (I), 5.17 (3H), 6.07–6.20 (1H), 7.37 (1H) ppm.

Example 14

(1S,3S(Z),7S,10R,11S, 12S,16R)-7,11-Dihydroxy-12,16-dimethyl-10-ethyl-3-(1-fluoro-2-(2-methyl-4-thiazolyl)ethenyl)-8,8-(1,3- trimethylene)-4,17-dioxabicyclo[14.1.0]hepta-decane-5,9-dione (A) and (1R,3S(Z),7S,10R,11S,12S,16S)-7,11-dihydroxy-12, 16-dimethyl-10-ethyl-3-(1-fluoro-2-(2-methyl-4-thiazolyl)ethenyl)-8,8-(1,3-trimethylene)-4,17-dioxabicyclo[14.1.0]hepta-decane-5,9-dione (B)

Analogously to Example 7, 26 mg of title compound A and 6 mg of title compound B are obtained from 40 mg (0.0767 mmol) of the compound that is described under Example 13.

¹H-NMR (CDCl₃) of A: δ=0.95 (3H), 0.98 (3H), 1.29 (3H), 2.71 (3H), 2.78 (1H), 3.03 (1H), 3.67 (1H), 4.40 (1H), 5.66 (1H), 6.16–6.79 (1H), 7.38 (1H) ppm.

¹H-NMR (CDCl₃) of B: δ=0.95–1.00 (6H), 1.26 (3H), 2.70 (3H), 2.91 (1H), 2.95–3.05 (2H), 3.34 (1H), 3.73 (1H), 4.48 (1H), 5.73 (1H), 6.22–6.35 (1H), 7.40 (1H) ppm.

Example 15

(4S,7R,8S,9S,13(E),16S(Z))-4,8-Dihydroxy-9,13-dimethyl-7-ethyl-16-(1-fluoro-2-(2-methyl-4-thiazolyl)ethenyl)-1-oxa-5,5-(1,3-trimethylene)cyclohexadec-13-ene-2,6-dione Analogously to Example 5, 214 mg of the title compound is obtained from 433 mg (0.5778 mmol) of the compound that is described under 15b.

¹H-NMR (CDCl₃): δ=0.94 (3H), 1.02 (3H), 1.54 (3H), 2.61–2.74 (1H), 2.68 (3H), 3.08 (1H), 3.73 (1H), 3.98 (2H), 4.52 (1H), 5.09 (1H), 5.54 (1H), 6.06–6.20 (1H), 7.37 (1H) ppm.

Example 15a (3S,6R,7S,8S,12E,15S,16Z)-3,7-Bis[[dimethyl(1,1-dimethylethyl)silyl]oxy]-8,12-dimethyl-6-ethyl-16-fluoro-15hydroxy-17-(2-methyl-4-thiazolyl)-5-oxo-4,4-(1,3-trimethylene)heptadeca-12,16-dienoic Acid Analogously to Example 5s, 493 mg of the title compound is obtained from 566 mg (0.642 mmol) of compound B that is described under 13e.

¹H-NMR (CDCl₃): δ=0.01 (3H), 0.04 (3H), 0.09 (3H), 0.17 (3H), 0.82–0.95 (24H), 1.62 (3H), 2.68 (3H), 2.95 (3H), 3.82 (1H), 4.17–4.30 (1H), 4.40 (1H), 5.15 (1H), 6.15–6.28 (1H), 7.37 (1H) ppm.

Example 15b 4S,7R,8S,9S,13(E),16S(Z)-4,8-Bis[[dimethyl(1,1-dimethylethyl)silyl]oxy]-9,13-dimethyl-7-ethyl-16-(1-fluoro-2-(2-methyl-4-thiazolyl)ethenyl)-1-oxa-5,5-(1,3-trimethylene)cyclohexadec-13-ene-2,6-dione Analogously to Example 5t, 433 mg of the title compound is obtained from 493 mg (0.642 mmol) of the compound that is described under 15a.

¹H-NMR (CDCl₃): δ=0.07 (3H), 0.10 (3H), 0.12 (3H), 0.15 (3H), 0.85–1.04 (24H), 2.71 (3H), 2.92 (1H), 4.06 (1H), 5.15 (1H), 5.36–5.47 (1H), 6.10–6.23 (1H), 7.37 (1H) ppm.

Example 16

(1S,3S(Z)7S,10R,11S,12S,16S)-7,11-Dihydroxy-12,16-dimethyl10-ethyl-3-(1-fluoro-2-(2-methyl-4-thiazolyl)ethenyl)-8,8-(1,3-trimethylene)-4,17-dioxabicyclo[14.1.0]heptadecane-5,9-dione (A) and (1R,3S(Z),7S,10R,11S,12S,16R)-7,11-dihydroxy-12,16-dimethyl-10-ethyl-3-(1-fluoro-2-(2-methyl-4-thiazolyl)ethenyl)-8,8-(1,3-trimethylene)-4,17-dioxabicyclo[14.1.0]heptadecane-5,9-dione (B)

Analogously to Example 7, 40 mg of title compound A and 39 mg of title compound B are obtained from 100 mg (0.1917 mmol) of the compound that is described under Example 15.

¹H-NMR (CDCl₃) of A: δ=0.94 (3H), 0.96 (3H), 1.27 (3H), 2.68 (3H), 2.90 (2H), 3.08 (1H), 3.59 (1H), 3.77 (1H), 5.67 (1H) 6.11–6.24 (1H), 7.37 (1H) ppm.

¹H-NMR (CDCl₃) of B: δ=0.89–1.00 (6H), 1.24 (3H), 2.67 (3H), 2.89 (1H), 3.11 (1H), 3.47 (1H), 3.68–3.81 (2H), 4.46 (1H), 5.68 (1H), 6.19–6.32 (1H), 7.38 (1H) ppm.

Example 17

(4S,7R,8S,9S,13Z,16S(Z))-4,8-Dihydroxy-16-(1-fluoro-2-(2-pyridyl)ethenyl)-7-ethyl-1-oxa-5,5,9,13-tetramethyl-cyclohexadec-13-ene-2,6-dione

Example 17a

2-Pyridyl-carbaldehyde

The solution of 50 ml (370 mmol) of 2-picolinic acid ethyl ester in 1 l of anhydrous dichloromethane is cooled under an atmosphere of dry argon to −78° C., mixed with 500 ml of a 1.2 molar solution of diisobutylaluminum hydride in toluene and stirred for one more hour. It is mixed with 152 ml of isopropanol, 253 ml of water, allowed to heat to 23° C. and stirred until a fine-grained precipitate has formed. After filtration and removal of the solvent, 32.6 g (304 mmol, 82%) of the title compound is isolated as a pale yellow oil.

¹H-NMR (CDCl₃):δ=7.52 (1H), 7.89 (1H), 7.99 (1H), 8.80 (1H), 10.10 (1H) ppm.

Example 17b (2E/Z)-3-(2-Pyridyl)-2-fluoro-2-propenoic Acid Ethyl Ester

The solution of 115 g of 2-fluoro-2-phosphonoacetic acid triethyl ester in 230 ml of ethylene glycol dimethyl ether is added in drops under an atmosphere of dry argon at 0° C. to 20.7 g of a 55% sodium hydride dispersion in 230 ml of anhydrous ethylene glycol dimethyl ether, and it is stirred for one more hour. Then, it is mixed with the solution of 27.6 g (258 mmol) of the title compound, presented according to Example 17a, in 230 ml of ethylene glycol dimethyl ether, and it is allowed to heat within one hour to 23° C. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is purified by vacuum distillation. 33.7 g (173 mmol, 67%) of the title compounds is isolated as a colorless oil.

¹H-NMR (CDCl₃): δ=1.22+1.39 (3H), 4.25+4.37 (2H), 6.90–7.13 (1H), 7.23+7.26 (1H), 756+7.90 (1H), 7.67+7.76 (1H), 8.59+8.67 (1H) ppm.

Example 17c (2Z)-3-(2-Pyridyl)-2-fluoro-2-propenoic Acid Ethyl Ester

The solution of 29.2 g (149 mmol) of the E/Z mixture, presented according to Example 17b, in 280 ml of anhydrous toluene is mixed under an atmosphere of dry argon with 2.0 g of iodine, and it is heated for seven days to 100° C. The cooled solution is washed with saturated sodium thiosulfate solution and dried on sodium sulfate. The residue that is obtained after filtration and removal of the solvent is purified by chromatography on about 1 l of fine silica gel with a gradient system that consists of n-hexane and ethyl acetate. 26.3 g (135 mmol, 90%) of the title compound is isolated as a colorless oil.

¹H-NMR (CDCl₃): δ=1.39 (3H), 4.37 (2H), 7.13 (1H), 7.26 (1H), 7.76 (1H), 7.90 (1H), 8.67 (1H) ppm.

Example 17d (2Z)-3-(2-Pyridyl)-2-fluoro-2-propen-1-ol

The solution of 26.3 (135 mmol) of the compound, presented according to Example 17c, in 800 ml of anhydrous tetrahydrofuran is cooled under an atmosphere of dry argon to −78° C., mixed with 80 g of lithium-tri-tert-butoxyaluminium hydride, allowed to heat to 23° C. and stirred for 16 hours. It is mixed with water, extracted several times with ethyl acetate, the combined organic extracts are washed with saturated sodium chloride solution and dried on sodium sulfate. The residue that is obtained after filtration and removal of the solvent is purified by chromatography on about 1.5 l of fine silica gel with a gradient system that consists of n-hexane and ethyl acetate. 17.3 g (113 mmol, 84%) of the title compound is isolated as a colorless oil.

¹H-NMR (CDCl₃): δ=1.93 (1H), 4.32 (2H), 6.19 (1H), 7.16 (1H), 7.69 (1H), 7.77 (1H), 8.52 (1H) ppm.

Example 17e (2Z)-3-(2-Pyridyl)-2-fluoro-2-propenal

The solution of 17.3 g (113 mmol) of the compound, presented according to Example 17d, in 2.5 l of anhydrous toluene is mixed with 100 g of manganese dioxide, and it is stirred for 16 hours at 23° C. It is filtered on Celite, and 13.8 g (91 mmol, 81%) of the title compound is isolated as a pale yellow oil.

¹H-NMR (CDCl₃): δ=6.87 (1H), 7.32 (1H), 7.81 (1H), 7.99 (1H), 8.72 (1H), 9.43 (1H) ppm.

Example 17f (3S,4Z)-5-(2-Pyridyl)-1-[(4S,5R)-4-methyl-5-phenyl-1,3-oxazolidin-2-on-3-yl]-3-hydroxy-4-fluoro-4-penten-1-one (A) and (3R,4Z)-5-(2-pyridyl)-1-[(4S,5R)-4-methyl-5-phenyl-1,3-oxazolidin-2-on-3-yl]-3-hydroxy-4-fluoro-4-penten-1-one (B)

50 ml of a 2.4 molar solution of n-butyllithium in n-hexane is added in drops at −30° C. under an atmosphere of dry argon to the solution of 16.8 ml of diisopropylamine in 800 ml of anhydrous tetrahydrofuran, stirred for 20 minutes, cooled to −70° C. and mixed within 4 hours with the solution of 23.6 g of (4S,5R)-3-acetyl-4-methyl-5-phenyloxazolidin-2-one in 800 ml of tetrahydrofuran. After 1 hour, the solution of 10.3 g (68 mmol) of the title compound, presented according to Example 17e, in 390 ml of tetrahydrofuran is added in drops within 2 hours, and it is stirred for 16 hours at −70° C. It is poured onto a saturated ammonium chloride solution, extracted several times with ethyl acetate, the combined organic extracts are washed with saturated sodium chloride solution and dried on sodium sulfate. The residue that is obtained after filtration and removal of the solvent is separated by repeated chromatography on fine silica gel with a gradient system that consists of n-hexane, ethyl acetate and ethanol. 8.60 g (23.2 mmol, 34%) of title compound A is isolated as a crystalline solid, and 5.04 g (13.6 mmol, 20%) of title compound B is isolated as a colorless foam.

¹H-NMR (CDCl₃) of A: δ=0.94 (3H), 3.38 (1H), 3.56 (1H), 4.83 (1H), 4.89 (1H), 5.70 (1H), 6.33 (1H), 7.14 (1H), 7.23–7.48 (5H), 7.68 (1H), 7.76 (1H), 8.58 (1H) ppm.

¹H-NMR (CDCl₃) of B: δ=0.94 (3H), 3.47 (2H), 4.19 (1H), 4.81 (1H), 4.89 (1H), 5.72 (1H), 6.29 (1H), 7.16 (1H), 7.22–7.49 (5H), 7.69 (1H), 7.76 (1H), 8.59 (1H) ppm.

Example 17g (4Z)-5-(2-Pyridyl)-1-[(4S,5R)-4-methyl-5-phenyl-1, 3-oxazolidin-2-on-3-yl]-4-fluoro-4-penten-1,3-dione Analogously to Example 17e, 3.54 g (9.56 mmol) of compound B that is presented according to Example 17f is reacted, and after working-up, 3.01 g (8.17 mmol, 85%) of the title compound is isolated as a crystalline solid.

$^1$H-NMR (CDCl$_3$) as a ketone/enol mixture: δ=0.97 (3H), 4.39+7.17+13.19 (2H), 4.88 (1H), 5.72+5.76 (1H, 6.99+7.07 (1H), 7.20–7.50 (6H), 7.57+7.78 (1H), 7.91 (1H), 8.65+8.70 (1H) ppm.

Example 17h (3S,4Z)-5-(2-Pyridyl)-1-[(4S,5R)-4-methyl-5-phenyl-1,3-oxazolidin-2-on-3-yl]-3-hydroxy-4-fluoro-4-penten-1-one (A) and (3R,4Z)-5-(2-pyridyl)-1-[(4S,5R)-4-methyl-5-phenyl-1,3-oxazolidin-2-on-3-yl]-3-hydroxy-4-fluoro-4-penten-1-one (B)

The solution of 12.2 g (33.1 mmol) of the compound, presented according to Example 17g, in a mixture of 610 ml of anhydrous dichloromethane and 65 ml of anhydrous methanol is mixed under an atmosphere of dry argon at –40° C. with 732 mg of sodium borohydride, and it is stirred for 1 hour. It is poured into a saturated sodium bicarbonate solution, extracted several times with dichloromethane, and the combined organic extracts are dried on sodium sulfate. The residue that is obtained after filtration and removal of the solvent is separated by chromatography on fine silica gel with a gradient system that consists of dichloromethane and ethanol. In addition to starting material, 3.46 g (9.3 mmol, 28%) of title compound A and 3.38 g (9.1 mmol, 28%) of title compound B, which in each case are identical to the compounds that are described under Example 17f, are isolated.

Example 17i (3S,4Z)-5-(2-Pyridyl)-1-[(4S,5R)-4-methyl-5-phenyl-1,3-oxazolidin-2-on-3-yl]-3-[[dimethyl(1,1-dimethylethyl)silyl]oxy]-4-fluoro-4-penten-1-one The solution of 9.96 g (26.89 mmol) of compound A, presented according to Example 17f and/or 1h, in 85 ml of anhydrous dichloromethane, is cooled under an atmosphere of dry argon to –70° C., mixed with 7 ml of 2,6-lutidine, 12.4 ml of trifluoromethanesulfonic acid-tert-butyldimethylsilylester, and it is stirred for 2 hours. It is poured onto a saturated sodium bicarbonate solution, extracted several times with dichloromethane, the combined organic extracts are washed with saturated sodium chloride solution and dried on sodium sulfate. The residue that is obtained after filtration and removal of the solvent is separated by chromatography on fine silica gel with a gradient system that consists of n-hexane, ethyl acetate and ethanol. 12.9 g (26.6 mmol, 99%) of the title compound is isolated as a colorless oil.

$^1$H-NMR (CDCl$_3$): δ=0.16 (6H), 0.90 (12H), 3.29 (1H), 3.59 (1H), 4.78 (1H), 4.92 (1H), 5.67 (1H), 6.12 (1H), 7.13 (1H), 7.24–7.47 (5H), 7.68 (1H), 7.76 (1H), 8.58 (1H) ppm.

Example 17j (3S,4Z)-5-(2-Pyridyl)-3-[[dimethyl(1,1-dimethylethyl)silyl]oxy]-4-fluoro-4-pentenoic Acid Ethyl Ester The solution of 12.8 g (26.5 mmol) of the compound, presented according to Example 17i, in 130 ml of anhydrous ethanol is mixed at 23° C. under an atmosphere of dry argon with 6.7 ml of titanium tetraethylate, and it is heated for 2 hours to 85° C. It is concentrated by evaporation, and the residue is purified by chromatography on fine silica gel with a gradient system that consists of n-hexane and ethyl acetate. 9.3 g (26.3 mmol, 99%) of the title compound is isolated as a colorless oil.

$^1$H-NMR (CDCl$_3$): δ=0.12 (6H), 0.91 (9H), 1.28 (3H), 2.72 (2H), 4.17 (2H), 4.77 (1H), 6.09 (1H), 7.15 (1H), 7.68 (1H), 7.73 (1H), 8.59 (1H) ppm.

Example 17k (3S,4Z)-5-(2-Pyridyl)-3-[[dimethyl (1,1-dimethylethyl)silyl]oxy]-4-fluoro-4-penten-1-ol Analogously to Example 17a, 9.7 g (27.4 mmol) of the title compound that is presented according to Example 17j is reacted, and after working-up and purification, 6.8 g (21.8 mmol, 80%) of the title compound is isolated as a colorless oil.

$^1$H-NMR (CDCl$_3$): δ=0.12 (3H), 0.14 (3H), 0.93 (9H), 1.83 (1H), 2.00 (2H), 3.78 (1H), 3.85 (1H), 4.53 (1H), 6.09 (1H), 7.12 (1H), 7.65 (1H), 7.72 (1H), 8.57 (1H) ppm.

Example 17l (3S,4Z)-5-(2-Pyridyl)-3-[[dimethyl(1,1-dimethylethyl)silyl]oxy]-1-iodo-4-fluoro-4-pentene The solution of 6.75 g of triphenylphosphine in 120 ml of anhydrous dichloromethane is mixed at 23° C. under an atmosphere of dry argon with 1.78 g of imidazole, 6.47 g of iodine, and the solution of 6.8 g (21.8 mmol) of the compound, presented according to Example 17k, in 40 ml of dichloromethane is added in drops while being cooled. It is stirred for 1 hour and purified directly by chromatography on fine silica gel with a gradient system that consists of n-hexane and ethyl acetate. 6.7 g (15.9 mmol, 73%) of the title compound is isolated as a colorless oil.

$^1$H-NMR (CDCl$_3$): δ=0.13 (3H), 0.19 (3H), 0.93 (9H), 2.25 (2H), 3.28 (2H), 4.38 (1H), 6.09 (1H), 7.17 (1H), 7.69 (1H), 7.75 (1H), 8.58 (1H) ppm.

Example 17m (3S,4Z)-5-(2-Pyridyl)-3-[[dimethyl(1,1-dimethylethyl)silyl]oxy]-4-fluoro-4-penten-1-triphenylphosphonium Iodide 6.7 g (15.9 mmol) of the compound that is presented according to Example 17l is mixed with 8.4 ml of ethyldiisopropylamine, 50.3 g of triphenylphosphine, and it is heated for 4 hours to 85° C. The oily residue is purified by chromatography on fine silica gel with a gradient system that consists of n-hexane and ethyl acetate. 8.9 g (13.0 mmol, 82%) of the title compound is isolated as a crystalline solid.

$^1$H-NMR (CDCl$_3$): δ=0.16 (3H), 0.22 (3H), 0.90 (9H), 2.01 (1H), 2.18 (1H), 3.50 (1H), 4.07 (1H), 4.90 (1H), 6.19 (1H), 7.12 (1H), 7.59–7.88 (17H), 8.54 (1H) ppm.

Example 17n (2S, 6E/Z,9S,10Z)-9-[[Dimethyl(1,1-dimethylethyl) silyl]oxy]-10-fluoro-11-(2-pyridyl)-1-(tetrahydropyran-2-yloxy)-2,6-dimethyl-undeca-6, 10-diene The suspension of 3.32 g (4.86 mmol) of the compound, presented according to Example 17m, in 22 ml of anhydrous tetrahydrofuran is mixed at 0° C. under an atmosphere of dry argon with 4.86 ml of a 1 M solution of sodium-bis-(trimethylsilyl)-amide in tetrahydrofuran. The solution of 753 mg (3.30 mmol) of (2S)-2-methyl-6-oxo-heptane-1-(tetrahydropyran-2-yloxy), which was produced analogously to the processes described in DE 197 51 200.3, in 22 ml of tetrahydrofuran, is slowly added in drops to the red solution, allowed to stir for 3 hours, poured onto saturated ammonium chloride solution and extracted several times with ethyl acetate. The combined organic extracts are dried on sodium sulfate and concentrated by evaporation in a vacuum. After column chromatography on silica gel with a gradient system that consists of n-hexane and ethyl acetate, in addition 1.30 g (2.57 mmol, 78%) of the title compound is obtained as a colorless foam.

$^1$H-NMR (CDCl$_3$): δ=0.10 (6H), 0.83–0.96 (12H), 1.10 (1H), 1.20–2.07 (12H), 1.60+1.68 (3H), 2.43 (2H), 3.04–3.27 (1H), 3.42–3.63 (2H), 3.85 (1H), 4.22 (1H), 4.57 (1H), 5.19 (1H), 6.04 (1H), 7.13 (1H), 7.68 (1H), 7.76 (1H), 8.57 (1H) ppm.

Example 17o (2S,6E/Z,9S,10Z)-9-[[Dimethyl(1,1-dimethylethyl)silyl]oxy]-10-fluoro-11-(2-pyridyl)-1-hydroxy-2,6-dimethyl-undeca-6,10-diene 700 mg of pyridinium-p-toluenesulfonate is added to a solution of 1.30 g (2.57 mmol) of the compound, produced according to Example 17n, in 50 ml of ethanol, and it is stirred for 3 hours at 23° C. Then, it is concentrated by evaporation in a vacuum, and the residue that is thus obtained is purified by chromatography on silica gel with a gradient system that consists of n-hexane and ethyl acetate. 832 mg (1.97 mmol, 77%) of the title compound is isolated as a colorless oil.

$^1$H-NMR (CDCl$_3$): δ=0.11 (6H), 0.88+0.91 (3H), 0.95 (9H), 1.07 (1H), 1.24–1.71 (5H), 1.60+1.69 (3H), 1.92–2.11 (2H), 2.34–2.58 (2H), 3.34–3.54 (2H), 4.24 (1H), 5.19 (1H), 6.00+6.02 (1H), 7.12 (1H), 7.66 (1H), 7.76 (1H), 8.56 (1H) ppm.

Example 17p (2S,6E/Z,9S,10Z)-9-[[Dimethyl(1,1-dimethylethyl)silyl]oxy]-10-fluoro-11-(2-pyridyl)-2,6-dimethyl-undeca-6,10-dienal 971 μl of dimethyl sulfoxide is carefully added in drops under nitrogen at −70° C. to 598 μl of oxalyl chloride, dissolved in 25 ml of dichloromethane, and it is stirred for 10 minutes at this temperature. Then, a solution of 1.45 g (3.44 mmol) of the, alcohol, produced according to Example 17o, in 25 ml of dichloromethane is added, and it is stirred for 0.5 hour between −60° C. and −70° C. Then, 2.84 ml of triethylamine is added, and after 1 hour of stirring at −60° C., the reaction mixture is added to 30 ml of water. After phase separation, the aqueous phase is extracted several times with dichloromethane. The combined organic phases are washed with saturated sodium chloride solution. After drying on sodium sulfate and filtration, it is concentrated by evaporation in a vacuum. The residue is purified by chromatography on fine silica gel with a gradient system that consists of n-hexane and ethyl acetate. 1.31 g (3.12 mmol, 91%) of the title compound is obtained as a colorless oil.

Example 17q (4S(4R,5S,6S,10E/Z,13S,14Z))-4-(13-[[(1,1-Dimethylethyl)dimethylsilyl]oxy]-4-ethyl-14-fluoro-15-(2-pyridyl)-3-oxo-5-hydroxy-2,6,10-trimethyl-pentadeca-10,14dien-2-yl)-2,2-dimethyl-[1,3]dioxane (A) and (4S(4S,5R,6S,10E/Z,13S,14z))-4 (13-[[(1,1-dimethyethyl)dimethylsilyl]oxy]-4-ethyl-14-fluoro-15-(2-pyridyl)-3-oxo-5-hydroxy-2,6,10-trimethyl-pentadeca-10,14dien-2-yl)-2,2-dimethyl-[1,3]dioxane (B)

The solution of 1.57 ml of diisopropylamine in 40 ml of anhydrous tetrahydrofuran is cooled under an atmosphere of dry argon to −30° C., mixed with 4.72 ml of a 2.4 molar solution of n-butyllithium in n-hexane, and it is stirred for 30 more minutes. At −78° C., the solution of 1.31 g (3.12 mmol) of the compound, presented according to Example 17p, in 40 ml of tetrahydrofuran is added in drops and allowed to react for 1 hour. Then, it is mixed with the solution of 2.36 9 (10.3 mmol) of (4S)-4-(2-methyl-3oxo-hex-2-yl)-2,2-dimethyl-[1,3]dioxane, which was produced according to the process described in DE 19751200.3, in 40 ml of tetrahydrofuran, and after 60 minutes, it is poured into a saturated ammonium chloride solution. It is diluted with water, extracted several times with ethyl acetate, the combined organic extracts are washed with saturated sodium chloride solution, dried on sodium sulfate and concentrated by evaporation in a vacuum. After column chromatography on silica gel with a gradient system that consists of n-hexane and ethyl acetate, in addition to starting material, 1.56 g (2.41 mmol, 77%) of title compound A and 287 mg (0.44 mmol, 14%) of title compound B are obtained.

$^1$H-NMR (CDCl$_3$) of A: δ=0.09 (6H), 0.81 (3H), 0.85 (3H), 0.92 (9H), 1.00 (3H), 1.08 (1H), 1.18–1.83 (8H), 1.26 (3H), 1.32 (3H), 1.39 (3H), 1.60+1.68 (3H), 1.88–2.08 (2H), 2.32–2.52 (2H), 2.87+2.91 (1H), 3.19 (1H), 3.44 (1H), 3.87 (1H), 3.98 (1H), 4.16 (1H), 4.22 (1H), 5.18 (1H), 6.00 (1H), 7.11 (1H), 7.65 (1H), 7.73 (1H), 8.56 (1H) ppm.

Example 17r (3S,6R,7S,8S,12E/Z,15S,16Z)-15-[[(1,1-Dimethylethyl)dimethylsilyl]oxy]-6-ethyl-16-fluoro-1,3,7-trihydroxy-4,4,8,12-tetramethyl-17-(2pyridyl)-heptadeca-12,16-dien-5-one The solution of 1.45 g (2.24 mmol) of the compound, presented according to Example 17q, in 36 ml of anhydrous ethanol is mixed under an atmosphere of dry argon with 1.06 g of pyridinium-p-toluenesulfonate, and it is stirred for 4 hours at 23° C. After removal of the solvent, the residue is chromatographed on fine silica gel with a mixture that consists of n-hexane and ethyl acetate. 1.36 g (2.24 mmol, 93%) of the title compound is isolated as a colorless oil.

$^1$H-NMR (CDCl$_3$): δ=0.10 (6H), 0.78–0.90 (6H), 0.92 (9H), 0.99–2.12 (11H), 1.08 (3H), 1.26 (3H), 1.58+1.68 (3H), 2.32–2.53 (2H), 2.79–3.03 (2H), 3.19 (1H), 3.41 (1H), 3.73–3.93 (3H), 4.06–4.25 (2H), 5.13+5.21 (1H), 5.93 (1H), 7.13 (1H), 7.67 (1H), 7.77 (1H), 8.58 (1H) ppm.

Example 17s (3S,6R,7S,8S,12E/Z,15S,16Z)-6-Ethyl-1,3,7,15-tetrakis-[[(1,1-dimethylethyl)dimethylsilyl]oxy]-16-fluoro-4,4,8,12-tetramethyl-17-(2-pyridyl)-heptadeca-12,16-dien-5-one The solution of 1.36 g (2.24 mmol) of the compound, presented according to Example 17r, in ml of anhydrous dichloromethane is cooled under an atmosphere of dry argon to −78° C., mixed with 3.45 ml of 2,6-lutidine, 3.36 ml of trifluoromethanesulfonic acid-tert-butyl dimethyl silyl ester, allowed to heat within 2 hours to 0° C. and stirred for 2 more hours. It is poured into saturated sodium bicarbonate solution and extracted several times with dichloromethane. The combined organic extracts are dried on sodium sulfate and concentrated by evaporation in a vacuum. After column chromatography on silica gel with a gradient system that consists of n-hexane and ethyl acetate, 1.83 g (1.92 mmol, 86%) of the title compound is isolated as a colorless oil.

$^1$H-NMR (CDCl$_3$): δ=0.00–0.12 (24H), 0.83 (3H), 0.85–0.98 (39H), 1.00–1.82 (9H), 1.03 (3H), 1.21 (3H), 1.61+1.68 (3H), 1.98 (2H), 2.42 (2H), 3.01 (1H), 3.47–3.73 (2H), 3.82 (1H), 3.91 (1H), 4.21 (1H), 5.19 (1H), 6.01 (1H), 7.12 (1H), 7.65 (1H), 7.73 (1H), 8.58 (1H) ppm.

Example 17t (3S,6R,7S,8S,12E/Z,15S,16Z)-6-Ethyl-3,7,15-tris-[[(1,1-dimethylethyl)dimethylsilyl]oxy]-1-hydroxy-16-fluor-4,4,8,12-tetramethyl-17-(2-pyridyl)-heptadeca-12,16-dien-5-one The solution of 1.83 g (1.92 mmol) of the compound, presented according to Example 17s, in a mixture of 20 ml of dichloromethane and 20 ml of methanol is mixed at 23° C. under an atmosphere of dry argon with 446 mg of campher-10-sulfonic acid, and it is stirred for 2 hours. It is poured into a saturated sodium bicarbonate solution and extracted several times with dichloromethane. The combined organic extracts are dried on sodium sulfate and concentrated by evaporation in a vacuum. After column chromatography on fine silica gel with a gradient system that consists of n-hexane and ethyl acetate, 1.40 g (1.67 mmol, 87%) of the title compound is isolated as a colorless oil.

$^1$H-NMR (CDCl$_3$): δ=0.02–0.14 (18H), 0.85 (3H), 0.88–0.97 (30H), 1.03–1.80 (9H), 1.08 (3H), 1.20 (3H), 1.60+1.68 (3H), 1.90–2.06 (3H), 2.42 (2H), 3.01 (1H), 3.68 (2H), 3.83 (1H), 4.08 (1H), 4.21 (1H), 5.18 (1H), 6.01 (1H), 7.12 (1H), 7.63 (1H), 7.72 (1H), 8.56 (1H) ppm.

Example 17u (3S,6R,7S,8S,12E/Z,15S,16Z)-6-Ethyl-3,7,15-tris-[[(1,1-dimethylethyl)dimethylsilyl]oxy]-16-fluoro-5-oxo-4,4,8,12-tetramethyl-17-(2-pyridyl)-heptadeca-12,16-dienal The solution of 400 μl of oxalyl chloride in 16 ml of anhydrous dichloromethane is cooled under an atmosphere of dry argon to −70° C., mixed with 650 μl of dimethyl sulfoxide, the solution of 1.51 g (1.81 mmol) of the compound, presented according to Example 17t, in 16 ml of anhydrous dichloromethane, and it is stirred for 0.5 hour. Then, it is mixed with 2 ml of triethylamine, allowed to react for 1 hour at −30° C. and mixed with n-hexane and saturated sodium bicarbonate solution. The organic phase is separated, the aqueous phase is extracted several more times with n-hexane, the combined organic extracts are washed with water and dried on magnesium sulfate. The residue that is obtained after filtration and removal of the solvent is purified by chromatography on fine silica gel with a gradient system that consists of n-hexane and ethyl acetate. 1.48 g (1.77 mmol, 98%) of the title compound is isolated as a pale yellow oil.

$^1$H-NMR (CDCl$_3$) of a purified sample: δ=0.02–0.13 (18H), 0.82 (3H), 0.85–0.97 (30H), 1.10–1.80 (7H), 1.10 (3H), 1.22 (3H), 1.60+1.68 (3H), 1.89–2.07 (2H), 2.32–2.48 (3H), 2.57 (1H), 3.00 (1H); 3.81 (1H), 4.21 (1H), 4.48 (1H), 5.18 (1H), 6.01 (1H), 7.12 (1H), 7.66 (1H), 7.73 (1H), 8.57 (1H), 9.78 (1H) ppm.

Example 17v (3S,6R,7-S,8S,12Z,15S,16Z)-6-Ethyl-3,7,15-tris-[[(1,1-dimethylethyl)dimethylsilyl]oxy]-16-fluoro-5-oxo-4,4,8,12-tetramethyl-17-(2-pyridyl)-heptadeca-12,16-dienoic Acid (A) and (3S,6R,7S,8S,12E,15S,16Z)-6-ethyl-3,7,15-tris-[[(1,1-dimethylethyl)dimethylsilyl]oxy]-16-fluoro-5-oxo-4,4,8,12-tetramethyl-17-(2-pyridyl)-heptadeca-12,16-dienoic Acid (B)

The solution of 1.48 g (1.77 mmol) of the compound, presented according to Example 17u, in 54 ml of tert-butanol is mixed with 50 ml of a 2 molar solution of 2-methyl-2-butene in tetrahydrofuran, cooled to 2° C., mixed with 14 ml of water, 731 mg of sodium dihydrogen phosphate, 1.24 g of sodium chloride, allowed to heat to 15° C. and stirred for 2 hours. It is poured into saturated sodium thiosulfate solution, diluted with water and extracted several times with ethyl acetate. The combined organic extracts are dried on sodium sulfate, and the residue that is obtained after filtration and removal of the solvent is purified by chromatography on fine silica gel with a gradient system that consists of n-hexane and ethyl acetate. 487 mg (573 μmol, 32%) of title compound A as well as 506 mg (595 μmol, 34%) of title compound B are isolated in each case as a colorless oil.

$^1$H-NMR (CDCl$_3$) of A: δ=0.00 (3H), 0.03–0.11 (12H), 0.13 (3H), 0.79–0.98 (33H), 1.03–1.80 (8H), 1.12 (3H), 1.20 (3H), 1.71 (3H), 1.89 (1H), 2.18 (1H), 2.30–2.48 (3H), 2.52 (1H), 3.03 (1H), 3.75 (1H), 4.22 (1H), 4.41 (1H), 5.20 (1H), 6.38 (1H), 7.20 (1H), 7.72 (1H),7.82 (1H), 8.51 (1H) ppm.

$^1$H-NMR (CDCl$_3$) of B: δ=0.00 (3H), 0.04 (3H), 0.07 (3H), 0.09 (3H), 0.11 (3H), 0.15 (3H), 0.74–0.95 (33H), 0.99–1.72 (8H), 1.10 (3H), 1.22 (3H), 1.53 (3H), 1.86 (1H), 1.98 (1H), 2.27–2.66 (4H), 3.08 (1H), 3.82 (1H), 4.16 (1H), 4.33 (1H), 5.13 (1H), 6.04 (1H), 7.18 (1H), 7.71 (1H), 7.82 (1H), 8.52 (1H) ppm.

Example 17w (3S,6R,7S,8S,12Z,15S,16Z)-6-Ethyl-3,7-bis-[[(1,1-dimethylethyl)dimethylsilyl]oxy]-16-fluoro-15-hydroxy-5-oxo-4,4,8,12-tetramethyl-17-(2-pyridyl)-heptadeca-12,16-dienoic Acid The solution of 487 mg (573 μmol) of compound A, presented according to Example 17v, in 23 ml of anhydrous tetrahydrofuran is mixed under an atmosphere that consists of dry argon with 8.55 ml of a 1 molar solution of tetrabutylammonium fluoride in tetrahydrofuran, and it is stirred for 1.5 hours at 23° C. It is mixed with saturated sodium bicarbonate solution, extracted several times with ethyl acetate, washed with saturated sodium chloride solution and dried on sodium sulfate. The residue that is obtained after filtration and removal of the solvent is further reacted without purification.

Example 17x (4S,7R,8S,9S,13Z,16S(Z)-4,8-Bis-[[dimethyl(1,1-dimethylethyl)silyl]oxy]-16-(1-fluoro-2-(2-pyridyl)ethenyl)-7-ethyl-1-oxa-5,5,9,13-tetramethyl-cyclohexadec-13-ene-2,6-dione The solution of 486 mg (max. 570 μmol) of the compound, presented according to Example 17w, in a mixture of 5 ml of anhydrous tetrahydrofuran and 50 ml of toluene is mixed under an atmosphere of dry argon with 474 µl of triethylamine, 454 µl of 2,4,6-trichlorobenzoyl chloride, and it is stirred for 20 minutes. This solution is added in drops within 4.5 hours to the solution of 727 mg of 4-dimethylaminopyridine in 215 ml of toluene, and it is stirred for another 0.5 hour at 23° C. It is concentrated by evaporation, taken up in a little dichloromethane and purified by chromatography on fine silica gel with a gradient system that consists of n-hexane and ethyl acetate. 310 mg (432 µmol, 76%) of the title compound is isolated as a colorless oil.

Example 17

(4S,7R,8S,9S,13Z,16S(Z))-4,8-Dihydroxy-16-(1-fluoro-2-(2-pyridyl)ethenyl)-7-ethyl-1-5,5,9,13-tetramethyl-cyclohexadec-13-ene-2,6-dione The solution of 308 mg (429 µmol) of the compound, presented according to Example 17x, in 27 ml of anhydrous tetrahydrofuran is mixed under an atmosphere of-dry argon in portions with a total of 4.6 ml of HF-pyridine complex, and it is stirred at 23° C. for 24 hours. It is poured into saturated sodium bicarbonate solution, extracted several times with dichloromethane, and the combined organic extracts are dried on sodium sulfate. After filtration and removal of the solvent, the residue that is obtained is purified by chromatography on fine silica gel with a mixture that consists of n-hexane and ethyl acetate. 135 mg (276 µmol, 64%) of the title compound is isolated as a colorless oil.

$^1$H-NMR (CDCl$_3$): δ=0.88 (3H), 1.03 (3H), 1.10 (3H), 1.13–1.95 (8H), 1.32 (3H), 1.71 (3H), 2.28 (1H), 2.34–2.49 (3H), 2.56 (1H), 2.80 (1H), 3.21 (1H), 3.56 (1H), 3.70 (1H), 4.22 (1H), 5.13 (1H), 5.41-(1H), 6.12 (1H), 7.16 (1H), 7.63–7.75 (2H), 8.53 (1H) ppm.

Example 18

(4S,7R,8S,9S,13E,16S(Z))-4,8-Dihydroxy-16-(1-fluoro-2-(2-pyridyl)ethenyl)-7-ethyl-1-oxa-5,5,9,13-tetramethyl-cyclohexadec-13-ene-2,6-dione Example 18a (3S,6R,7S,8S,12E,15S,16Z)-6-Ethyl-3,7-bis-[[(1,1-dimethylethyl)dimethylsilyl]oxy]-16-fluoro-15-hydroxy-5-oxo-4,4,8,12-tetramethyl-17-(2-pyridyl)-heptadeca-12,16-dienoic Acid Analogously to Example 17w, 506 mg (595 µmol) of compound B that is presented according to Example 17v is reacted, and the crude product that is obtained after working-up is further reacted.

Example 18b (4S,7R,8S,9S,13E,16S(Z))-4,8-Bis-[[dimethyl(1,1-dimethylethyl)silyl]oxy]-16-(1-fluoro-2-(2pyridyl)ethenyl)-7-ethyl-1-oxa-5,5,9,13-tetramethyl-cyclohexadec-13-ene-2,6-dione Analogously to Example 17x, 577 mg (max. 595 µmol) of the compound that is presented according to Example 18a is reacted, and after working-up and purification, 273 mg (380 µmol, 64%) of the title compound is isolated as a colorless oil.

$^1$H-NMR (CDCl$_3$): δ=0.01–0.13 (12H), 0.78–0.96 (24H), 1.09 (3H), 1.20 (3H), 1.26–1.90 (8H), 1.59 (3H), 2.16 (1H), 2.39 (1H), 2.59 (1H), 2.68 (2H), 2.91 (1H), 3.91 (1H), 4.35 (1H), 5.22 (1H), 5.45 (1H), 6.08 (1H), 7.12 (1H), 7.65 (1H), 7.71 (1H), 8.56 (1H) ppm.

Example 18

(4S,7R,8S,9S,13E,16S(Z))-4,8-Dihydroxy-16-(1-fluoro-2-(2-pyridyl)ethenyl)-7-1-oxa-5,5,9,13-tetramethyl-cyclohexadec-13-ene-2,6-dione Analogously to Example 18, 273 mg (380 µmol) of the compound that is presented according to Example 18b is reacted, and after working-up and purification, 115 mg (235 µmol, 62%) of the title compound is isolated as a colorless oil.

$^1$H-NMR (CDCl$_3$): δ=0.72 (1H), 0.84 (3H), 1.00 (6H), 1.22–2.02 (8H), 1.30 (3H), 1.60 (3H), 2.21 (1H), 2.33–2.57 (3H), 2.62 (1H), 3.40 (1H), 3.78 (1H), 4.51 (1H), 5.09 (1H), 5.22 (1H), 5.53 (1H), 6.11, (1H), 7.16 (1H), 7.70 (1H), 7.80 (1H), 8.43 (1H) ppm.

Example 19

(1SR,3S(Z),7S,10R,11S,12S,16RS)-7,11-Dihydroxy-10-ethyl-3-(1-fluoro-2-(N-oxido-2-pyridyl)ethenyl)-8,8,12,16-tetramethyl-4,17-dioxabicyclo[14.1.0]heptadecane-5,9-dione The solution of 50 mg (102 µmol) of the compound, presented according to Example 17, in 3 ml of acetonitrile is mixed at 0° C. with 958 µl of a 0.1 M aqueous solution of ethylene diamine tetraacetate, 1.45 ml of trifluoroacetone, 373 mg of sodium bicarbonate, 448 mg of oxone, and it is stirred for 1.5 hours at 23° C. It is mixed with sodium thiosulfatesolution, extracted several times with ethyl acetate, the combined organic extracts are washed with saturated sodium chloride solution and dried on sodium sulfate. 61 mg (max. 102 µmol) of the title compounds, which are further reacted without purification, is isolated.

Example 20

(1S,3S(Z),7S,10R,11S,12S,16R)-7,11-Dihydroxy-10-ethyl-3-(1-fluoro-2-(2-pyridyl)ethenyl)-8,8,12,16-tetramethyl-4,17-dioxabicyclo[14.1.10]heptadecane-5,9-dione (A) and (1R,3S(Z),7S,10R,11S,12S,16S)-7,11-dihydroxy-10-ethyl-3-(1-fluoro-2-(2-pyridyl)ethenyl)-8,8,12,16-tetramethyl-4,17-dioxabicyclo[14.1.10]heptadecane-5,9-dione (B)

The solution of 60 mg (max. 102 µmol) of the compounds, presented according to Example 19, in 12 ml of trichloromethane is mixed under an atmosphere of dry argon with a molecular sieve, 2.2 ml of isopropanol, 39 mg of tetrapropylammonium perruthenate, and it is stirred for 2 days at 60° C. It is concentrated by evaporation, and the residue is purified by chromatography on analytic thin-layer plates. A mixture of dichloromethane and isopropanol is used as a mobile solvent, and a mixture of dichloromethane and methanol is used as an eluant. 17 mg (34 µmol, 28%) of title compound A and 4.3 mg (9 µmol, 8%) of title compound B are isolated.

$^1$H-NMR (CDCl$_3$) of A: δ=0.87 (3H), 1.00 (3H), 1.04 (3H), 1.25–1.98 (9H), 1.29 (3H), 1.37 (3H), 2.10–2.21 (2H), 2.42 (1H), 2.51 (1H), 2.62 (1H), 2.89 (1H), 3.33 (1H), 3. 69 (1H), 4.21 (1H), 4.44 (1H), 5.69 (1H), 6.17 (1H), 7.18 (1H), 7.70 (2H), 8.54 (1H) ppm.

$^1$H-NMR (CDCl$_3$) of B: δ=0.83 (3H), 0.94 (3H), 1.07 (3H), 1.16–2.03 (10H), 1.30 (3H), 1.38 (3H), 2.27 (1H), 2.49–2.52 (2H), 2.90–3.04 (2H), 3.21 (1H), 3.72 (1H), 3.89 (1H), 4.32 (1 H), 5.78 (1H), 6.19 (1H), 7.18 (1H), 7.61–7.79 (2H), 8.52 (1H) ppm.

Example 21

(1SR,3S(Z),7S,10R,11S,12S,16SR)-7,11-Dihydroxy-10-ethyl-3-(1-fluoro-2-(N-oxido-2-pyridyl)ethenyl)-8,8,12,16-tetramethyl-4,17-dioxabicyclo[14.1.0]heptadecane-5,9-dione Analogously to Example 19, 112 mg (229 µmol) of the compound that is presented according to Example 18 is reacted, and after working-up, 150 mg (max. 229 µmol) of the title compounds is isolated as a colorless oil.

Example 22

(4S,7R,8S,9S,13(Z)),16S(Z)-4,8-Dihydroxy-7-ethyl-16-(1-fluoro-2-(2-methyl-4-thiazolyl)ethenyl)-1-oxa-5,5,9,13-tetramethyl-cyclohexadec-13-ene-2,6-dione Analogously to Examples 1 and 5 with use of (3S)-1,3-bis[[dimethyl(1,1-dimethyl)silyl]oxy]-4,4-dimethyl-octan-5-one as an aldol component (see Example 5n), 86 mg of the title compound is obtained as a pale yellow-colored oil.
$^1$H-NMR (CDCl$_3$): δ=0.87 (3H), 1.04 (3H), 1.15–1.75 (8H), 1.10 (3H), 1.33 (3H), 1.72 (3H), 1.86 (2H), 2.20–2.40 (2H), 2.42 (1H), 2.56 (1H), 2.73 (3H), 2.82 (1H), 3.23 (1H), 3.71 (1H), 4.18 (1H), 5.12 (1H), 5.42 (1H), 6.23 (1H), 7.38 (1H) ppm.

Example 23

(4S,7R,8S,9S,13(E),16S(Z))-4,8-Dihydroxy-7-ethyl-16-(1-fluoro-2-(2-methyl-4-thiazolyl)ethenyl)-1-oxa-5,5,9,13-tetramethyl-cyclohexadec-13-ene-2,6-dione Analogously to Examples 2 and 6 with use of (3S)-1,3-bis[[dimethyl(1,1-dimethyl)silyl]oxy]-4,4-dimethyl-octan-5-one as an aldol component (see Example 5n), 96 mg of the title compound is obtained as a pale yellow-colored oil.
$^1$H-NMR (CDCl$_3$): δ=0.85 (3H), 0.7–1.6 (7H), 1.00 (3H), 1.02 (3H), 1.31 (3H), 1.62 (3H), 1.78 (1H), 1.82–2.01 (2H), 2.20 (1H), 2.40–2.67 (3H), 2.68 (3H), 3.37 (1H), 3.73 (1H), 4.40 (1H), 4.48 (1H), 5.10 (1H), 5.53 (1H), 6.15 (1H), 7.35 (1H) ppm.

Example 24

(1R,3S(Z),7S,10R,11S,12S,16S)-7,11-Dihydroxy-10-ethyl-3-(1-fluoro-2-(2-methyl-4-thiazolyl)ethenyl)-8,8,12,16-tetramethyl-4,17-dioxabicyclo[14.1.0]heptadecane-5,9-dione (A) and (1S,3S(Z),7S,10R,11S,12S,16R)-7,11-dihydroxy-10-ethyl-3-(1-fluoro-2-(2-methyl-4-thiazolyl)ethenyl)-8,8,12,16-tetramethyl-4,17-dioxabicyclo[14.1.0]heptadecane-5,9-dione (B)

Analogously to Example 3, 8 mg of title compounds A and B at a 1:4 ratio is obtained as a pale yellow-colored oil from the title compound that is produced in Example 22.
$^1$H-NMR (characteristic signals of mixture A and B, CDCl$_3$): δ=0.86 (3H), 0.94 (3H, A), 1.00 (3H, B), 1.05 (3H), 1.26 (3H), 1.29 (3H), 1.36 (3H), 1.69 (1H, B), 1.75–1.95 (1H), 2.34 (1H, B), 2.22 (1H, A), 2.44 (1H), 2.60 (1H), 2.75 (3H), 2.86 (1H, B), 2.97 (1H, A), 3.22 (1H, A), 3.35 (1H, B), 3.70 (1H, B), 3.88 (1H, A), 4.21 (1H, B), 4.31 (1H, A), 5.68 (1H, B), 5.76 (1H, A), 6.29 (1H), 7.41 (1H) ppm.

The pure title compounds A and B are separated by HPLC on a Chiralpak AD 10 µ-column with hexane/ethanol 20–50%.

Example 25

(1R,3S(Z),7S,10R,11S,12S,16R)-7,11-Dihydroxy-10-ethyl-3-(1-fluoro-2-(2-methyl-4-thiazolyl)ethenyl)-8,8,12,16-tetramethyl-4,17-dioxabicyclo[14.1.0]heptadecane-5,9-dione (A) and (1S,3S(Z),7S,10R,11S,12S,16S)-7,11-dihydroxy-10-ethyl-3-(1-fluoro-2-(2-methyl-4-thiazolyl)ethenyl)-8,8,12,16-tetramethyl-4,17-dioxabicyclo[14.1.0]heptadecane-5,9-dione (B)

Analogously to Example 3, 4.9 mg of title compound A as a nonpolar component and 3.4 mg of title compound B as a polar component are obtained as colorless oils from the title compound that is produced in Example 23.
$^1$H-NMR (CDCl$_3$) of A, δ=0.86 (3H), 0.95 (3H), 1.0–1.7 (6H), 1.04 (3H), 1.30 (3H), 1.38 (3H), 1.76 (1H), 1.85 (2H), 1.90–2.30 (3H), 2.55 (2H), 2.70 (3H), 2.89 (1H), 3.32 (1H), 3.79 (1H), 4.13 (1H), 4.30 (1H), 5.66 (1H), 6.25 (1H), 7.39 (1H) ppm.
$^1$H-NMR (CDCl$_3$) of B, δ=0.86 (3H), 0.96 (3H), 1.10 (3H), 1.15–1.93 (7H), 1.23 (3H), 1.35 (3H), 1.95–2.38 (4H), 2.58 (2H), 2.70 (3H), 2.99 (1H), 3.10 (1H), 3.27 (1H), 3.65–3.75 (2H), 4.24 (1H), 5.62 (1H), 6.21 (1H), 7.35 (1H) ppm.

Example 26

(4S,7R,8S,9S,13(Z),16S (Z))-4,8-Dihydroxy-7-ethyl-16-(1-chloro-2-(2-methyl-4-thiazolyl)ethenyl)-1-oxa-5,5,9,13-tetramethyl-cyclohexadec-13-ene-2,6-dione The title compound is obtained analogously to Example 5 with use of (3S)-1,3-bis[[dimethyl(1,1-dimethyl)silyl]oxy]-4,4-dimethyl-octan-5-one as an aldol component (see Example 5n).

Example 27

(4S,7R,8S,9S,13(E),16S(Z))-4,8-Dihydroxy-7-ethyl-16-(1-chloro-2-(2-methyl-4-thiazolyl)ethenyl)-1-oxa-5,5,9,13-tetramethyl-cyclohexadec-13-ene-2,6-dione The title compound is obtained analogously to Example 6 with use of (3S)-1,3-bis[[dimethyl(1,1-dimethyl)silyl]oxy]-4.4-dimethyl-octan-5-one as an aldol component (see Example 5n).

Example 28

(1S,3S(Z),7S,10R,11S,12S,16SR)-7,11-Dihydroxy-10-ethyl-3-(1-chloro-2-(2-methyl-4-thiazolyl)ethenyl)-8,8,12,16-tetramethyl-4,17-dioxabicyclo[14.1.0]heptadecane-5,9-dione (A) and (1R,3S(Z),7S10R,11S,12S,16S)-7,11-dihydroxy-10-ethyl-3-(1-chloro-2-(2-methyl-4-thiazolyl)ethenyl)-8,8,12,16-tetramethyl-4,17-dioxabicyclo[14.1.0]heptadecane-5,9-dione (B)

Analogously to Example 3, the title compound is obtained from the title compound that is produced in Example 26.

Example 29

(1S,3S(Z),7S,10R,11S,12S,16S)-7,11-Dihydroxy-10-ethyl-3-(1-chloro-2-(2-methyl-4-thiazolyl)ethenyl)-8,8,12,16-tetramethyl-4,17-dioxabicyclo[14.1.0]heptadecane-5,9-dione (A) and (1R,3S(Z),7S,10R,11S,12S,16R)-7,11-dihydroxy-10-ethyl-3-(1-chloro-2-(2-methyl-4-thiazolyl)ethenyl)-8,8,12,16-tetramethyl-4,17-dioxabicyclo[14.1.0]heptadecane-5,9-dione (B)

Analogously to Example 3, the title compound is obtained from the title compound that is produced in Example 27.

Example 30

(1S,3S(Z),7S,10R,11S,12S,16S)-7,11-Dihydroxy-10-ethyl-3-(1-fluoro-2-(2-pyridyl)ethenyl)-8,8,12,16-tetramethyl-4,17-dioxabicyclo[14.1.0]heptadecane-5,9-dione (A) and (1R,3S(Z),7S,10R,11S,12S,16R)-7,11-dihydroxy-10-ethyl-3-(1-fluoro-2-(2-pyridyl)ethenyl)-8,8,12,16-tetramethyl-4,17-dioxabicyclo[14.1.0]heptadecane-5,9-dione (B)

Analogously to Example 20, 150 mg (max. 229 μmol) of the compounds that are presented according to Example 21 is reacted, and after working-up and purification, 19 mg (38 μmol, 16%) of title compound A as well as 35 mg (69 μmol, 30%) of title compound B are isolated in each case as colorless oils.

$^1$H-NMR (CDCl$_3$) of A: δ=0.83 (3H), 0.93 (3H), 1.08 (3H), 1.18–1.97 (9H), 1.21 (3H), 1.36 (3H), 2.09 (1H), 2.31 (1H), 2.59 (2H), 2.99 (1H), 3.30 (1H), 3.44 (1H), 3.70 (1H), 4.33 (1H), 4.40 (1H), 5.67 (1H), 6.19 (1H), 7.18 (1H), 7.70 (2H), 8.51 (1H) ppm.

$^1$H-NMR (CDCl$_3$) of B: δ=0.85 (3H), 0.94 (3H), 1.00–1.97 (9H), 1.02 (3H), 1.29 (3H), 1.38 (3H), 2.06 (1H), 2.28 (1H), 2.54 (2H), 2.90 (1H), 3.35 (1H), 3.61 (1H), 3.79 (1H), 4.39 (2H), 5.67 (1H), 6.22 (1H), 7.18 (1H), 7.69 (1H), 7.78 (1H), 8.51 (1H) ppm.

Example 31

(4S,7R,8S,9S,13Z,16S(Z))-4,8-Dihydroxy-16-(1-chloro-2-(2-pyridyl)ethenyl)-7ethyl-1-oxa-5,5,9,13tetramethyl-cyclohexadec-13-ene-2,6-dione

Example 31a 3-(2-Pyridyl)-2-propin-1-ol

The mixture that consists of 16.6 ml (173 mmol) of 2-bromopyridine, 21.6 ml of propargyl alcohol, 2.5 g of palladium-bis-triphenylphosphine-dichloride and 173 mg of copper(I) iodide is mixed with 510 ml of diethylamine and heated for 1.5 hours to 80° C. After filtration and removal of the solvent, the residue is purified by chromatography on fine silica gel with a gradient system that consists of n-hexane and ethyl acetate. 17.8 g (134 mmol, 77%) of the title compound is isolated as a colorless oil.

$^1$H-NMR (CDCl$_3$): δ=3.70 (1H).4.54 (2H), 7.24 (1H), 7.42 (1H), 7.67 (1H), 8.53 (1H) ppm.

Example 31b (2Z)-3-(2-Pyridyl)-2-chloro-2-propen-1-ol 12.3 g (92.6 mmol) of the compound that is presented according to Example 31a is mixed with 238 ml of concentrated solution and heated for 2.5 hours to 80° C. After cooling, it is carefully poured into saturated potassium carbonate solution, extracted several times with dichloromethane, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 14.8 g (87.3 mmol, 94%) of the title compound is isolated as a crystalline solid.

$^1$H-NMR (CDCl$_3$): δ=4.36 (2H), 5.47 (1H), 7.18 (1H), 7.21 (1H), 7.72 (1H), 7.99 (1H), 8.56 (1H) ppm.

Example 31c (2Z)-3-(2-Pyridyl)-2-chloro-2-propenal

Analogously to Example 17e, 14.8 g (87.5 mmol) of the compound that is presented according to Example 31b is reacted, and after working-up, 14.6 g (87.1 mmol, 99%) of the title compound is isolated as a pale yellow oil.

$^1$H-NMR (CDCl$_3$): δ=7.36 (1H), 7.74 (1H), 7.83 (1H), 8.34 (1H), 8.77 (1H), 9.57 (1H) ppm.

Example 31d (3S,4Z)-5-(2-Pyridyl)-1-[(4S,5R)-4-methyl-5-phenyl-1,3-oxazolidin-2-on-3-yl]-3-hydroxy-4-chloro-4-penten-1-one (A) and (3R,4Z)-5-(2-pyridyl)-1-[(4S,5R)-4-methyl-5-phenyl-1,3-oxazolidin-2-on-3-yl]-3-hydroxy-4-chloro-4-penten-1-one (B)

Analogously to Example 17f, 14.6 g (87.1 mmol) of the compound that is presented according to Example 31c is reacted, and after working-up and separation, 12.3 g (31.8 mmol, 37%) of crystalline title compound A as well as 9.6 g (24.8 mmol, 28%) of title compound B are isolated as colorless oils.

$^1$H-NMR (CDCl$_3$) of A: δ=0.94 (3H), 3.42 (1H), 3.58 (1H), 4.50 (1H), 4.81 (1H), 4.91 (1H), 5.70 (1H), 7.14–7.48 (7H), 7.72 (1H), 7.96 (1H), 8.62 (1H) ppm.

$^1$-NMR (CDCl$_3$) of B: δ=0.96 (3H), 3.50 (2H), 4.82 (1H), 4.96 (1H), 5.72 (1H), 7.13–7.50 (7H), 7.73 (1H), 7.97 (1H), 8.65 (1H) ppm.

Example 31e (4Z)-5-(2-Pyridyl)-1-[(4S,5R)-4-methyl-5-phenyl-1,3-oxazolidin-2-on-3-yl]-4chloro-4-pentene-1,3-dione Analogously to Example 17g, 11.3 g (29.2 mmol) of compound B that is presented according to Example 31d is reacted, and after working-up, 9.8 g (25.5 mmol, 87%) of the title compound is isolated as a crystalline solid.

$^1$H-NMR (CDCl$_3$) as a ketone/enol mixture: δ=0.99 (3H), 4.49 (0.6H), 4.60 (0.6H), 4.87 (1H), 5.71+5.76 (1H), 7.21–7.52 (6.4H), 7.79 (1H), 7.92 (1H), 8.10+8.20 (1H), 8.72 (1H), 13.66 (0.4H) ppm.

Example 31f (3S,4Z)-5-(2-Pyridyl)-1-[(4S,5R)-4-methyl-5-phenyl-1,3-oxazolidin-2-on-3-yl]-3-[[dimethyl(1,1-dimethylethyl)dilyl]oxy]-4-chloro-4-penten-1-one Analogously to Example 17i, 12.3 g (31.7 mmol) of compound A that is presented according to Example 31d and/or Example 31f is reacted, and after working-up and purification, 12.2 g (24.3 mmol, 77%) of the title compound is isolated as a colorless oil.

$^1$H-NMR (CDCl$_3$): δ=0.13 (6H), 0.90 (12H), 3.30 (1H), 3.59 (1H), 4.78 (1H), 5.01 (1H), 5.66 (1H), 7.02 (1H), 7.19 (1H), 7.23–7.48 (5H), 7.71 (1H), 7.97 (1H), 8.62 (1H) ppm.

Example 31g (3S,4Z)-5-(2-Pyridyl)-3-[[dimethyl(1,1-dimethylethyl)silyl]oxy]-4-chloro-4-pentenoic Acid Ethyl Ester Analogously to Example 17j, 12.1 g (24.1 mmol) of the compound that is presented according to Example 31f is reacted, and after working-up and purification, 8.3 g (22.4 mmol, 93%) of the title compound is isolated as a colorless oil.

$^1$H-NMR (CDCl$_3$): δ=0.11 (6H), 0.90 (9H), 1.26 (3H), 2.75 (2H), 4.14 (2H), 4.83 (1H), 7.00 (1H), 7.18 (1H), 7.69 (1H), 7.91 (1H), 8.61 (1H) ppm.

Example 31h (3S,4Z)-5-(2-Pyridyl)-3-[[dimethyl(1,1-dimethylethyl) silyl]oxy]-4-chloro-4-penten-1-ol Analogously to Example 17k, 8.1 g (21.9 mmol) of the compound that is presented according to Example 31g is reacted, and after working-up and purification, 6.3 g (19.2 mmol, 88%) of the title compound is isolated as a colorless oil.

$^1$H-NMR (CDCl$_3$): δ=0.13 (3H), 0.18 (3H), 0.96 (9H), 1.98–2.10 (3H), 3.70–3.91 (2H), 4.60 (1H), 7.00 (1H), 7.19 (1H), 7.70 (1H), 7.93 (1H), 8.62 (1H) ppm.

Example 31i (3S4Z)-5-(2-Pyridyl)-3-[[dimethyl(1,1-dimethylethyl)silyl]oxy]-1-iodo-4-chloro-4-pentene Analogously to Example 17l, 6.3 g (19.2 mmol) of the compound that is presented according to Example 31h is reacted, and after working-up and purification, 7.8 g (17.8 mmol, 93%) of the title compound is isolated as a colorless oil.

$^1$H-NMR (CDCl$_3$): δ=0.12 (3H), 0.19 (3H), 0.93 (9H), 2.25 (2H), 3.24 (2H), 4.48 (1H), 7.00 (1H), 7.20 (1H), 7.71 (1H), 7.97 (1H), 8.63 (1H) ppm.

Example 31k (3S,4Z)-5-(2-Pyridyl)-3-[[dimethyl(1,1-dimethylethyl) silyl]oxy]-4-chloro-4-penten-1-triphenylphosphonium Iodide Analogously to Example 17m, 7.8 g (17.8 mmol) of the compound that is presented according to Example 31i is reacted, and after working-up and purification, 11.4 g (16.3 mmol, 91%) of the title compound is isolated as a crystalline solid.

$^1$H-NMR (CDCl$_3$): δ=0.15 (3H), 0.21 (3H), 0.90 (9H), 1.96–2.20 (2H), 3.52–3.91 (2H), 5.02 (1H), 7.18 (1H), 7.25 (1H), 7.63–7.88 (17H), 8.61 (1H) ppm.

Example 31l (2S,6E/Z,9S,10Z)-9-[[Dimethyl(1,1-dimethylethyl) silyl]oxy]-10-chloro-11-(2-pyridyl)-1-(tetrahydropyran-2-yloxy)-2,6-dimethyl-undeca-6,10-diene Analogously to Example 17n, 3.00 g of the compound, presented according to Example 31k, is reacted with 653 mg (2.86 mmol) of (2S)-2-methyl-6-oxo-heptane-1-(tetrahydropyran-2-yloxy), which was produced analogously to the process described in DE 197 51 200.3 or WO 99/07692, and after working-up and purification, in addition to starting material, 202 mg (0.39 mmol, 14%) of the title compound is isolated as a colorless oil.

$^1$H-NMR (CDCl$_3$): δ=0.08 (6H), 0.80–0.96 (12H), 1.08 (1H), 1.22–2.05 (12H), 1.61+1.67 (3H), 2.31–2.55 (2H), 3.03–3.25 (1H), 3.40–3.62 (2H), 3.84 (1H), 4.28 (1H), 4.53 (1H), 5.15 (1H), 6.91 (1H), 7.16 (1H), 7.68 (1H), 7.95 (1H), 8.60 (1H) ppm.

Example 31m (2S,6E/Z,9S,10Z)-9-[[Dimethyl(1,1-dimethylethyl) silyl]oxy]-10-chloro-11-(2-pyridyl)-1-hydroxy-2,6-dimethyl-undeca-6,10-diene Analogously to Example 17o, 472 mg (904 μmol) of the compound that is presented according to Example 31l is reacted, and after working-up and purification, 278 mg (635 μmol, 70%) of the title compound is isolated as a colorless oil.

$^1$H-NMR (CDCl$_3$): δ=0.09 (6H), 0.82–0.97 (12H), 0.98–2.12 (8H), 1.60+1.68 (3H), 2.32–2.58 (2H), 3.63–3.54 (2H), 4.30 (1H), 5.11+5.19 (1H), 6.89+6.92 (1H), 7.19 (1H), 7.70 (1H), 7.98+8.04 (1H), 8.59 (1H) ppm.

Example 31n (2S,6E/Z,9S,10Z)-9-[[Dimethyl(1,1-dimethylethyl) silyl]oxy]-10-chloro-11-(2-pyridyl)-2,6-dimethyl-undeca-6,10-dienal Analogously to Example 17p, 278 mg (635 μmol) of the compound that is presented according to Example 31m is reacted, and after working-up, 273 mg (626 μmol, 99%) of the title compound is isolated as a pale yellow oil.

Example 31o (4S(4R,5S,6S,10E/Z,13S,14Z))-4-(13-[[(1,1-Dimethylethyl)dimethylsilyl]oxy]-4-ethyl-14-chloro-15-(2-pyridyl)-3-oxo-5-hydroxy-2,6,10-trimethyl-pentadeca-10,14-dien-2-yl)-2,2-dimethyl-[1.3] dioxane (A) and (4S(4S,5R,6S,10E/Z,13S,14Z))-4-(13-[[(1,1-dimethylethyl)-dimethylsilyl]oxy]-4-ethyl-14-chloro-15-(2-pyridyl)-3-oxo-5-hydroxy-2,6, 10-trimethyl-pentadeca-10,14-dien-2-yl)-2,2-dimethyl-[1.3]dioxane (B)

Analogously to Example 17q, 273 mg (626 μmol) of the compound, presented according to Example 31n, is reacted with (4S)-4-(2-methyl-3-oxo-hex-2-yl)-2,2-dimethyl-[1,3]dioxane, which was produced according to the process that is described in DE 19751200.3 or WO 99/07692, and after working-up and purification, 275 mg (414 μmol, 66%) of title compound A, and after purification, 58 mg (87 μmol, 14%) of title compound B are isolated in each case as colorless oils.

$^1$H-NMR (CDCl$_3$) of A: δ=0.07 (6H), 0.82 (6H), 0.91 (9H), 0.99 (3H), 1.08 (1H), 1.17–2.08 (9H), 1.23-(3H), 1.31 (3H), 1.39 (3H), 1.60+1.68 (3H), 2.31–2.56 (2H), 2.89 (1H), 3.19 (1H), 3.43 (1H), 3.88 (1H), 3.98 (1H), 4.18 (1H), 4.29 (1H), 5.16 (1H), 6.91 (1H), 7.18 (1H), 7.69 (1H), 7.97 (1H), 8.60 (1H) ppm.

Example 31p (3S,6R,7S,8S,12E/Z,15S,16Z)-15-[[(1,1-Dimethylethyl)dimethylsilyl]oxy]-6-ethyl-16-chloro-1,3,7-trihydroxy-4,4,8,12-tetramethyl-17-(2-pyridyl)-heptadeca-12,16-dien-5-one Analogously to Example 17r, 275 mg (414 mmol) of compound A that is presented according to Example 31o is reacted, and after working-up and purification, 234 mg (375 μmol, 91%) of the title compound is isolated as a colorless oil.

$^1$H-NMR (CDCl$_3$): δ=0.03–0.12 (6H), 0.78–0.95 (15H), 0.98–2.18 (10H), 1.09 (3H), 1.26 (3H), 1.60+1.68 (3H), 2.32–2.58 (2H), 2.72–2.98 (2H), 3.19 (1H), 3.41 (1H), 3.71–4.00 (3H), 4.12 (1H), 4.28 (1H), 5.11+5.21 (1H), 6.82+6.83 (1H), 7.20 (1H), 7.71 (1H), 8.03 (1H), 8.63 (1H) ppm.

Example 31q (3S,6R,7S,8S,12E/Z,15S,16Z)-6-Ethyl-1,3,7,15-tetrakis-[[(1,1-dimethylethyl)dimethylsilyl]oxy]-16-chloro-4,4,8,12-tetramethyl-17-(2-pyridyl)-heptadeca-12,16-dien-5-one Analogously to Example 17s, 234 mg (375 μmol) of the compound that is presented according to Example 31p is reacted, and after working-up and purification, 325 mg (336 µmol, 90%) of the title compound is isolated as a colorless oil.

$^1$H-NMR (CDCl$_3$): δ=−0.04–0.10 (24H), 0.76–1.78 (51H), 1.01 (3H), 1.23 (3H), 1.59+1.63 (3H), 1.89–2.03 (2H), 2.29–2.54 (2H), 3.00 (1H), 3.50–3.71 (2H), 3.80 (1H), 3. (1H), 4.26 (1H), 5.13 (1H), 6.91 (1H), 7.15 (1H), 7.68 (1H), 7.94 (1H), 8.60 (1H) ppm.

Example 31r (3S,6R,7S,8S,12E/Z,15S,16Z)-6-Ethyl-3,7,15-tris-[[(1,1-dimethylethyl)dimethylsilyl]oxy]-1-hydroxy-16-chloro-4,8,12-tetramethyl-17-(2-pyridyl)-heptadeca-12,16-dien-5-one Analogously to Example 17t, 325 mg (336 µmol) of the compound that is presented according to Example 31q is reacted, and after working-up and purification, 264 mg (310 µmol, 92%) of the title compound is isolated as a colorless oil.

$^1$H-NMR (CDCl$_3$): δ=0.01–0.12 (18H), 0.79–0.97 (33H), 1.01–2.08 (12H), 1.08 (3H), 1.19 (3H), 1.60+1.68 (3H), 2.31–2.56 (2H), 3.01 (1H), 3.68 (2H), 3.84 (1H), 4.08 (1H), 4.29 (1H), 5.18 (1H), 6.93 (1H), 7.19 (1H), 7.69 (1H), 7.97 (1H), 8.61 (1H) ppm.

Example 31s (3S,6R,7S,8S,12E/Z,15S,16Z)-6-Ethyl-3,7,15-tris-[[(1,1-dimethylethyl)dimethylsilyl]oxy]-16-chloro-5-4,4,8,12-tetramethyl-17-(2-pyridyl)-heptadeca-12,16-dienal Analogously to Example 17u, 264 mg (310 µmol) of the compound that is presented according to Example 31r is reacted, and after working-up, 238 mg (280 µmol, 90%) of the title compound is isolated as a pale yellow oil, which is further reacted without purification.

Example 31t (3S,6R,7S,8S,12Z,15S,16Z)-6-Ethyl-3,7,15-tris-[[(1,1-dimethylethyl)dimethylsilyl]oxy]-16-chloro-5-oxo-4,4,8,12-tetramethyl-17-(2-pyridyl)-heptadeca-12,16-dienoic Acid (A) and (3S,6R,7S,8S,12E,15S,16Z)-6-ethyl-3,7,15-tris-[[(1,1-dimethylethyl)dimethylsilyl]oxy]-16-chloro-5-oxo-4,4,8,12-tetramethyl-17-(2-pyridyl)-heptadeca-12,16-dienoic Acid (B)

Analogously to Example 17v, 238 mg (280 µmol) of the compound that is presented according to Example 31s is reacted, and after working-up and purification, 111 mg (128 µmol, 46%) of title compound A as well as 102 mg (118 µmol, 42%) of title compound B are isolated in each case as colorless oils.

$^1$H-NMR (CDCl$_3$) of A: δ=−0.01–0.15 (18H), 0.79–0.97 (33H), 1.02–2.43 (13H), 1.12 (3H), 1.21 (3H), 1.71 (3H), 2.56 (1H), 3.01 (1H), 3.77 (1H), 4.31 (1H), 4.39 (1H), 5.19 (1H), 7.16 (1H), 7.24 (1H), 7.76 (1H), 8.09 (1H), 8.59 (1H) ppm.

$^1$H-NMR (CDCl$_3$) of B: δ=0.00–0.19 (18H), 0.78–0.97 (33H), 1.00–1.73 (8H), 1.11 (3H), 1.21 (3H), 1.58 (3H), 1.87 (1H), 2.00 (1H), 2.29–2.43 (2H), 2.53 (1H), 2.63 (1H), 3.09 (1H), 3.87 (1H), 4.32 (2H), 5.13 (1H), 6.93 (1H), 7.26 (1H), 7.78 (1H), 8.12 (1H), 8.61 (1H) ppm.

Example 31u (3S,6R,7S,8S,12Z,15S,16Z)-6-Ethyl-3,7-bis-[[(1,1-dimethylethyl)dimethylsilyl]oxy]-16-chloro-15-hydroxy-5-oxo-4,4,8,12-tetramethyl-17-(2-pyridyl)-heptadeca-12,16-dienoic Acid Analogously to Example 17w, 111 mg (128 µmol) of compound A that is presented according to Example 31t is reacted, and after working-up, 105 mg (max. 128 µmol) of the title compound is isolated as a crude product, which is further reacted without purification.

Example 31v (4S,7R,8S,9S,13Z,16S(Z))-4,8-Bis-[[dimethyl(1,1-dimethylethyl)silyl]oxy]-16-(1-chloro-2-(2-pyridyl)ethenyl)-7-ethyl-1-oxa-5,5,9,13-tetramethyl-cyclohexadec-13-ene-2,6-dione Analogously to Example 17x, 105 mg (max. 128 µmol) of the compound that is presented according to Example 31u is reacted, and after working-up and purification, 61 mg (83 µmol, 65%) of the title compound is isolated as a colorless oil.

$^1$H-NMR (CDCl$_3$): δ=−0.11 (3H), 0.08 (3H), 0.11 (6H), 0.69–1.98 (19H), 0.73 (3H), 0.84 (9H), 0.94 (3H) 1.22 (3H), 1.68 (3H), 2.29 (1H), 2.45 (1H), 2.65 (1H), 2.84 (1H), 3.02 (1H), 3.99 (2H), 5.14 (2H), 6.98 (1H), 7.19 (1H), 7.69 (1H), 7.98 (1H), 8.61 (1H) ppm.

Example 31

(4S,7R,8S,9S,13Z,16S(Z))-4,8-Dihydroxy-16-(1-chloro-2-(2-pyridyl)ethenyl)-7-ethyl-1-oxa-5,5,9,13-tetramethyl-cyclohexadec-13-ene-2,6-dione Analogously to Example 17, 61 mg (83 µmol) of the compound that is presented according to Example 31v is reacted, and after working-up and purification, 24 mg (47 µmol, 57%) of the title compound is isolated as a colorless oil.

$^1$H-NMR (CDCl$_3$): δ=0.88 (3H), 1.03 (3H), 1.09 (3H), 1.20–1.92 (7H), 1.36 (3H), 1.86 (3H), 2.24–2.62 (5H), 2.82 (1H), 3.22 (1H), 3.49 (1H), 3.70 (1H), 4.06 (1H), 4.32 (1H), 5.12 (1H), 5.41 (1H), 7.00 (1H), 7.22 (1H), 7.72 (1H), 7.91 (1H), 8.57 (1H) ppm.

Example 32

(4S,7R,8S,9S,13E,16S(Z))-4,8-Dihydroxy-16-(1-chloro-2-(2-pyridyl)ethenyl)-7-ethyl-1-oxa-5,5,9,13-tetramethyl-cyclohexadec-13-ene-2,6-dione

Example 32a (3S,6R,7S,8S,12E,15S,16Z)-6-Ethyl-3,7-bis-[[(1,1-dimethylethyl)dimethylsilyl]oxy]-16-chloro-15-hydroxy-5-oxo-4,4,8,12-tetramethyl-17-(2-pyridyl)-heptadeca-12,16-dienoic Acid Analogously to Example 17w, 102 mg (118 µmol) of compound B that is presented according to Example 31t is reacted, and after working-up, 92 mg (max. 118 µmol) of the title compound is isolated as a crude product, which is further reacted without purification.

Example 32b (4S,7R,8S,9S,13E,16S(Z))-4,8-Bis-[[dimethyl(1,1-dimethylethyl)silyl]oxy]-16-(1-chloro-2-(2-pyridyl)ethenyl)-7-ethyl-1-oxa-5,5,9,13-tetramethyl-cyclohexadec-13-ene-2,6-dione Analogously to Example 17x, 92 mg (max. 118 µmol) of the compound that is presented according to Example 32a is reacted, and after working-up and purification, 62 mg (84 µmol, 72%) of the title compound is isolated as a colorless oil.

1H-NMR (CDCl3): δ=0.04–0.19 (12H), 0.78–2.00 (14H), 0.58 (9H), 0.90 (9H), 1.11 (3H), 1.22 (3H), 1.62 (3H), 2.16 (1H), 2.41 (1H), 2.52–2.81 (3H), 2.91 (1H), 3.91 (1H), 4.36 (1H), 5.23 (1H), 5.47 (1H), 6.98 (1H), 7.18 (1H), 7.69 (1H), 7.89 (1H), 8.61 (1H) ppm.

Example 32

(4S,7R,8S,9S,13E,16S(Z))-4,8-Dihydroxy-16-(1-chloro-2-(2-pyridyl)ethenyl)-7-ethyl-1-oxa-5,5,9,13tetramethyl-cyclohexadec-13-ene-2,6-dione Analogously to Example 17, 62 mg (84 μmol) of the compound that is presented according to Example 32b is reacted, and after working-up and purification, 17 mg (34 μmol, 40%) of the title compound is isolated as a colorless oil.

1H-NMR (CDCl3): δ=0.76 (1H), 0.83 (3H), 0.99 (3H), 1.02 (6H), 1.28 (3H), 1.37–2.00 (8H), 1.61 (3H), 2.21 (1H), 2.42 (1H), 2.51 (1H), 2.61 (2H), 3.40 (1H), 3.76 (1H), 4.55 (1H), 5.04 (1H), 5.10 (1H), 5.51 (1H), 6.96 (1H), 7.21 (1H), 7.73 (1H), 8.17 (1H), 8.49 (1H) ppm.

Example 33

(1RS,3S(Z),7S,10R,11S,12S,16RS)-7,11-Dihydroxy-10-ethyl-3-(1-fluoro-2-(2-pyridyl)ethenyl)8,8,12,16-tetramethyl-4,17-dioxabicyclo[14.1.0]heptadecane-5,9-dione Analogously to Example 19, 17 mg (34 μmol) of the compound that is presented according to Example 32 is reacted, and after working-up, 23 mg (max. 34 μmol) of the title compounds is isolated as a colorless oil.

Example 34

(1S,3S(Z),7S,10R,11S,12S,16S)-7,11-Dihydroxy-10-ethyl-3-(1-fluoro-2-(2-pyridyl)ethenyl)8,8,12,16-tetramethyl-4,17-dioxabicyclo[14.1.0]heptadecane-5,9-dione (A) and (1R,3S(Z),7S,10R,11S,12S,16R)-7,11-dihydroxy-10-ethyl-3-(1-fluoro-2-(2-pyridyl)ethenyl)8,8,12,16-tetramethyl-4,17-dioxabicyclo[14.1.0]heptadecane-5,9-dione (B)

Analogously to Example 17, 23 mg (max. 34 μmol) of the compounds that are presented according to Example 32 is reacted, and after working-up and purification, 3.6 mg (6.9 μmol, 20.3%) of title compound A as well at 4.9 mg (9.4 μmol, 27.7%) of title compound B are isolated in each case as colorless oils.

1H-NMR (CDCl3) of A: δ=0.85 (3H), 0.95 (3H), 1.08 (3H) 1.24 (3H), 1.37 (3H), 1.72–1.95 (3H), 2.24 (2H), 2.50–2.64 (2H), 2.98 (1H), 3.23 (1H), 3.30 (1H), 3.69 (1H), 4.07 (1H), 4.34 (1H) 5.64 (1H), 7.07 (1H), 7.23 (1H), 7.73 (1H), 7.97 (1H), 8.58 (1H) ppm.

1H-NMR (CDCl3) of B: δ=0.87 (3H), 0.97 (3H), 1.04 (3H) 1.29 (3H), 1.37 (3H), 1.75–2.09 (6H), 2.40 (1H), 2.54 (2H), 2.87 (1H), 3.38 (1H), 3.80 (1H), 4.20 (1H), 4.47 (1H), 5.61 (1H), 7.11 (1H), 7.23 (1H), 7.76 (1H), 8.10 (1H), 8.57 (1H) ppm.

What is claimed is:

1. Epothilone derivatives of general formula I,

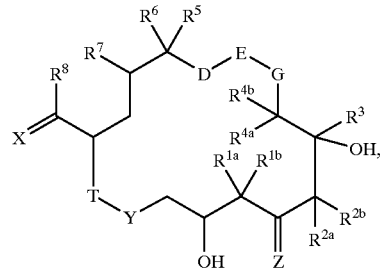

in which
$R^{1a}$, $R^{1b}$ are the same or different and mean hydrogen, $C_1$–$C_{10}$ alkyl, aryl, $C_7$–$C_{20}$ aralkyl, or together a —$(CH_2)_n$— group with m=2, 3, 4 or 5,
$R^{2a}$, $R^{2b}$ are the same or different and mean hydrogen, $C_1$–$C_{10}$ alkyl, aryl, $C_7$–$C_{20}$ aralkyl or together a —$(CH_2)_n$— group with n=2, 3, 4 or 5,
$R^3$ means hydrogen, $C_1$–$C_{10}$ alkyl, aryl, $C_7$–$C_{20}$ aralkyl,
G means an oxygen atom or a group —$CH_2$,
$R^{4a}$, $R^{4b}$ are the same or different and mean hydrogen, $C_1$–$C_{10}$ alkyl, aryl, $C_7$–$C_{20}$ aralkyl or together a —$(CH_2)_p$— group with p=2, 3, 4 or 5,
D—E means a group

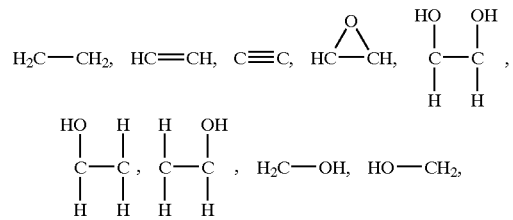

$R^5$ means hydrogen, $C_1$–$C_{10}$ alkyl, aryl, $C_7$–$C_{20}$ aralkyl, $CO_2H$, $CO_2$-alkyl, $CH_2OH$, $CH_2O$-alkyl, $CH_2O$-acyl, CN, $CH_2NH_2$, $CH_2N$ (alkyl, acyl)$_{1,2}$, $CH_2Hal$
$R^6$, $R^7$ each mean a hydrogen atom, together an additional bond or an oxygen atom,
$R^8$ means a halogen atom, or a cyano group,
X means an oxygen atom, two alkoxy groups $OR^{23}$, a $C_2$–$C_{10}$ alkylene-α,ω-dioxy group, which can be straight-chain or branched, H/$OR^9$ or a grouping $CR^{10}R^{11}$,
whereby
$R^{23}$ stands for a $C_1$–$C_{20}$ alkyl radical,
$R^9$ stands for hydrogen or a protective group PG$^x$,
$R^{10}$, $R^{11}$ are the same or different and stand for hydrogen, a $C_1$–$C_{20}$ alkyl, aryl, $C_7$–$C_{20}$ aralkyl radical or $R^{10}$ and $R^{11}$ together with the methylene carbon atom together stand for a 5- to 7-membered carbocyclic ring,
T—Y means a group $NR^{24}$—C(=O), or $NR^{24}$—$SO_2$,
$R^{24}$ means hydrogen, $C_1$–$C_{10}$ alkyl,
Z means an oxygen atom or H/$OR^{12}$,
whereby
$R^{12}$ is hydrogen or a protective group PG$^z$.

2. Compounds according to claim 1, in which $R^8$ is a fluorine atom.

3. Compounds according to claim 1, in which $R^8$ is a chlorine atom.

4. Compounds according to claim 1, in which $R^{2a}$ means a methyl, ethyl or propyl group.

5. Compounds according to claim 2, in which $R^{2a}$ means a methyl, ethyl or propyl group.

6. Compounds according to claim 3, in which $R^{2a}$ means a methyl, ethyl or propyl group.

7. Compounds according to claim 1, in which $R^{1a}$ and $R^{1b}$ together mean a trimethylene group.

8. Compounds according to claim 2, in which $R^{1a}$ and $R^{1b}$ together mean a trimethylene group.

9. Compounds according to claim 3, in which $R^{1a}$ and $R^{1b}$ together mean a trimethylene group.

10. Compounds according to claim 1, in which $R^{1a}$ and $R^{1b}$ each mean a methyl group.

11. Compounds according to claim 2, in which $R^{1a}$ and $R^{1b}$ each mean a methyl group.

12. Compounds according to claim 3, in which $R^{1a}$ and $R^{1b}$ each mean a methyl group.

13. Compounds according to claim 1, in which $R^{10}/R^{11}$ stand for a 2-pyridyl radical/hydrogen.

14. Compounds according to claim 2, in which $R^{10}/R^{11}$ stand for a 2-pyridyl radical/hydrogen.

15. Compounds according to claim 3, in which $R^{10}/R^{11}$ stand for a 2-pyridyl radical/hydrogen.

16. Compounds according to claim 1, in which $R^{10}/R^{11}$ stand for a 2-methyl-4-thiazolyl radical/hydrogen.

17. Compounds according to claim 2, in which $R^{10}/R^{11}$ stand for a 2-methyl-4-thiazolyl radical/hydrogen.

18. Compounds according to claim 3, in which $R^{10}/R^{11}$ stand for a 2-methyl-4-thiazolyl radical/hydrogen.

19. Compounds according to claim 1, in which $R^{10}/R^{11}$ stand for a 2-hydroxymethyl-4-thiazolyl radical/hydrogen or a 2-methyl-4-oxazolyl radical/hydrogen or a 2-hydroxymethyl-4-oxazolyl radical/hydrogen.

20. Compounds according to claim 2, in which $R^{10}/R^{11}$ stand for a 2-hydroxymethyl-4-thiazolyl radical/hydrogen or a 2-methyl-4-oxazolyl radical/hydrogen or a 2-hydroxymethyl-4-oxazolyl, radical/hydrogen.

21. Compounds according to claim 3, in which $R^{10}/R^{11}$ stand for a 2-hydroxymethyl-4-thiazolyl radical/hydrogen or a 2-methyl-4-oxazolyl radical/hydrogen or a 2-hydroxymethyl-4-oxazolyl radical/hydrogen.

22. Compounds according to claim 1, in which T—Y is a group $NR^{24}$—C(=O) with $R^{24}$ in the already indicated meaning.

23. Compounds according to claim 2, in which T—Y is a group $NR^{24}$—C(=O) with $R^{24}$ in the already indicated meaning.

24. Compounds according to claim 3, in which T—Y is a group $NR^{24}$—C(=O) with $R^{24}$ in the already indicated meaning.

25. Compounds according to claim 1, in which G is a methylene group.

26. Compounds according to claim 2, in which G is a methylene group.

27. Compounds according to claim 3, in which G is a methylene group.

28. Compounds according to claim 1, in which Z is an oxygen atom.

29. Compounds according to claim 2, in which Z is an oxygen atom.

30. Compounds according to claim 3, in which Z is an oxygen atom.

31. Compounds according to claim 1, in which —D—E stands for an ethylene group.

32. Compounds according to claim 2, in which —D—E stands for an ethylene group.

33. Compounds according to claim 3, in which —D—E stands for an ethylene group.

34. Compounds according to claim 1, in which $R^3$ stands for a hydrogen atom.

35. Compound according to claim 2, in which $R^3$ stands for a hydrogen atom.

36. Compounds according to claim 3, in which $R^3$ stands for a hydrogen atom.

37. Compounds according to claim 1, in which $R^{4a}/R^{4b}$ stand for $H/CH_3$.

38. Compounds according to claim 2, in which $R^{4a}/R^{4b}$ stand for $H/CH_3$.

39. Compounds according to claim 3, in which $R^{4a}/R^{4b}$ stand for $H/CH^3$.

40. Compounds according to claim 2, in which $R^{2a}/R^{2b}$ stand for methyl or ethyl/hydrogen.

41. Compounds according to claim 3, in which $R^{2a}/R^{2b}$ stand for methyl or ethyl/hydrogen.

42. Compounds according to claim 8, in which $R^{2a}/R^{2b}$ stand for methyl or ethyl/hydrogen.

43. Compounds according to claim 9, in which $R^{2a}/R^{2b}$ stand for methyl or ethyl/hydrogen.

44. Compounds according to claim 8, in which $R^{10}/R^{11}$ stand for a 2-pyridyl radical/hydrogen or a 2-methyl-4-thiazolyl radical/hydrogen or a 2-hydroxymethyl-4-thiazolyl radical/hydrogen or a 2-methyl-4-oxazolyl radical/hydrogen or a 2-hydroxymethyl-4-oxazolyl radical/hydrogen.

45. Compounds according to claim 9, in which $R^{10}/R^{11}$ stand for a 2-pyridyl radical/hydrogen or a 2-methyl-4-thiazolyl radical/hydrogen or a 2-hydroxymethyl-4-thiazolyl radical/hydrogen or a 2-methyl-4-oxazolyl radical/hydrogen or a 2-hydroxymethyl-4-oxazolyl radical/hydrogen.

46. Compounds according to claim 11, in which $R^{10}/R^{11}$ stand for a 2-pyridyl radical/hydrogen or a 2-methyl-4-thiazolyl radical/hydrogen or a 2-hydroxymethyl-4-thiazolyl radical/hydrogen or a 2-methyl-4-oxazolyl radical/hydrogen or a 2-hydroxymethyl-4-oxazolyl radical/hydrogen.

47. Compounds according to claim 12, in which $R^{10}/R^{11}$ stand for a 2-pyridyl radical/hydrogen or a 2-methyl-4-thiazolyl radical/hydrogen or a 2-hydroxymethyl-4-thiazolyl radical/hydrogen or a 2-methyl-4-oxazolyl radical/hydrogen or a 2-hydroxymethyl-4-oxazolyl radical/hydrogen.

48. Compounds according to claim 44, in which $R^{2a}/R^{2b}$ stand for methyl or ethyl/hydrogen.

49. Compounds according to claim 45, in which $R^{2a}/R^{2b}$ stand for methyl or ethyl/hydrogen.

50. Compounds according to claim 46, in which $R^{2a}/R^{2b}$ stand for methyl or ethyl/hydrogen.

51. Compounds according to claim 47, in which $R^{2a}/R^{2b}$ stand for methyl or ethyl/hydrogen.

52. Compounds of general formula I, namely
(4S,7R,8S,9S,13(Z or E),16S(Z))-4,8-dihydroxy-16-(1-fluoro-2-(2-methyl-4-thiazolyl)ethenyl)-1-aza-5,5,7,9,13-pentamethyl-cyclohexadec-13-ene-2,6-dione
(1RS,3S(Z),7S,10R,11S,12S,16RS)-7,11-dihydroxy-3-(1-fluoro-2-(2-methyl-4-thiazolyl)ethenyl)-8,8,10,12,16-pentamethyl-4-aza-17-oxabicyclo[14.1.0]heptadecane-5,9-dione
(4S,7R,8S,9S,13(Z or E),16S(Z))-4,8-dihydroxy-7-ethyl-16-(1-fluoro-2-(2-methyl-4-thiazolyl)ethenyl)-1-aza-5,5,9,13-tetramethyl-cyclohexadec-13-ene-2,6-dione
(1RS,3S(Z),7S,10R,11S,12S,16RS)-7,11-dihydroxy-10-ethyl-3-(1-fluoro-2-(2-methyl-4-thiazolyl)ethenyl-8,8,12,16-tetramethyl-4-aza-17-oxabicyclo[14.1.0]heptadecane-5,9-dione
(4S,7R,8S,9S,13(Z or E),16S(Z))-4,8-dihydroxy-16-(1-fluoro-2-(2-methyloxazol-4-yl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-methyloxazol-4-yl)ethenyl)-8,8,10,12,16-pentamethyl-4-aza-17-oxabicyclo[14.1.0]heptadecane-5,9-dione 4S,7R,8S,9S,13(Z or E),16S(Z))-4,8-dihydroxy-7-ethyl-16-(1-fluoro-2-(2-methyloxazol-4-yl)ethenyl)-1-aza-5,5,9,13-tetramethyl-cyclohexadec-13-ene-2,6-dione 1RS,3S(Z),7S,10R,11S,12S,16RS)-7,11-dihydroxy-10-ethyl-3-(1-fluoro-2-(2-methyloxazol-4-yl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-1-(1-fluoro-2-(2-pyridyl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-fluoro-2-(2-pyridyl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-fluoro-2-(2-pyridyl)ethenyl)-1-aza-5,5,9,13-tetramethyl-cyclohexadec-13-ene-2,6-dione (1RS,3S(Z),7S,10R,11S,12S,16RS)-7,11-dihydroxy-10-ethyl-3-(1-fluoro-2-(2-pyridyl)ethenyl)-8,8,12,16-tetramethyl-4-aza-17-oxabicyclo[14.1.0]heptadecane-5,9-dione (1RS,3S(Z),7S,10R,11S,12S,16RS)-7,11-dihydroxy-10-ethyl-3-(1-chloro-2-(2-methyl-4-thiazolyl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-chloro-2-(2-methyloxazol-4-yl)ethenyl)-1-aza-5,5,7,9,13-pentamethyl-cyclohexadec-13-ene-2,6-dione (1RS,3S(Z),7S,10R,11S,12S,16RS)-7,11-dihydroxy-3-(1-chloro-2-(2-methyloxoazol-4-yl)ethenyl)-8,8,10,12,16-pentamethyl-4-aza-17-oxabicyclo[14.1.0]heptadecane-5,9-dione (4S,7R,8S,9S,13(Z or R),16S(Z))-4,8-dihydroxy-7-ethyl-16-(1-chloro-2-(2-methyoxazol-4-yl)ethenyl)-1-aza-5,5,9,13-tetramethyl-cyclohexadec-13-ene-2,6-dione (1RS,3S(Z),7S,10R,11S,16RS)-7,11-dihydroxy-10-ethyl-3-(1-chloro-2-(2-methyloxazol-4-yl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-chloro-2-(2-pyridyl)ethenyl)-1-aza-5,5,7,9,13-pentamethyl-cyclohexadec-13-ene-2,6-dione (1RS,3S(Z),7S,10R,11S,12S,16RS)-7,11-diyhdroxy-3-(1-chloro-2-(2-pyridyl)ethenyl)-8,8,10,12,16-pentamethyl-4-aza-17-oxabicyclo[14.1.0]heptadecane-5,9-dione (4S,7R,8S,9S,13(Z or E),16S(Z))-4,8-dihydroxy-7-ethyl-16-(1-chloro-2-(2-pyridyl)ethenyl)-1-aza-5,5,9,13-tetramethyl-cyclohexadec-13-ene-2,6-dione (1RS,3S(Z),7S,10R,11S,12S,16RS)-7,11-dihydroxy-10-ethyl-3-(1-chloro-2-(2-pyridyl)ethenyl)-8,8,12,16-tetramethyl-4-aza-17-oxabicyclo[14.1.0]heptadecane-5,9-dione (4S,7R,8S,9S,13(Z or E),16S(Z))-4,8-dihydroxy-16-(1-fluoro-2-(2-methyl-4-thiazolyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihyroxy-3-(1-fluoro-2-(2-methyl-4-thiazolyl)ethenyl)-10,12,16-trimethy)-8,8-(1,3-trimethylene)-4-aza-17-oxabicyclo[14.1.0]hepta-deca-5,9-dione (4S,7R,8S,9S,13(Z or E),16S(Z))-4,8-dihyroxy-9,13-dimethyl-7-ethyl-16-(1-fluoro-2-(2-methyl-4-thiazolyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-fluoro-2-(2-methyl-4-thiazolyl)ethenyl)-8,8-(1,3-trimethylene)-4-aza-17-oxabicyclo[14.1.0]hepta-decane-5,9-dione 4S,7R,8S,9S,13(Z or E),16S(Z))-4,8-dihyroxy-16-(1-chloro-2-(2-methyl-4-thiazolyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-3-(1-chloro-2-(2-methyl-4-thiazolyl)ethenyl)-10,12,16-trimethyl-8,8-(1,3-trimethylene)-4-aza-17-oxabicyclo[14.1.0]hepta-deca-5,9-dione (4S,7R,8S,9S,13(Z or E),16S(Z))-4,8-dihdroxy-9,13-dimethyl-7-ethyl-16-(1-chloro-2-(2-methyl-4-thiazolyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-methyl-4-thiazolyl)ethenyl)-8,8-(1,3-trimethylene)-4-aza-17-oxabicyclo[14.1.0]heptadecane-5,9-dione 4S,7R,8S,9S,13(Z or E),16S(Z))-4,9-dihydroxy-16-(1-fluoro-2-(2-pyridyl)ethenyl)-1-aza-7,9,13-trimethyl-5,5-(1,3-trimethylene)cyclohexadec-13-ene-2,6-dione (1RS,3S(Z),7S,10R,11S,12S,16RS)-7,11-dihydroxy-5-(1-fluoro-2-(2-pyridyl)ethenyl)-10,12,16-trimethyl-8,2-(1,3-trimethylene)-4-aza-17-oxabicyclo[14.1.0]hepta-deca-5,9-dione (4S,7R,8S,9S,13(Z or E),16S(Z))-4,8-dihydroxy-9,13-dimethyl-7-ethyl-16-(1-fluoro-2-(2-pyridyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-fluoro-2-(2-pyridyl)ethenyl)-8,8-(1,3-trimethylene) -4-aza-17-oxabicyclo[14,1,0]hepta-decane-5,9-dione 4S,7R,8S,9S,13(Z or E),16S(Z))-4,8-dihdroxy-16-(1-chloro-2-(2-pyridyl)ethenyl)-1-aza-7,9,13-trimethyl-5,5-(1,3-trimethylene)cyclohexadec-13-ene-2,6-dione (1RS,3S(Z),7S,10R,11S, 12S, 16RS)-7,11-dihydroxy-3-(1-chloro-2-(2-pyridyl)ethenyl)-10,12,16-trimethyl-8,8-(1,3-trimethylene)-4-aza-17-oxabicyclo[14.1.0]hepta-deca-5,9-dione (4S,7R,8S,9S,13(Z or E),16S(Z))-4,8-dihydroxy-9,13-dimethyl-7-ethyl-16-(1-chloro-2-(2-pyridyl)ethenyl)-1-aza-5,5-(1,3-trimethylene)cyclohexadec-13-ene-2,6-dione (1RS,3S(Z),7S,10R,11S,12S,16RS)-7,11-dihydroxy-12,16-dimethyl-10-ethyl-3-(1-chloro-2-(2-pyridyl)ethenyl)-8,8-(1,3-trimethylene)-4-aza-17-oxabicyclo[14.1.0]hepta-decane-5,9-dione.

53. Pharmaceutical preparations that contain at least one compound of general formula I according to claim 1 as well as a pharmaceutically compatible vehicle.

* * * * *

UNITED STATES PATENT AND TRADEMARK OFFICE
CERTIFICATE OF CORRECTION

PATENT NO. : 6,930,102 B2  
DATED : August 16, 2005  
INVENTOR(S) : Ulrich Klar et al.

Page 1 of 1

It is certified that error appears in the above-identified patent and that said Letters Patent is hereby corrected as shown below:

Column 65,  
Line 36, reads "(4S,7R,8S,9S,13(Z or R)," should read -- (4S,7R,8S,9S,13(Z or E), --.

Column 66,  
Line 27 reads "16S(Z))-4,9-dihdroxy-16-(1-" should read -- 16S(Z)-4,8-dihdroxy-16-(1- --.  
Line 31, reads "16-trimethyl-8,2-(1,3-" should read -- 16-trimethyl-8,8-(1,3- --.  
Line 40, reads "-4-aza-17-oxabicyclo[14,1,0]hepta-" should read -- -4-aza-17-oxabicyclo[14.1.0]hepta- --.

Signed and Sealed this

Eighth Day of November, 2005

JON W. DUDAS  
*Director of the United States Patent and Trademark Office*